(12) United States Patent
Hajitou et al.

(10) Patent No.: US 12,331,308 B2
(45) Date of Patent: *Jun. 17, 2025

(54) PHAGEMID VECTOR

(71) Applicant: IMPERIAL COLLEGE INNOVATIONS LIMITED, London (GB)

(72) Inventors: Amin Hajitou, London (GB); Paladd Asavarut, London (GB); Teerapong Yata, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 305 days.

This patent is subject to a terminal disclaimer.

(21) Appl. No.: 17/956,257

(22) Filed: Sep. 29, 2022

(65) Prior Publication Data

US 2023/0265452 A1    Aug. 24, 2023

Related U.S. Application Data

(63) Continuation of application No. 15/772,961, filed as application No. PCT/GB2016/053366 on Oct. 31, 2016, now Pat. No. 11,603,540.

(30) Foreign Application Priority Data

Nov. 2, 2015 (GB) .................................. 1519303

(51) Int. Cl.
| | |
|---|---|
| *C12N 15/864* | (2006.01) |
| *A61K 31/53* | (2006.01) |
| *A61K 48/00* | (2006.01) |
| *C12N 15/86* | (2006.01) |
| *A61K 39/00* | (2006.01) |

(52) U.S. Cl.
CPC .............. *C12N 15/86* (2013.01); *A61K 31/53* (2013.01); *A61K 48/00* (2013.01); *A61K 39/00* (2013.01); *A61K 2039/5256* (2013.01); *C12N 2750/14134* (2013.01); *C12N 2750/14143* (2013.01); *C12N 2750/14144* (2013.01); *C12N 2750/14152* (2013.01); *C12N 2795/00043* (2013.01); *C12N 2795/00044* (2013.01); *C12N 2795/00045* (2013.01); *C12N 2795/14134* (2013.01); *C12N 2795/14143* (2013.01); *C12N 2795/14144* (2013.01); *C12N 2795/14152* (2013.01); *C12N 2799/021* (2013.01); *C12N 2799/04* (2013.01); *C12N 2799/06* (2013.01); *C12N 2800/10* (2013.01); *C12N 2810/00* (2013.01); *C12N 2810/405* (2013.01); *C12N 2820/10* (2013.01); *C12N 2820/55* (2013.01); *C12N 2820/60* (2013.01)

(58) Field of Classification Search
None
See application file for complete search history.

(56) References Cited

U.S. PATENT DOCUMENTS

| | | | |
|---|---|---|---|
| 10,799,542 B2 | 10/2020 | Hajitou et al. | |
| 11,603,540 B2 | 3/2023 | Hajitou et al. | |
| 11,820,792 B2 | 11/2023 | Hajitou et al. | |
| 2007/0128728 A1 | 6/2007 | Bradbury | |
| 2013/0195800 A1 | 8/2013 | Roeth et al. | |
| 2016/0114032 A1 | 4/2016 | Hajitou et al. | |
| 2017/0008969 A1 | 1/2017 | Towner et al. | |
| 2017/0340684 A1 | 11/2017 | Hajitou et al. | |
| 2018/0320200 A1 | 11/2018 | Hajitou et al. | |
| 2019/0062394 A1 | 2/2019 | Yarlagadda et al. | |
| 2019/0083610 A1 | 3/2019 | Hajitou et al. | |
| 2020/0239535 A1 | 7/2020 | Hajitou et al. | |

FOREIGN PATENT DOCUMENTS

| | | | |
|---|---|---|---|
| WO | 9209690 A2 | 6/1992 | |
| WO | 2005019435 A2 | 3/2005 | |
| WO | 2007067818 A2 | 6/2007 | |
| WO | 2007118245 A2 | 10/2007 | |
| WO | 2014184528 A1 | 11/2014 | |
| WO | 2014184529 A1 | 11/2014 | |
| WO | 2017077275 A1 | 5/2017 | |

(Continued)

OTHER PUBLICATIONS

International Search Report and Written Opinion of PCT Application No. PCT/GB2016/053366, dated Jan. 13, 2017, 14 Pages.
International Preliminary Report on Patentability of PCT Application No. PCT/GB2016/053366, dated Jan. 24, 2018, 25 Pages.
Jiang et al., Development of Efficient RNA Interference System Using EGF-Displaying Phagemid Particles, 2008, Acta Pharmacol. Sin., vol. 29(4), pp. 437-442.
Li et al., Cell-Targeted Phagemid Particles Preparation Using *Escherichia Coli* Bearing Ligand-pIII Encoding Helper Phage Genome, 2006, BioTechniques, vol. 41, pp. 706-707.
Search Report of GB1706451.0, dated Jan. 30, 2018, 7 Pages.
International Search Report and Written Opinion of PCT/GB2018/051070, dated Sep. 11, 2018, 21 pages.
Albahrani et al., Selective Cytokine Gene Therapy for the Treatment of Paediatric Brain Cancer, 2017, Human Gene Therapy, vol. 28(8), P037, 1 page.

(Continued)

*Primary Examiner* — Michael D Burkhart
(74) *Attorney, Agent, or Firm* — Linda B. Huber; Nixon Peabody LLP

(57) ABSTRACT

The invention provides hybrid and recombinant phagemid vectors for expressing a transgene in a target cell transduced with the vector. A recombinant phagemid particle comprises at least one transgene expression cassette which encodes an agent which exerts a biological effect on the target cell, characterised in that the phagemid particle comprises a genome which lacks at least 50% of its bacteriophage genome. The invention extends to the use of such phagemid expression systems as a research tool, and for the delivery of transgenes in a variety of gene therapy applications, DNA and/or peptide vaccine delivery and imaging techniques. The invention extends to in vitro, in vivo or in situ methods for producing viral vectors, such as recombinant adeno-associated viruses (rAAV) or lentivirus vectors (rLV), and to genetic constructs used in such methods.

20 Claims, 30 Drawing Sheets

Specification includes a Sequence Listing.

(56) References Cited

FOREIGN PATENT DOCUMENTS

WO      2018197859 A1      11/2018

OTHER PUBLICATIONS

Carl H. June, Adoptive T Cell Therapy for Cancer in the Clinic, 2007, The Journal of Clinical Investigation, vol. 117 (6), pp. 1466-1476.

Lund et al., Pseudovirions as Vehicles for the Delivery of siRNA, 2010, Pharm. Research, vol. 27(3), pp. 400-420.

Redeker et al., Improving Adoptive T Cell Therapy: The Particular Role of T Cell Costimulation, Cytokines, and Post-Transfer Vaccination, 2016, Frontiers in Immunology, vol. 7(345), 8 Pages.

Notice of Allowance for U.S. Appl. No. 15/772,961 dated Jun. 29, 2022, 12 pages.

Larocca et al., Receptor-Targeted Gene Delivery Using Multivalent Phagemid Particles, Molecular Therapy, 2001, vol. 3(4), pp. 476-484.

Cloning Vector Puc119 Product Information Sheet #V33402, Molecular Biotechnology, 2014.

Berraondo et al., Cytokines in clinical cancer immunotherapy, British Journal of Cancer, 2019, vol. 120, pp. 6-15.

Jafari et al., Phage Particles as Vaccine Delivery Vehicles: Concepts, Applications and Prospects, 2015, vol. 16(18), pp. 8019-8029.

Rallis et al., Cytokine-based Cancer Immunotherapy: Challenges and Opportunities for IL-10, Anticancer Research 41, 2021, pp. 3247-3252.

Shen et al., Anti-cancer therapy with TNFa and IFNy: a comprehensive review, Cell Proliferation, 2018, vol. 51, pp. 1-11.

Sunderland et al., Phage-Enabled Nanomedicine: From Probes to Therapeutics in Precision Medicine, Angew Chem Int Ed Engl., 2017, vol. 56(8), pp. 1-57.

Comparing AAVP and PAAV

| | Next-generation PAAV vectors |
|---|---|
| Relative genome size | c. 6000 bases (42% of AAVP) |
| Relative virus size | ~60% shorter than AAVP |
| Production yield | up to 400,000X current AAVP yields |
| Payloads per particle | Multiple (AAVP can only carry 1 payload) |
| Biodistribution | *Potentially better* |

AAVP (c.14Kb)    PAAV (6Kb)

Figure 2
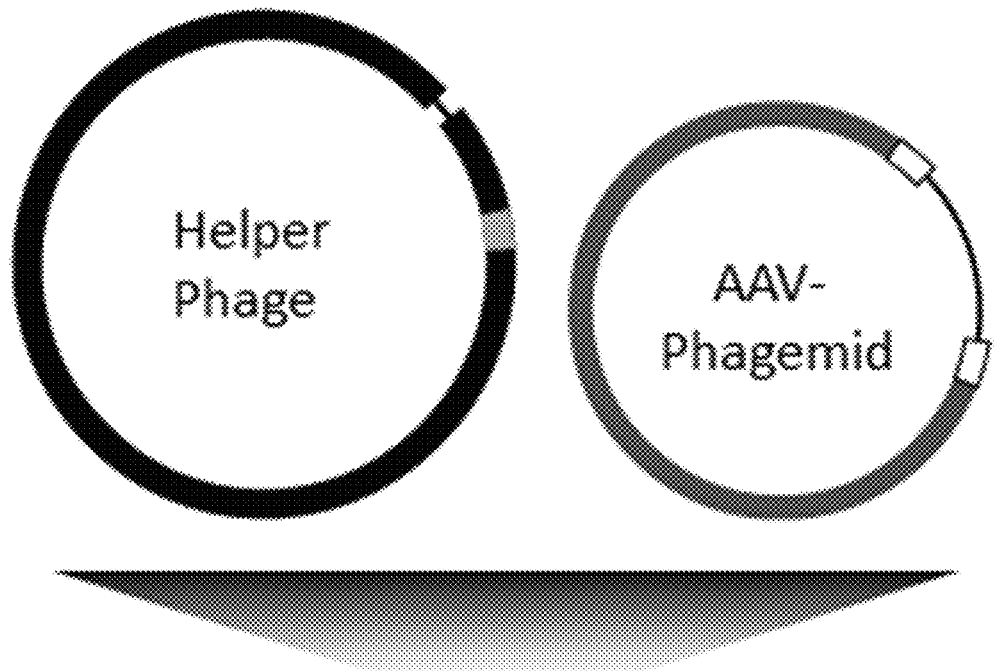
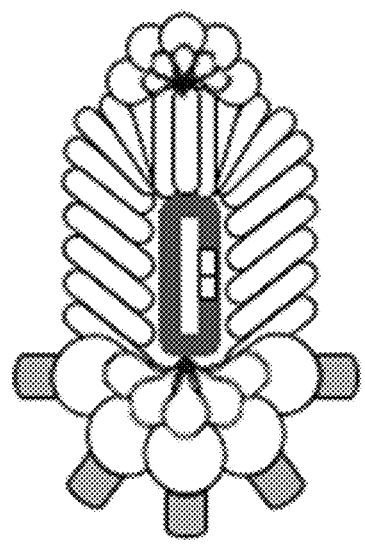
*Phagemid/Adeno-associated Virion (PAAV)*

AAV ProParvovec (IRES-GFP, D/J serotype) Prototype
19,141 bp

PHAGEMID VECTOR

CROSS-REFERENCE TO RELATED APPLICATIONS

This application is a continuation of U.S. patent application Ser. No. 15/772,961 filed May 2, 2018, which is the National Phase of International Application PCT/GB2016/053366 filed Oct. 31, 2016, which designated the United States and that International Application was published under PCT Article 21(2) in English. This application also includes a claim of priority under 35 U.S.C. § 119(a) and § 365(b) to British patent application No. GB 1519303.0 filed Nov. 2, 2015, the entirety of which is hereby incorporated by reference.

REFERENCE TO SEQUENCE LISTING

This application contains a Sequence Listing submitted as an electronic file named "76748US2 sequence listing.xml", having a size in bytes of 38,486 bytes, and created on Apr. 12, 2023 (WIPO production date). The information contained in this electronic file is hereby incorporated by reference in its entirety.

The present invention relates to phagemid vectors and associated phagemid particles, and in particular to hybrid and recombinant phagemid vectors, particles and expression systems. The invention extends to the use of such phagemid particles and expression systems as a research tool, and for the delivery of transgenes in a variety of gene therapy applications, DNA and/or peptide vaccine delivery and imaging techniques. The invention extends to in vitro, in vivo or in situ methods for producing viral vectors, such as recombinant adeno-associated viruses (rAAV) or lentivirus vectors (rLV), and to genetic constructs used in such methods.

In the past decade, a number of viral and non-viral vectors have emerged as potential delivery vectors for industrial and therapeutic applications. An important property of vectors, in addition to being efficient at delivering genes, is that it must also be easily produced and commercially viable. Despite the large body of basic research that must underpin the vector design and refinement, vector production is an area that must be addressed in order for successful commercialization to occur. Adeno-associated virus (AAV)-mediated gene therapy is a case in point, as vector production has been a bottleneck for clinical translation. Recombinant AAV (rAAV) is an attractive vector in gene therapy. However, efficient vector production at commercial scales is not yet possible. A variety of expression systems have been developed for rAAV production.

While transfection-based protocols have been the gold standard for high-purity laboratory-scale production, they cannot be efficiently translated to commercial-scale protocols. Current methods for commercial-scale production rely on the use of eukaryotic viruses to rescue AAV vectors from a producer cell line. Despite being more efficient, the use of infectious eukaryotic viruses is a major point of concern, not only when purifying viral particles, but also regarding safeness for in vivo use.

AAV are non-enveloped viruses with a 4.7 Kb wild type genome that is flanked by inverted terminal repeats (ITRs). The genome contains two open reading frames, rep and cap, which provide proteins necessary for replication and encapsidation of the viral genome. In nature, wild type AAV is found in the presence of adenovirus (Ad) as they provide adeno-helper proteins that are essential for packaging of the AAV genome in to icosahedral virions. Therefore, AAV production relies on three key elements: the ITR-flanked genome, rep and cap, and adeno-helper genes.

At present, laboratory scale production of rAAV uses DNA transfection to introduce all three genetic elements in to human embryonic kidney HEK293 cells, which is a suitable mammalian producer cell as they inherently express an adeno-helper protein from immortalization. Although laboratory scale production provides rAAV of high purity, transfection methods are not suitable for large-scale production and face major limitations, including inefficiency, which leads to low rAAV yields and high costs. Also, in many cases, live viruses, such as adenovirus or herpes simplex virus, are used to efficiently supply the helper functions, which present significant health and safety concerns for in vivo use.

Large-scale commercial production of rAAV is possible, but it comes at very high costs and results in the production of low purity rAAV. Alongside the cell factory system involving large-scale adherent culture of HEK293 cells, the baculovirus expression vectors (BEVS) and Sf9 insect cell system has served as the most reliable candidate system for large-scale rAAV production. Recent studies have shown that this system is amenable to genetic modification, and that transcriptional control can be used to regulate rep gene expression, which is toxic to the producer cell. Nevertheless, despite its advantageous capabilities, the BEVS/Sf9 paradigm remains costly and lacks refinement, as baculovirus contamination of rAAV preparations is almost unavoidable, and with a risk of high immunogenicity.

In 2006, Hajitou et al. attempted to fulfil the need for vectors by creating a hybrid between recombinant adeno-associated virus (rAAV) and filamentous bacteriophage (i.e. phage), called the Adeno-associated Virus/Phage (AAVP) (Nature protocols 2, 523-531 (2007); Cell 125, 385-398 (2006)). The AAVP is a hybrid phage vector in which gene expression is under the control of a eukaryotic transgene cassette flanked by internal terminal repeats (ITRs) of AAV2, and inserted in an intergenomic region of bacteriophage. This vector combines the specificity of bacteriophage vectors with the genetic characteristics of AAV, yielding a virus that can reproduce only in prokaryotic hosts and transduce mammalian cells with the expression profile similar to rAAV. Importantly, rAAV can be rescued from HEK293 cells transduced with AAVP following transfection with rep- and cap-expressing plasmid, and subsequent infection with wild-type adenovirus type 5. Hence, the AAVP vector possesses favourable characteristics of mammalian and prokaryotic viruses, and does not suffer from the disadvantages that those individual vectors normally carry.

However, the AAVP still has certain inherent limitations of bacteriophage and thus leaves room for significant improvement of AAVP or phage vectors in general, and so there is a need for designing novel superior phage-based vectors. For instance, AAVP are a hybrid between two virus species (i.e. bacteriophage and AAV), AAVP vectors contain the genome of both the eukaryotic and prokaryotic viruses. Despite being essential for viral reproduction, the prokaryotic genome is functionally or therapeutically irrelevant. Inclusion of the phage viral genome thus deleteriously affects vector efficiency and the production method, and ultimately leads to AAVP's relatively low gene transduction efficacy when compared to mammalian viruses. There is therefore a need to provide novel modified bacteriophage systems, which can be used both in gene therapy techniques and for large-scale production of recombinant viral vectors, such as adeno-associated virus (AAV) or lentivirus.

The research described herein has developed a so-called "hybrid phagemid viral vector system", with the new phagemid particle being referred to as Phagemid/Adeno-associated Virion (i.e. PAAV). Another name used by the inventors for the novel vectors they have created is "phasmid". Unlike the prior art AAVP genome, which consists of a rAAV cassette inserted in to the filamentous phage genome, the PAAV genome of the invention does not contain any structural bacteriophage genes, and so a prokaryotic helper virus is required to facilitate vector assembly in the host.

Thus, according to a first aspect of the invention, there is provided a recombinant phagemid particle for expressing a transgene in a target cell transduced with the particle, the phagemid particle comprising at least one transgene expression cassette which encodes an agent which exerts a biological effect on the target cell, characterised in that the phagemid particle comprises a genome which lacks at least 50% of its bacteriophage genome.

Advantageously, re-engineering hybrid viral vectors (e.g. AAV or lentivirus) into the phagemid particle according to the first aspect, substantially lacking the phage genome from which the particle is derived, dramatically enhances the functional properties of the resultant vector (i.e. the phagemid particle). Altering the viral expression system to a phagemid-based system according to the invention expands the possibility of applying phagemid viral vectors in a much broader context. By eliminating at least 50% of the bacteriophage genome, which constitutes over 50% of the genome size, from the particle's genome, the resultant particle size of the phagemid particle is dramatically reduced.

The term "phagemid particle" can refer to a hybrid phagemid genome encapsulated by phage-derived coat proteins. The hybrid phagemid genome is a "phagemid genome" (i.e. a genetic construct containing two origins of replication—one from bacteriophage (e.g. F1), and one from bacteria (e.g. pUC1)). In one embodiment, the phagemid genome may contain an incorporated "recombinant transgene cassette from AAV" (rAAV), and is therefore a hybrid and not a conventional phagemid genome with a normal (i.e. generic, non-viral) recombinant transgene expression cassette. The phagemid particle can refer to the hybrid phagemid genome (i.e. the invention) that has been encapsulated by phage proteins derived from a trans-acting agent (such as a helper phage).

While allowing additional capacities to incorporate very large or multiple transgene cassettes, these smaller phagemid particles also display added advantages in enhanced gene transfer, production yield, biodistribution and evasion from eukaryotic cellular barriers. Another significant advantage of using the phagemid particle of the invention is that they have the ability to accommodate extremely large and numerous transgene cassettes or gene inserts, such as genes of the three plasmids used for recombinant virus (e.g. rAAV or lentivirus) production by transfection, as described hereinafter. Hence, by combining the genetic components for viral production in a single or multiple phagemid vector(s), an efficient commercial-scale virus-producing gene delivery system has been designed.

Preferably, the phagemid particle comprises a virion.

One preferred embodiment of the genome of the recombinant phagemid particle is illustrated on FIG. 3, with preferred components being shown on FIGS. 4-6.

Preferably, the genome of the recombinant phagemid particle comprises a packaging signal for enabling replication of the phagemid genome into single-stranded DNA, which can subsequently be packaged into the phagemid particle inside a prokaryotic host. The packaging signal may preferably comprise an origin of replication. For example, the origin of replication preferably comprises an F1 ori, more preferably from an F1 bacteriophage. The DNA sequence of one embodiment of the F1 ori is represented herein as SEQ ID No: 1, as follows:

[SEQ ID NO: 1]
```
ACGCGCCCTGTAGCGGCGCATTAAGCGCGGCGGGTGTGGT
GGTTACGCGCAGCGTGACCGCTACACTTGCCAGCGCCCTA
GCGCCCGCTCCTTTCGCTTTCTTCCCTTCCTTTCTCGCCA
CGTTCGCCGGCTTTCCCCGTCAAGCTCTAAATCGGGGGCT
CCCTTTAGGGTTCCGATTTAGTGCTTTACGGCACCTCGAC
CCCAAAAAACTTGATTTGGGTGATGGTTCACGTAGTGGGC
CATCGCCCTGATAGACGGTTTTTCGCCCTTTGACGTTGGA
GTCCACGTTCTTTAATAGTGGACTCTTGTTCCAAACTGGA
ACAACACTCAACCCTATCTCGGGCTATTCTTTTGATTTAT
AAGGGATTTTGCCGATTTCGGCCTATTGGTTAAAAAATGA
GCTGATTTAACAAAAATTTAACGCGAATTTTAACAAAATA
TTAACGTTTACAATTT
```

Preferably, the genome of the recombinant phagemid particle comprises an origin of replication for enabling replication of double-stranded vector inside a prokaryotic host. Preferably, the origin of replication enables high copy number replication of the vector inside the host. Preferably, the origin of replication comprises a pUC ori. The DNA sequence of one embodiment of the pUC ori is represented herein as SEQ ID No: 2, as follows:

[SEQ ID NO: 2]
```
TTGAGATCCTTTTTTTCTGCGCGTAATCTGCTGCTTGCAA
ACAAAAAAACCACCGCTACCAGCGGTGGTTTGTTTGCCGG
ATCAAGAGCTACCAACTCTTTTTCCGAAGGTAACTGGCTT
CAGCAGAGCGCAGATACCAAATACTGTCCTTCTAGTGTAG
CCGTAGTTAGGCCACCACTTCAAGAACTCTGTAGCACCGC
CTACATACCTCGCTCTGCTAATCCTGTTACCAGTGGCTGC
TGCCAGTGGCGATAAGTCGTGTCTTACCGGGTTGGACTCA
AGACGATAGTTACCGGATAAGGCGCAGCGGTCGGGCTGAA
CGGGGGGTTCGTGCACACAGCCCAGCTTGGAGCGAACGAC
CTACACCGAACTGAGATACCTACAGCGTGAGCTATGAGAA
AGCGCCACGCTTCCCGAAGGGAGAAAGGCGGACAGGTATC
CGGTAAGCGGCAGGGTCGGAACAGGAGAGCGCACGAGGGA
GCTTCCAGGGGAAACGCCTGGTATCTTTATAGTCCTGTC
GGGTTTCGCCACCTCTGACTTGAGCGTCGATTTTTGTGAT
GCTCGTCAGGGGGGCGGAGCCTATGGAAA
```

Alternatively, in another embodiment, the phagemid particle may be designed such that it integrates into the genome of a host cell. In this case, nucleic acid sequences, which favour targeted integration (e.g. by homologous recombination) of the particle's genome are envisaged. Hence, the genome of the recombinant phagemid particle may comprise one or more DNA sequence, which favours targeted integration into a host genome.

In one embodiment, the phagemid particle may be used as an experimental research tool, and used ex vivo or in vitro.

In another embodiment, preferably the phagemid particle may be used as a recombinant vector for the delivery of the transgene to a tissue specific target, irrespective of whether the vector is administered systemically or locally to a subject in vivo, applied to a mixture of cells in vitro, or applied to an organ ex vivo. Preferably, the at least one transgene expression cassette comprises a viral transgene expression cassette, more preferably a mammalian viral transgene expression cassette. For example, the at least one transgene expression cassette may, in one preferred embodiment, comprise a lentivirus transgene expression cassette. The at least one transgene expression cassette is preferably an adeno-associated virus (AAV) transgene expression cassette.

The transgene expression cassette may comprise any nucleic acid encoding an agent, which may have therapeutic or industrial utility in the target cell or tissue. In one embodiment of the invention, the nucleic acid may be DNA, which may be genomic DNA or cDNA. Non-naturally occurring cDNA may be preferred in some embodiments. In another embodiment, the nucleic acid may be RNA, such as antisense RNA or shRNA.

In one preferred embodiment, the transgene expression cassette may comprise shRNA configured to target mTOR expression in a tumour cell. As shown in the Example 7, down-regulation of mTOR expression in tumour cells (e.g. medulloblastoma cells) may be achieved with treatment with RGD4C-phagemid carrying the mTOR/shRNA (RGD4C-mTOR/shRNA).

The agent encoded by the nucleic acid may be a polypeptide or protein. For example, in embodiments where the phagemid particle of the first aspect is used to treat cancer, the transgene may encode the Herpes simplex virus thymidine kinase gene, which may subsequently exert a therapeutic effect on the target tumour cell.

In another preferred embodiment, therefore, the transgene expression cassette may encode TNFα for expression in a tumour cell. As shown in Example 7, RGD4C-phagemid can successfully deliver TNFα to DIPG in a selective manner, resulting in apoptosis induction. Therefore, RGD4C-phagemid-TNFα has therapeutic potential for use in targeted therapy against DIPG.

However, it will be appreciated that the type of cell, which is targeted by the recombinant phagemid particle depends on the type of cell-targeting ligand expressed on the surface of the particle.

The transgene expression cassette may comprise one or more functional elements required for expression of the nucleic acid in the target cell. For example, preferably the transgene expression cassette comprises a promoter, such as the CMV promoter. The DNA sequence of one embodiment of the CMV promoter is represented herein as SEQ ID No: 3, as follows:

```
                                          [SEQ ID NO: 3]
ACGCGTGGAGCTAGTTATTAATAGTAATCAATTACGGGGT

CATTAGTTCATAGCCCATATATGGAGTTCCGCGTTACATA

ACTTACGGTAAATGGCCCGCCTGGCTGACCGCCCAACGAC
```

```
                         -continued
CCCCGCCCATTGACGTCAATAATGACGTATGTTCCCATAG

TAACGTCAATAGGGACTTTCCATTGACGTCAATGGGTGGA

GTATTTACGGTAAACTGCCCACTTGGCAGTACATCAAGTG

TATCATATGCCAAGTACGCCCCCTATTGACGTCAATGACG

GTAAATGGCCCGCCTGGCATTATGCCCAGTACATGACCTT

ATGGGACTTTCCTACTTGGCAGTACATCTACGTATTAGTC

ATCGCTATTACCATGGTGATGCGGTTTTGGCAGTACATCA

ATGGGCGTGGATAGCGGTTTGACTCACGGGGATTTCCAAG

TCTCCACCCCATTGACGTCAATGGGAGTTTGTTTTGCACC

AAAATCAACGGGACTTTCCAAATGTCGTAACAACTCCGC

CCCATTGACGCAAATGGGCGGTAGGCGTGTACGGTGGGAG

GTCTATATAAGCAGAGCTCGTTTAGTGAACCGTCAGATCG

CCTGGAGACGCCATCCACGCTGTTTTGACCTCCATAGAAG

ACACCGGGACCGATCCAGCCTCC
```

In another preferred embodiment, the transgene expression cassette comprises a grp78 promoter. The nucleic acid sequence of one embodiment of the grp78 promoter is represented herein as SEQ ID No: 8, as follows:

```
                                          [SEQ ID NO: 8]
CCCGGGGGCCCAACGTGAGGGGAGGACCTGGACGGTTACC

GGCGGAAACGGTTTCCAGGTGAGAGGTCACCCGAGGGACA

GGCAGCTGCTCAACCAATAGGACCAGCTCTCAGGGCGGAT

GCTGCCTCTCATTGGCGGCCGTTAAGAATGACCAGTAGCC

AATGAGTCGGCTGGGGGCGCGTACCAGTGACGTGAGTTG

CGGAGGAGGCCGCTTCGAATCGGCAGCGGCCAGCTTGGTG

GCATGAACCAACCAGCGGCCTCCAACGAGTAGCGAGTTCA

CCAATCGGAGGCCTCCACGACGGGGCTGCGGGGAGGATAT

ATAAGCCGAGTCGGCGACCGGCGCGCTCGATACTGGCTGT

GACTACACTGACTTGGAC
```

Preferably, the transgene expression cassette comprises nucleic acid for encoding a polyA tail attachable to the expressed agent. The DNA sequence of one embodiment of the nucleic acid for encoding a polyA tail is represented herein as SEQ ID No: 4, as follows:

```
                                          [SEQ ID NO: 4]
ACGGGTGGCATCCCTGTGACCCCTCCCCAGTGCCTCTCCT

GGCCCTGGAAGTTGCCACTCCAGTGCCCACCAGCCTTGTC

CTAATAAAATTAAGTTGCATCATTTTGTCTGACTAGGTGT

CCTTCTATAATATTATGGGGTGGAGGGGGGTGGTATGGAG

CAAGGGGCAAGTTGGGAAGACAACCTGTAGGGCCTGCGGG

GTCTATTGGGAACCAAGCTGGAGTGCAGTGGCACAATCTT

GGCTCACTGCAATCTCCGCCTCCTGGGTTCAAGCGATTCT

CCTGCCTCAGCCTCCCGAGTTGTTGGGATTCCAGGCATGC
```

-continued

```
ATGACCAGGCTCAGCTAATTTTTGTTTTTTTGGTAGAGAC

GGGGTTTCACCATATTGGCCAGGCTGGTCTCCAACTCCTA

ATCTCAGGTGATCTACCCACCTTGGCCTCCCAAATTGCTG

GGATTACAGGCGTGAACCACTGCTCCCTTCCCTGTCCTT
```

Preferably, the transgene expression cassette comprises left and/or right Inverted Terminal Repeat sequences (ITRs). An ITR can be specific to an AAV or lentivirus serotype, and can be any sequence, so long as it forms a hairpin loop in its secondary structure. For example, the AAV serotype may be AAV1-9, but is preferably AAV1, AAV2, AAV5, AAV6 or AAV8. The DNA sequence of one embodiment (left ITR from a commercially available AAV plasmid) of the ITR is represented herein as SEQ ID No: 5, as follows:

```
                                          [SEQ ID NO: 5]
CCTGCAGGCAGCTGCGCGCTCGCTCGCTCACTGAGGCCGC

CCGGGCGTCGGGCGACCTTTGGTCGCCCGGCCTCAGTGAG

CGAGCGAGCGCGCAGAGAGGGAGTGGCCAACTCCATCACT

AGGGGTTCCT
```

The DNA sequence of another embodiment (right ITR from a commercially available AAV plasmid) of the ITR is represented herein as SEQ ID No: 6, as follows:

```
                                          [SEQ ID NO: 6]
AGGAACCCCTAGTGATGGAGTTGGCCACTCCCTCTCTGCG

CGCTCGCTCGCTCACTGAGGCCGGGCGACCAAAGGTCGCC

CGACGCCCGGGCTTTGCCCGGGCGGCCTCAGTGAGCGAGC

GAGCGCGCAGCTGCCTGCAGG
```

Preferably, the genome of the recombinant phagemid particle comprises a selection marker, which will depend on the host cell in which the vector is harboured, for example for conferring ampicillin resistance in a host cell, preferably a bacterium. The marker provides selection pressure during production of the phagemid particle in the host cell.

Preferably, the recombinant phagemid particle comprises one or more capsid minor coat protein. The recombinant phagemid particle may comprise a pIII capsid minor coat protein that is configured to display a cell-targeting ligand for enabling delivery of the particle to the target cell. Preferably, the recombinant phagemid particle comprises one or more capsid major coat protein. The recombinant phagemid particle may comprise at least one pVIII capsid major coat protein that is configured to display a foreign peptide thereon.

The recombinant phagemid particle may comprise a modification of the capsid structure, for example by treatment, or chemical or biochemical conjugation. Examples of suitable modifications may include cross-linking peptide residues on to the phagemid particle. In another embodiment, the recombinant phagemid particle may comprise one or functional peptide attached to the capsid thereof. For example, a functional peptide may comprise a nuclear translocation signal. The phagemid particle may therefore be multifunctional, and use features disclosed in WO 2014/184528.

In another embodiment, the recombinant phagemid particle may be combined with a cationic polymer to form a complex having a net positive charge, as described in WO 2014/184529. The cationic polymer may be selected from a group consisting of: chitosan; poly-D-lysine (PDL); diethylaminoethyl (DEAE); diethylaminoethyl-dextran (DEAE-.DEX); polyethyleneimine (PEI); polybrene; protamine sulphate; and a cationic lipid. Preferably, the cationic lipid is selected from the group consisting of Fugene®, Lipofectamine®, and DOTAP (N-[1-(2,3-Dioleoyloxy)propyl]-N,N,N-trimethylammonium methyl-sulfate). Preferably, the cationic polymer comprises DEAE, more preferably DEAE-.DEX.

Preferably, the phagemid particle comprises a genome which substantially lacks the phage genome from which the particle is derived. Preferably, the genome of the recombinant phagemid particle lacks at least 60%, more preferably at least 70%, and even more preferably at least 80% of the bacteriophage genome from which it is derived. More preferably, the genome of the recombinant phagemid particle lacks at least 90%, more preferably at least 95%, and even more preferably at least 99% of the bacteriophage genome from which it is derived. Preferably, the genome of the recombinant phagemid particle lacks all of the bacteriophage genome from which it is derived. As discussed above, however, the genome of the phagemid viral particle may, in some embodiments, comprise the bacteriophage origin of replication for enabling replication of the particle into single-stranded DNA, i.e. F1 bacteriophage ori.

Preferably, the phagemid particle lacks bacteriophage structural genes in its genome required for the formation, packaging or extrusion of the particle from a prokaryotic host. Such structural genes encode the capsid proteins etc. Preferably, the phagemid particle comprises a genome which lacks a gene encoding a minor or major coat protein from which the particle is derived. Preferably, the phagemid particle comprises a genome which lacks a pIII capsid minor coat protein, or which lacks a pVIII capsid major coat protein. Most preferably, the phagemid particle comprises a genome which lacks both a pIII capsid minor coat protein, and a pVIII capsid major coat protein.

Thus, the recombinant phagemid particle preferably comprises a replication-deficient, virus-like-particle or virion constructed from, and displaying, the structural components, including but not limited to proteins and other conjugated compounds, derived from a bacteriophage, despite the genome of the particle not containing the structural genes of a bacteriophage from which it is derived.

Accordingly, given that the genome of the recombinant phagemid particle of the first aspect lacks the derivative phage genome, including the structural genes, an alternative system is required in order to provide the necessary structural (i.e. capsid) genes that are required to package the recombinant phagemid genome in a bacteriophage capsid to produce the particle of the invention. Accordingly, the inventors have devised a novel system for producing the particles of the first aspect, involving the use of a separate so-called "helper virus" vector. In effect, therefore, the particle of the first aspect is a hybrid phagemid vector, which includes components of a phagemid and a eukaryotic virus.

Hence, in a second aspect, there is provided a system for producing a recombinant phagemid particle from a prokaryotic host, the system comprising:—
  (i) a first vector configured to persist inside a prokaryotic host, and comprising at least one transgene expression cassette, and a packaging signal for enabling replication of the vector into single-stranded DNA; and (ii) a second vector comprising nucleic acid encoding structural proteins required for packaging the single-stranded DNA, resulting in the formation and extrusion of a recombinant phagemid particle from the prokaryotic host.

Advantageously, separating the reproductive elements of the phagemid particle into the first "therapeutic" vector carrying the transgene, and the second separate "helper" vector carrying the viral packaging structural genes substantially decreases the genome/vector size, and thereby significantly increases transgene capacity. In embodiments in which the phagemid particle is used therapeutically, this is a particularly useful advantage for gene therapy applications of the new system. Consequently, this results in an enhanced production yield, gene transduction efficiency and flexibility of the vector system for other applications.

The novelty of the system of the second aspect is its ability to package the genome of eukaryotic viruses (such as AAV or lentivirus), which is provided by the first vector, into a prokaryotic virus capsid (i.e. bacteriophage), which is provided by the second vector. Thus, while the prior art system (i.e. AAVP) is a chimera of two genomes, the system of the second aspect (i.e. PAAV) is a chimera between prokaryotic viral phenotypes and a eukaryotic viral genotype.

Preferably, the system of the second aspect is used to produce the recombinant phagemid particle according to the first aspect. Preferably, the first vector therefore comprises the genome of the recombinant phagemid particle. The packaging signal of the first vector may preferably comprise an origin or replication. Preferably, the origin of replication in the first vector comprises an F1 ori, more preferably from an F1 bacteriophage.

Preferably, the first vector comprises a second origin of replication for enabling replication of double-stranded vector inside a prokaryotic host. Preferably, the origin of replication enables high copy number replication of the vector inside the host. Preferably, the origin of replication comprises a pUC ori. Alternatively, the first vector may comprise one or more DNA sequence, which favours targeted integration into a host genome, thus removing the requirement for any origin of replication.

The transgene expression cassette comprises a viral transgene expression cassette, more preferably a mammalian viral transgene expression cassette. For example, the at least one transgene expression cassette may comprise a lentivirus transgene expression cassette or a AAV transgene expression cassette. An AAV transgene expression cassette is preferred.

One preferred embodiment of the second vector is illustrated in FIG. 7, with preferred components being shown in FIG. 8. The second vector or "helper phage" is preferably a bacteriophage engineered specifically for rescuing the phagemid particles carrying the first vector (i.e. the phagemid particle's genome) from prokaryotic hosts, an embodiment of which is shown in FIG. 3. The second vector (i.e. the helper phage) is therefore provided to lend its proteins and polypeptides to the first vector (i.e. the phagemid particle's genome), or any other DNA entity that contains a functional packaging signal and/or a single stranded origin or replication. The second vector is most preferably replication-defective. Preferably, the second vector comprises a disrupted packaging signal, which significantly deters its ability to package itself into phage particles. Preferably, the second vector comprises a disrupted origin of replication. In one embodiment, the disrupted origin of replication is a medium copy number origin, such as p15a. In another embodiment, the disrupted origin of replication is a low copy number origin, such as a pMB1. Preferably, the first vector (i.e. the phagemid particle's genome) is configured to outcompete with the second vector (i.e. the helper phage) in both replication and packaging.

The genome of the second vector may be engineered to give the resultant recombinant phagemid particle targeting properties (or multifunctional properties as described in WO 2014/184528). Hence, it provides the structural capsid proteins for phagemid particle assembly. Preferably, the second vector comprises nucleic acid encoding one or more capsid minor coat proteins, or one or more capsid major coat proteins. All capsid proteins may either be wild type or recombinant, present in single or multiple copies, and modified to display chimeric or synthetic peptides. This includes the display of antigens of other viruses for peptide vaccine delivery or as an adjuvant in the case that a DNA vaccine (delivered by the phagemid particle of the first aspect) is desired.

In one embodiment, therefore, the second vector may comprise a first nucleic acid sequence encoding a pIII capsid minor coat protein that is configured to display a cell-targeting ligand for enabling delivery of the recombinant phagemid particle to a target cell (e.g. a tumour). Therefore, it may be desired to induce a 9-amino acid mutation in the pIII minor coat protein of the recombinant phagemid particle in order to confer its specificity to tumour cells and angiogenic tumour-associated endothelial cells that express $\alpha_v\beta_3$ and $\alpha_v\beta_5$ integrins. Thus, the genome of the second vector may comprise the RGD4C targeting peptide (CDCRGDCFC—SEQ ID No: 7).

In another embodiment, the second vector may comprise a second nucleic acid sequence encoding at least one pVIII capsid major coat protein that is configured to display a foreign peptide thereon. Thus, it may be desired to induce a mutation in the wild pVIII major coat protein of the recombinant phagemid particle in order to display a short peptide, for example less than 10 amino acids long. The short peptide may be a targeting moiety or have inherent biological/chemical functionality in vivo or in vitro. For example, immune stimulation in vivo via antigen display, or binding to nanoparticles (e.g. gold) in vitro via displaying a gold-binding peptide.

The first vector may be a member of the Retroviridae family, or of the Orthoretrovirinae Sub-family. The first vector may be a member of the Lentivirus genus. Preferably, the first vector is a member of the Parvoviridae family or sub-family. Preferably, the first vector is a member of the Dependoparvovirus, or adeno-associated virus species.

Once the first vector (i.e. the phagemid particle's genome) and the second vector (i.e. the Helper phage) have been constructed, they are used together to produce, in a prokaryotic host, the recombinant phagemid particle of the first aspect. It will be appreciated that the packaging signal (e.g. the origin of replication) of the first vector, which is for enabling replication of the phagemid genome into single-stranded DNA, functions to signal the second vector (i.e. the helper phage) structural proteins to package the phagemid genome (i.e. they work together in trans in the host) to create the particle of the first aspect.

In one preferred embodiment, the first vector (phagemid particle genome) comprises a nucleic acid sequence substantially as set out in SEQ ID No: 9, or a fragment or variant thereof, wherein SEQ ID No: 9 is represented as follows:

[SEQ ID No: 9]
CCTGCAGGCAGCTGCGCGCTCGCTCGCTCACTGAGGCCGC

CCGGGCGTCGGGCGACCTTTGGTCGCCCGGCCTCAGTGAG

CGAGCGAGCGCGCAGAGAGGGAGTGGCCAACTCCATCACT

AGGGGTTCCTGCGGCCGC---TRANSGENE---AGGAACC

CCTAGTGATGGAGTTGGCCACTCCCTCTCTGCGCGCTCGC

TCGCTCACTGAGGCCGGGCGACCAAAGGTCGCCCGACGCC

CGGGCTTTGCCCGGCGGCCTCAGTGAGCGAGCGAGCGCG

CAGCTGCCTGCAGGGGCGCCTGATGCGGTATTTTCTCCTT

ACGCATCTGTGCGGTATTTCACACCGCATACGTCAAAGCA

ACCATAGTACGCGCCCTGTAGCGGCGCATTAAGCGCGGCG

GGTGTGGTGGTTACGCGCAGCGTGACCGCTACACTTGCCA

GCGCCCTAGCGCCCGCTCCTTTCGCTTTCTTCCCTTCCTT

TCTCGCCACGTTCGCCGGCTTTCCCCGTCAAGCTCTAAAT

CGGGGGCTCCCTTTAGGGTTCCGATTTAGTGCTTTACGGC

ACCTCGACCCCAAAAAACTTGATTTGGGTGATGGTTCACG

TAGTGGGCCATCGCCCTGATAGACGGTTTTTCGCCCTTTG

ACGTTGGAGTCCACGTTCTTTAATAGTGGACTCTTGTTCC

AAACTGGAACAACACTCAACCCTATCTCGGGCTATTCTTT

TGATTTATAAGGGATTTTGCCGATTTCGGCCTATTGGTTA

AAAAATGAGCTGATTTAACAAAAATTTAACGCGAATTTTA

ACAAAATATTAACGTTTACAATTTTATGGTGCACTCTCAG

TACAATCTGCTCTGATGCCGCATAGTTAAGCCAGCCCCGA

CACCCGCCAACACCCGCTGACGCGCCCTGACGGGCTTGTC

TGCTCCCGGCATCCGCTTACAGACAAGCTGTGACCGTCTC

CGGGAGCTGCATGTGTCAGAGGTTTTCACCGTCATCACCG

AAACGCGCGAGACGAAAGGGCCTCGTGATACGCCTATTTT

TATAGGTTAATGTCATGATAATAATGGTTTCTTAGACGTC

AGGTGGCACTTTTCGGGGAAATGTGCGCGGAACCCCTATT

TGTTTATTTTTCTAAATACATTCAAATATGTATCCGCTCA

TGAGACAATAACCCTGATAAATGCTTCAATAATATTGAAA

AAGGAAGAGTATGAGTATTCAACATTTCCGTGTCGCCCTT

ATTCCCTTTTTTGCGGCATTTTGCCTTCCTGTTTTTGCTC

ACCCAGAAACGCTGGTGAAAGTAAAAGATGCTGAAGATCA

GTTGGGTGCACGAGTGGGTTACATCGAACTGGATCTCAAC

AGCGGTAAGATCCTTGAGAGTTTTCGCCCCGAAGAACGTT

TTCCAATGATGAGCACTTTTAAAGTTCTGCTATGTGGCGC

GGTATTATCCCGTATTGACGCCGGGCAAGAGCAACTCGGT

CGCCGCATACACTATTCTCAGAATGACTTGGTTGAGTACT

CACCAGTCACAGAAAAGCATCTTACGGATGGCATGACAGT

AAGAGAATTATGCAGTGCTGCCATAACCATGAGTGATAAC

ACTGCGGCCAACTTACTTCTGACAACGATCGGAGGACCGA

AGGAGCTAACCGCTTTTTTGCACAACATGGGGGATCATGT

AACTCGCCTTGATCGTTGGGAACCGGAGCTGAATGAAGCC

ATACCAAACGACGAGCGTGACACCACGATGCCTGTAGCAA

TGGCAACAACGTTGCGCAAACTATTAACTGGCGAACTACT

TACTCTAGCTTCCCGGCAACAATTAATAGACTGGATGGAG

GCGGATAAAGTTGCAGGACCACTTCTGCGCTCGGCCCTTC

CGGCTGGCTGGTTTATTGCTGATAAATCTGGAGCCGGTGA

GCGTGGGTCTCGCGGTATCATTGCAGCACTGGGGCCAGAT

GGTAAGCCCTCCCGTATCGTAGTTATCTACACGACGGGGA

GTCAGGCAACTATGGATGAACGAAATAGACAGATCGCTGA

GATAGGTGCCTCACTGATTAAGCATTGGTAACTGTCAGAC

CAAGTTTACTCATATATACTTTAGATTGATTTAAAACTTC

ATTTTTAATTTAAAAGGATCTAGGTGAAGATCCTTTTTGA

TAATCTCATGACCAAAATCCCTTAACGTGAGTTTTCGTTC

CACTGAGCGTCAGACCCCGTAGAAAAGATCAAAGGATCTT

CTTGAGATCCTTTTTTTCTGCGCGTAATCTGCTGCTTGCA

AACAAAAAAACCACCGCTACCAGCGGTGGTTTGTTTGCCG

GATCAAGAGCTACCAACTCTTTTTCCGAAGGTAACTGGCT

TCAGCAGAGCGCAGATACCAAATACTGTCCTTCTAGTGTA

GCCGTAGTTAGGCCACCACTTCAAGAACTCTGTAGCACCG

CCTACATACCTCGCTCTGCTAATCCTGTTACCAGTGGCTG

CTGCCAGTGGCGATAAGTCGTGTCTTACCGGGTTGGACTC

AAGACGATAGTTACCGGATAAGGCGCAGCGGTCGGGCTGA

ACGGGGGGTTCGTGCACACAGCCCAGCTTGGAGCGAACGA

CCTACACCGAACTGAGATACCTACAGCGTGAGCTATGAGA

AAGCGCCACGCTTCCCGAAGGGAGAAAGGCGGACAGGTAT

CCGGTAAGCGGCAGGGTCGGAACAGGAGAGCGCACGAGGG

AGCTTCCAGGGGGAAACGCCTGGTATCTTTATAGTCCTGT

CGGGTTTCGCCACCTCTGACTTGAGCGTCGATTTTTGTGA

TGCTCGTCAGGGGGCGGAGCCTATGGAAAAACGCCAGCA

ACGCGGCCTTTTTACGGTTCCTGGCCTTTTGCTGGCCTTT

TGCTCACATGT

In one preferred embodiment, the second vector (helper phage with RGD sequence) comprises a nucleic acid sequence substantially as set out in SEQ ID No: 10, or a fragment or variant thereof, wherein SEQ ID No: 10 is represented as follows:

[SEQ ID No: 10]

AACGCTACTACTATTAGTAGAATTGATGCCACCTTTTCAG
CTCGCGCCCCAAATGAAAATATAGCTAAACAGGTTATTGA
CCATTTGCGAAATGTATCTAATGGTCAAACTAAATCTACT
CGTTCGCAGAATTGGGAATCAACTGTTACATGGAATGAAA
CTTCCAGACACCGTACTTTAGTTGCATATTTAAAACATGT
TGAGCTACAGCACCAGATTCAGCAATTAAGCTCTAAGCCA
TCCGCAAAAATGACCTCTTATCAAAGGAGCAATTAAAGG
TACTCTCTAATCCTGACCTGTTGGAGTTTGCTTCCGGTCT
GGTTCGCTTTGAAGCTCGAATTAAAACGCGATATTTGAAG
TCTTTCGGGCTTCCTCTTAATCTTTTTGATGCAATCCGCT
TTGCTTCTGACTATAATAGTCAGGGTAAAGACCTGATTTT
TGATTTATGGTCATTCTCGTTTTCTGAACTGTTTAAAGCA
TTTGAGGGGATTCAATGAATATTTATGACGATTCCGCAG
TATTGGACGCTATCCAGTCTAAACATTTTACTATTACCCC
CTCTGGCAAAACTTCTTTTGCAAAAGCCTCTCGCTATTTT
GGTTTTTATCGTCGTCTGGTAAACGAGGGTTATGATAGTG
TTGCTCTTACTATGCCTCGTAATTCCTTTTGGCGTTATGT
ATCTGCATTAGTTGAATGTGGTATTCCTAAATCTCAACTG
ATGAATCTTTCTACCTGTAATAATGTTGTTCCGTTAGTTC
GTTTTATTAACGTAGATTTTTCTTCCCAACGTCCTGACTG
GTATAATGAGCCAGTTCTTAAAATCGCATAAGGTAATTCA
CAATGATTAAAGTTGAAATTAAACCATCTCAAGCCCAATT
TACTACTCGTTCTGGTGTTTCTCGTCAGGGCAAGCCTTAT
TCACTGAATGAGCAGCTTTGTTACGTTGATTTGGGTAATG
AATATCCGGTTCTTGTCAAGATTACTCTTGATGAAGGTCA
GCCAGCCTATGCGCCTGGTCTGTACACCGTTCATCTGTCC
TCTTTCAAAGTTGGTCAGTTCGGTTCCCTTATGATTGACC
GTCTGCGCCTCGTTCCGGCTAAGTAACATGGAGCAGGTCG
CGGATTTCGACACAATTTATCAGGCGATGATACAAATCTC
CGTTGTACTTTGTTTCGCGCTTGGTATAATCGCTGGGGGT
CAAAGATGAGTGTTTAGTGTATTCTTTCGCCTCTTTCGT
TTTAGGTTGGTGCCTTCGTAGTGGCATTACGTATTTTACC
CGTTTAATGGAAACTTCCTCATGAAAAGTCTTTAGTCCT
CAAAGCCTCTGTAGCCGTTGCTACCCTCGTTCCGATGCTG
TCTTTCGCTGCTGAGGGTGACGATCCCGCAAAAGCGGCCT
TTAACTCCCTGCAAGCCTCAGCGACCGAATATATCGGTTA
TGCGTGGGCGATGGTTGTTGTCATTGTCGGCGCAACTATC
GGTATCAAGCTGTTTAAGAAATTCACCTCGAAAGCAAGCT
GATAAACCGATACAATTAAAGGCTCCTTTTGGAGCCTTTT
TTTTTGGAGATTTTCAACGTGAAAAAATTATTATTCGCAA

TTCCTTTAGTTGTTCCTTTCTATTCTCACTCCGCTTGTGA
TTGTAGGGGGGATTGTTTTTGTGAAACTGTTGAAAGTTGT
TTAGCAAAACCCCATACAGAAAATTCATTTACTAACGTCT
GGAAAGACGACAAAACTTTAGATCGTTACGCTAACTATGA
GGGTTGTCTGTGGAATGCTACAGGCGTTGTAGTTTGTACT
GGTGACGAAACTCAGTGTTACGGTACATGGGTTCCTATTG
GGCTTGCTATCCCTGAAAATGAGGGTGGTGGCTCTGAGGG
TGGCGGTTCTGAGGGTGGCGGTTCTGAGGGTGGCGGTACT
AAACCTCCTGAGTACGGTGATACACCTATTCCGGGCTATA
CTTATATCAACCCTCTCGACGGCACTTATCCGCCTGGTAC
TGAGCAAAACCCCGCTAATCCTAATCCTTCTCTTGAGGAG
TCTCAGCCTCTTAATACTTTCATGTTTCAGAATAATAGGT
TCCGAAATAGGCAGGGGGCATTAACTGTTTATACGGGCAC
TGTTACTCAAGGCACTGACCCCGTTAAAACTTATTACCAG
TACACTCCTGTATCATCAAAAGCCATGTATGACGCTTACT
GGAACGGTAAATTCAGAGACTGCGCTTTCCATTCTGGCTT
TAATGAGGATCCATTCGTTTGTGAATATCAAGGCCAATCG
TCTGACCTGCCTCAACCTCCTGTCAATGCTGGCGGCGGCT
CTGGTGGTGGTTCTGGTGGCGGCTCTGAGGGTGGTGGCTC
TGAGGGTGGCGGTTCTGAGGGTGGCGGCTCTGAGGGAGGC
GGTTCCGGTGGTGGCTCTGGTTCCGGTGATTTTGATTATG
AAAAGATGGCAAACGCTAATAAGGGGGCTATGACCGAAAA
TGCCGATGAAAACGCGCTACAGTCTGACGCTAAAGGCAAA
CTTGATTCTGTCGCTACTGATTACGGTGCTGCTATCGATG
GTTTCATTGGTGACGTTTCCGGCCTTGCTAATGGTAATGG
TGCTACTGGTGATTTTGCTGGCTCTAATTCCCAAATGGCT
CAAGTCGGTGACGGTGATAATTCACCTTTAATGAATAATT
TCCGTCAATATTTACCTTCCCTCCCTCAATCGGTTGAATG
TCGCCCTTTTGTCTTTAGCGCTGGTAAACCATATGAATTT
TCTATTGATTGTGACAAAATAAACTTATTCCGTGGTGTCT
TTGCGTTTCTTTTATATGTTGCCACCTTTATGTATGTATT
TTCTACGTTTGCTAACATACTGCGTAATAAGGAGTCTTAA
TCATGCCAGTTCTTTTGGGTATTCCGTTATTATTGCGTTT
CCTCGGTTTCCTTCTGGTAACTTTGTTCGGCTATCTGCTT
ACTTTTCTTAAAAAGGGCTTCGGTAAGATAGCTATTGCTA
TTTCATTGTTTCTTGCTCTTATTATTGGGCTTAACTCAAT
TCTTGTGGGTTATCTCTCTGATATTAGCGCTCAATTACCC
TCTGACTTTGTTCAGGGTGTTCAGTTAATTCTCCCGTCTA
ATGCGCTTCCCTGTTTTTATGTTATTCTCTCTGTAAAGGC
TGCTATTTTCATTTTTGACGTTAAACAAAAAATCGTTTCT
TATTTGGATTGGGATAAATAATATGGCTGTTTATTTTGTA

-continued

ACTGGCAAATTAGGCTCTGGAAAGACGCTCGTTAGCGTTG
GTAAGATTCAGGATAAAATTGTAGCTGGGTGCAAAATAGC
AACTAATCTTGATTTAAGGCTTCAAAACCTCCCGCAAGTC
GGGAGGTTCGCTAAAACGCCTCGCGTTCTTAGAATACCGG
ATAAGCCTTCTATATCTGATTTGCTTGCTATTGGGCGCGG
TAATGATTCCTACGATGAAAATAAAAACGGCTTGCTTGTT
CTCGATGAGTGCGGTACTTGGTTTAATACCCGTTCTTGGA
ATGATAAGGAAAGACAGCCGATTATTGATTGGTTTCTACA
TGCTCGTAAATTAGGATGGGATATTATTTTTCTTGTTCAG
GACTTATCTATTGTTGATAAACAGGCGCGTTCTGCATTAG
CTGAACATGTTGTTTATTGTCGTCGTCTGGACAGAATTAC
TTTACCTTTTGTCGGTACTTTATATTCTCTTATTACTGGC
TCGAAAATGCCTCTGCCTAAATTACATGTTGGCGTTGTTA
AATATGGCGATTCTCAATTAAGCCCTACTGTTGAGCGTTG
GCTTTATACTGGTAAGAATTTGTATAACGCATATGATACT
AAACAGGCTTTTTCTAGTAATTATGATTCCGGTGTTTATT
CTTATTTAACGCCTTATTTATCACACGGTCGGTATTTCAA
ACCATTAAATTTAGGTCAGAAGATGAAATTAACTAAAATA
TATTTGAAAAGTTTTCTCGCGTTCTTTGTCTTGCGATTG
GATTTGCATCAGCATTTACATATAGTTATATAACCCAACC
TAAGCCGGAGGTTAAAAAGGTAGTCTCTCAGACCTATGAT
TTTGATAAATTCACTATTGACTCTTCTCAGCGTCTTAATC
TAAGCTATCGCTATGTTTTCAAGGATTCTAAGGGAAAATT
AATTAATAGCGACGATTTACAGAAGCAAGGTTATTCACTC
ACATATATTGATTTATGTACTGTTTCCATTAAAAAAGGTA
ATTCAAATGAAATTGTTAAATGTAATTAATTTTGTTTTCT
TGATGTTTGTTTCATCATCTTCTTTTGCTCAGGTAATTGA
AATGAATAATTCGCCTCTGCGCGATTTTGTAACTTGGTAT
TCAAAGCAATCAGGCGAATCCGTTATTGTTTCTCCCGATG
TAAAAGGTACTGTTACTGTATATTCATCTGACGTTAAACC
TGAAAATCTACGCAATTTCTTTATTTCTGTTTTACGTGCT
AATAATTTTGATATGGTTGGTTCAATTCCTTCCATAATTC
AGAAGTATAATCCAAACAATCAGGATTATATTGATGAATT
GCCATCATCTGATAATCAGGAATATGATGATAATTCCGCT
CCTTCTGGTGGTTTCTTTGTTCCGCAAAATGATAATGTTA
CTCAAACTTTTAAAATTAATAACGTTCGGGCAAAGGATTT
AATACGAGTTGTCGAATTGTTTGTAAAGTCTAATACTTCT
AAATCCTCAAATGTATTATCTATTGACGGCTCTAATCTAT
TAGTTGTTAGTGCACCTAAAGATATTTTAGATAACCTTCC
TCAATTCCTTTCTACTGTTGATTTGCCAACTGACCAGATA

-continued

TTGATTGAGGGTTTGATATTTGAGGTTCAGCAAGGTGATG
CTTTAGATTTTTCATTTGCTGCTGGCTCTCAGCGTGGCAC
TGTTGCAGGCGGTGTTAATACTGACCGCCTCACCTCTGTT
TTATCTTCTGCTGGTGGTTCGTTCGGTATTTTTAATGGCG
ATGTTTTAGGGCTATCAGTTCGCGCATTAAAGACTAATAG
CCATTCAAAAATATTGTCTGTGCCACGTATTCTTACGCTT
TCAGGTCAGAAGGGTTCTATCTCTGTTGGCCAGAATGTCC
CTTTTATTACTGGTCGTGTGACTGGTGAATCTGCCAATGT
AAATAATCCATTTCAGACGATTGAGCGTCAAAATGTAGGT
ATTTCCATGAGCGTTTTTCCTGTTGCAATGGCTGGCGGTA
ATATTGTTCTGGATATTACCAGCAAGGCCGATAGTTTGAG
TTCTTCTACTCAGGCAAGTGATGTTATTACTAATCAAAGA
AGTATTGCTACAACGGTTAATTTGCGTGATGGACAGACTC
TTTTACTCGGTGGCCTCACTGATTATAAAAACACTTCTCA
AGATTCTGGCGTACCGTTCCTGTCTAAAATCCCTTTAATC
GGCCTCCTGTTTAGCTCCCGCTCTGATTCCAACGAGGAAA
GCACGTTATACGTGCTCGTCAAAGCAACCATAGTACGCGC
CCTGTAGCGGCGCATTAAGCGCGGCGGGTGTGGTGGTTAC
GCGCAGCGTGACCGCTACACTTGCCAGCGCCCTAGCGCCC
GCTCCTTTCGCTTTCTTCCCTTCCTTTCTCGCCACGTTCG
CCGGCTTTCCCCGTCAAGCTCTAAATCGGGGGCTCCCTTT
AGGGTTCCGATTTAGTGCTTTACGGCACCTCGACCCCAAA
AAACTTGATTTGGGTGATGGTTCACGTAGTGGGCCATCGC
CCTGATAGACGGTTTTTCGCCCTTTGACGTTGGAGTCCAC
GTTCTTTAATAGTGGACTCTTGTTCCAAACTGGAACAACA
CTCAACCCTATCTCGGGACGGATCGCTTCATGTGGCAGGA
GAAAAAGGCTGCACCGGTGCGTCAGCAGAATATGTGATA
CAGGATATATTCCGCTTCCTCGCTCACTGACTCGCTACGC
TCGGTCGTTCGACTGCGGCGAGCGGAAATGGCTTACGAAC
GGGGCGGAGATTTCCTGGAAGATGCCAGGAAGATACTTAA
CAGGGAAGTGAGAGGGCCGCGGCAAAGCCGTTTTTCCATA
GGCTCCGCCCCCTGACAAGCATCACGAAATCTGACGCTC
AAATCAGTGGTGGCGAAACCCGACAGGACTATAAAGATAC
CAGGCGTTTCCCCCTGGCGGCTCCCTCGTGCGCTCTCCTG
TTCCTGCCTTTCGGTTTACCGGTGTCATTCCGCTGTTATG
GCCGCGTTTGTCTCATTCCACGCCTGACACTCAGTTCCGG
GTAGGCAGTTCGCTCCAAGCTGGACTGTATGCACGAACCC
CCCGTTCAGTCCGACCGCTGCGCCTTATCCGGTAACTATC
GTCTTGAGTCCAACCCGGAAAGACATGCAAAAGCACCACT
GGCAGCAGCCACTGGTAATTGATTTAGAGGAGTTAGTCTT
GAAGTCATGCGCCGGTTAAGGCTAAACTGAAAGGACAAGT

TTTGGTGACTGCGCTCCTCCAAGCCAGTTACCTCGGTTCA

AAGAGTTGGTAGCTCAGAGAACCTTCGAAAAACCGCCCTG

CAAGGCGGTTTTTTCGTTTTCAGAGCAAGAGATTACGCGC

AGACCAAAACGATCTCAAGAAGATCATCTTATTAAGGGGT

CTGACGCTCAGTGGAACGAAAACTCACGTTAAGGGATTTT

GGTCATGAGATTATCAAAAGGATCTTCACCTAGATCCTT

TTAAATTAAAAATGAAGTTTTAAATCAATCTAAAGTATAT

ATGAGTAAACTTGGTCTGACAGTTACCAATGCTTAATCAG

TGAGGCACCTATCTCAGCGATCTGTCTATTTCGTTCATCC

ATAGTTGCCTGACTCCCCGTCGTGTAGATAACTACGATAC

GGGAGGGCTTACCATCTGGCCCCAGTGCTGCAATGATACC

GCGAGACCCACGCTCACCGGCTCCAGATTTATCAGCAATA

AACCAGCCAGCCGATTCGAGCTCGCCCCGGGGATCGACCA

GTTGGTGATTTTGAACTTTTGCTTTGCCACGGAACGGTCT

GCGTTGTCGGGAAGATGCGTGATCTGATCCTTCAACTCAG

CAAAAGTTCGATTTATTCAACAAAGCCGCCGTCCCGTCAA

GTCAGCGTAATGCTCTGCCAGTGTTACAACCAATTAACCA

ATTCTGATTAGAAAAACTCATCGAGCATCAAATGAAACTG

CAATTTATTCATATCAGGATTATCAATACCATATTTTTGA

AAAAGCCGTTTCTGTAATGAAGGAGAAAACTCACCGAGGC

AGTTCCATAGGATGGCAAGATCCTGGTATCGGTCTGCGAT

TCCGACTCGTCAACATCAATACAACCTATTAATTTCCCC

TCGTCAAAAATAAGGTTATCAAGTGAGAAATCACCATGAG

TGACGACTGAATCCGGTGAGAATGGCAAAAGCTTATGCAT

TTCTTTCCAGACTTGTTCAACAGGCCAGCCATTACGCTCG

TCATCAAAATCACTCGCATCAACCAAACCGTTATTCATTC

GTGATTGCGCCTGAGCGAGACGAAATACGCGATCGCTGTT

AAAAGGACAATTACAAACAGGAATCGAATGCAACCGGCGC

AGGAACACTGCCAGCGCATCAACAATATTTTCACCTGAAT

CAGGATATTCTTCTAATACCTGGAATGCTGTTTTCCCGGG

GATCGCAGTGGTGAGTAACCATGCATCATCAGGAGTACGG

ATAAAATGCTTGATGGTCGGAAGAGGCATAAATTCCGTCA

GCCAGTTTAGTCTGACCATCTCATCTGTAACATCATTGGC

AACGCTACCTTTGCCATGTTTCAGAAACAACTCTGGCGCA

TCGGGCTTCCCATACAATCGATAGATTGTCGCACCTGATT

GCCCGACATTATCGCGAGCCCATTTATACCCATATAAATC

AGCATCCATGTTGGAATTTAATCGCGGCCTCGAGCAAGAC

GTTTCCCGTTGAATATGGCTCATAACACCCCTTGTATTAC

TGTTTATGTAAGCAGACAGTTTTATTGTTCATGATGATAT

ATTTTTATCTTGTGCAATGTAACATCAGAGATTTTGAGAC

ACAACGTGGCTTTCCCCCCCCCCCCTGCAGGTCTCGGGC

TATTCTTTTGATTTATAAGGGATTTTGCCGATTTCGGCCT

ATTGGTTAAAAAATGAGCTGATTTAACAAAAATTTAACGC

GAATTTTAACAAAATATTAACGTTTACAATTTAAATATTT

GCTTATACAATCTTCCTGTTTTTGGGGCTTTTCTGATTAT

CAACCGGGGTACATATGATTGACATGCTAGTTTTACGATT

ACCGTTCATCGATTCTCTTGTTTGCTCCAGACTCTCAGGC

AATGACCTGATAGCCTTTGTAGACCTCTCAAAAATAGCTA

CCCTCTCCGGCATGAATTTATCAGCTAGAACGGTTGAATA

TCATATTGATGGTGATTTGACTGTCTCCGGCCTTTCTCAC

CCTTTTGAATCTTTACCTACACATTACTCAGGCATTGCAT

TTAAAATATATGAGGGTTCTAAAAATTTTTATCCTTGCGT

TGAAATAAAGGCTTCTCCCGCAAAAGTATTACAGGGTCAT

AATGTTTTTGGTACAACCGATTTAGCTTTATGCTCTGAGG

CTTTATTGCTTAATTTTGCTAATTCTTTGCCTTGCCTGTA

TGATTTATTGGATGTT

In one preferred embodiment, the second vector (helper phage without RGD sequence) comprises a nucleic acid sequence substantially as set out in SEQ ID No: 11, or a fragment or variant thereof, wherein SEQ ID No: 11 is represented as follows:

[SEQ ID No: 11]
AACGCTACTACTATTAGTAGAATTGATGCCACCTTTTCAG

CTCGCGCCCCAAATGAAAATATAGCTAAACAGGTTATTGA

CCATTTGCGAAATGTATCTAATGGTCAAACTAAATCTACT

CGTTCGCAGAATTGGGAATCAACTGTTACATGGAATGAAA

CTTCCAGACACCGTACTTTAGTTGCATATTTAAAACATGT

TGAGCTACAGCACCAGATTCAGCAATTAAGCTCTAAGCCA

TCCGCAAAAATGACCTCTTATCAAAAGGAGCAATTAAAGG

TACTCTCTAATCCTGACCTGTTGGAGTTTGCTTCCGGTCT

GGTTCGCTTTGAAGCTCGAATTAAAACGCGATATTTGAAG

TCTTTCGGGCTTCCTCTTAATCTTTTTGATGCAATCCGCT

TTGCTTCTGACTATAATAGTCAGGGTAAAGACCTGATTTT

TGATTTATGGTCATTCTCGTTTTCTGAACTGTTTAAAGCA

TTTGAGGGGATTCAATGAATATTTATGACGATTCCGCAG

TATTGGACGCTATCCAGTCTAAACATTTTACTATTACCCC

CTCTGGCAAAACTTCTTTTGCAAAAGCCTCTCGCTATTTT

GGTTTTTATCGTCGTCTGGTAAACGAGGGTTATGATAGTG

TTGCTCTTACTATGCCTCGTAATTCCTTTTGGCGTTATGT

ATCTGCATTAGTTGAATGTGGTATTCCTAAATCTCAACTG

ATGAATCTTTCTACCTGTAATAATGTTGTTCCGTTAGTTC

GTTTTATTAACGTAGATTTTTCTTCCCAACGTCCTGACTG

```
GTATAATGAGCCAGTTCTTAAAATCGCATAAGGTAATTCA
CAATGATTAAAGTTGAAATTAAACCATCTCAAGCCCAATT
TACTACTCGTTCTGGTGTTTCTCGTCAGGGCAAGCCTTAT
TCACTGAATGAGCAGCTTTGTTACGTTGATTTGGGTAATG
AATATCCGGTTCTTGTCAAGATTACTCTTGATGAAGGTCA
GCCAGCCTATGCGCCTGGTCTGTACACCGTTCATCTGTCC
TCTTTCAAAGTTGGTCAGTTCGGTTCCCTTATGATTGACC
GTCTGCGCCTCGTTCCGGCTAAGTAACATGGAGCAGGTCG
CGGATTTCGACACAATTTATCAGGCGATGATACAAATCTC
CGTTGTACTTTGTTTCGCGCTTGGTATAATCGCTGGGGGT
CAAAGATGAGTGTTTTAGTGTATTCTTTCGCCTCTTTCGT
TTTAGGTTGGTGCCTTCGTAGTGGCATTACGTATTTTACC
CGTTTAATGGAAACTTCCTCATGAAAAAGTCTTTAGTCCT
CAAAGCCTCTGTAGCCGTTGCTACCCTCGTTCCGATGCTG
TCTTTCGCTGCTGAGGGTGACGATCCCGCAAAAGCGGCCT
TTAACTCCCTGCAAGCCTCAGCGACCGAATATATCGGTTA
TGCGTGGGCGATGGTTGTTGTCATTGTCGGCGCAACTATC
GGTATCAAGCTGTTTAAGAAATTCACCTCGAAAGCAAGCT
GATAAACCGATACAATTAAAGGCTCCTTTTGGAGCCTTTT
TTTTTGGAGATTTTCAACGTGAAAAAATTATTATTCGCAA
TTCCTTTAGTTGTTCCTTTCTATTCTCACTCCGCTGAAAC
TGTTGAAAGTTGTTTAGCAAAACCCCATACAGAAAATTCA
TTTACTAACGTCTGGAAAGACGACAAAACTTTAGATCGTT
ACGCTAACTATGAGGGTTGTCTGTGGAATGCTACAGGCGT
TGTAGTTTGTACTGGTGACGAAACTCAGTGTTACGGTACA
TGGGTTCCTATTGGGCTTGCTATCCCTGAAAATGAGGGTG
GTGGCTCTGAGGGTGGCGGTTCTGAGGGTGGCGGTTCTGA
GGGTGGCGGTACTAAACCTCCTGAGTACGGTGATACACCT
ATTCCGGGCTATACTTATATCAACCCTCTCGACGGCACTT
ATCCGCCTGGTACTGAGCAAAACCCCGCTAATCCTAATCC
TTCTCTTGAGGAGTCTCAGCCTCTTAATACTTTCATGTTT
CAGAATAATAGGTTCCGAAATAGGCAGGGGCATTAACTG
TTTATACGGGCACTGTTACTCAAGGCACTGACCCCGTTAA
AACTTATTACCAGTACACTCCTGTATCATCAAAAGCCATG
TATGACGCTTACTGGAACGGTAAATTCAGAGACTGCGCTT
TCCATTCTGGCTTTAATGAGGATCCATTCGTTTGTGAATA
TCAAGGCCAATCGTCTGACCTGCCTCAACCTCCTGTCAAT
GCTGGCGGCGGCTCTGGTGGTGGTTCTGGTGGCGGCTCTG
AGGGTGGTGGCTCTGAGGGTGGCGGTTCTGAGGGTGGCGG
CTCTGAGGGAGGCGGTTCCGGTGGTGGCTCTGGTTCCGGT
```

```
GATTTTGATTATGAAAAGATGGCAAACGCTAATAAGGGGG
CTATGACCGAAAATGCCGATGAAAACGCGCTACAGTCTGA
CGCTAAAGGCAAACTTGATTCTGTCGCTACTGATTACGGT
GCTGCTATCGATGGTTTCATTGGTGACGTTTCCGGCCTTG
CTAATGGTAATGGTGCTACTGGTGATTTTGCTGGCTCTAA
TTCCCAAATGGCTCAAGTCGGTGACGGTGATAATTCACCT
TTAATGAATAATTTCCGTCAATATTTACCTTCCCTCCCTC
AATCGGTTGAATGTCGCCCTTTTGTCTTTAGCGCTGGTAA
ACCATATGAATTTTCTATTGATTGTGACAAAATAAACTTA
TTCCGTGGTGTCTTTGCGTTTCTTTTATATGTTGCCACCT
TTATGTATGTATTTTCTACGTTTGCTAACATACTGCGTAA
TAAGGAGTCTTAATCATGCCAGTTCTTTTGGGTATTCCGT
TATTATTGCGTTTCCTCGGTTTCCTTCTGGTAACTTTGTT
CGGCTATCTGCTTACTTTTCTTAAAAAGGGCTTCGGTAAG
ATAGCTATTGCTATTTCATTGTTTCTTGCTCTTATTATTG
GGCTTAACTCAATTCTTGTGGGTTATCTCTCTGATATTAG
CGCTCAATTACCCTCTGACTTTGTTCAGGGTGTTCAGTTA
ATTCTCCCGTCTAATGCGCTTCCCTGTTTTTATGTTATTC
TCTCTGTAAAGGCTGCTATTTTCATTTTTGACGTTAAACA
AAAAATCGTTTCTTATTTGGATTGGGATAAATAATATGGC
TGTTTATTTTGTAACTGGCAAATTAGGCTCTGGAAAGACG
CTCGTTAGCGTTGGTAAGATTCAGGATAAAATTGTAGCTG
GGTGCAAAATAGCAACTAATCTTGATTTAAGGCTTCAAAA
CCTCCCGCAAGTCGGGAGGTTCGCTAAAACGCCTCGCGTT
CTTAGAATACCGGATAAGCCTTCTATATCTGATTTGCTTG
CTATTGGGCGCGGTAATGATTCCTACGATGAAAATAAAAA
CGGCTTGCTTGTTCTCGATGAGTGCGGTACTTGGTTTAAT
ACCCGTTCTTGGAATGATAAGGAAAGACAGCCGATTATTG
ATTGGTTTCTACATGCTCGTAAATTAGGATGGGATATTAT
TTTTCTTGTTCAGGACTTATCTATTGTTGATAAACAGGCG
CGTTCTGCATTAGCTGAACATGTTGTTTATTGTCGTCGTC
TGGACAGAATTACTTTACCTTTTGTCGGTACTTTATATTC
TCTTATTACTGGCTCGAAAATGCCTCTGCCTAAATTACAT
GTTGGCGTTGTAAATATGGCGATTCTCAATTAAGCCCTA
CTGTTGAGCGTTGGCTTTATACTGGTAAGAATTTGTATAA
CGCATATGATACTAAACAGGCTTTTTCTAGTAATTATGAT
TCCGGTGTTTATTCTTATTTAACGCCTTATTTATCACACG
GTCGGTATTTCAAACCATTAAATTTAGGTCAGAAGATGAA
ATTAACTAAAATATATTTGAAAAAGTTTTCTCGCGTTCTT
TGTCTTGCGATTGGATTTGCATCAGCATTTACATATAGTT
ATATAACCCAACCTAAGCCGGAGGTTAAAAAGGTAGTCTC
```

-continued

TCAGACCTATGATTTTGATAAATTCACTATTGACTCTTCT
CAGCGTCTTAATCTAAGCTATCGCTATGTTTTCAAGGATT
CTAAGGGAAAATTAATTAATAGCGACGATTTACAGAAGCA
AGGTTATTCACTCACATATATTGATTTATGTACTGTTTCC
ATTAAAAAAGGTAATTCAAATGAAATTGTTAAATGTAATT
AATTTTGTTTTCTTGATGTTTGTTTCATCATCTTCTTTTG
CTCAGGTAATTGAAATGAATAATTCGCCTCTGCGCGATTT
TGTAACTTGGTATTCAAAGCAATCAGGCGAATCCGTTATT
GTTTCTCCCGATGTAAAAGGTACTGTTACTGTATATTCAT
CTGACGTTAAACCTGAAAATCTACGCAATTTCTTTATTTC
TGTTTTACGTGCTAATAATTTTGATATGGTTGGTTCAATT
CCTTCCATAATTCAGAAGTATAATCCAAACAATCAGGATT
ATATTGATGAATTGCCATCATCTGATAATCAGGAATATGA
TGATAATTCCGCTCCTTCTGGTGGTTTCTTTGTTCCGCAA
AATGATAATGTTACTCAAACTTTTAAAATTAATAACGTTC
GGGCAAAGGATTTAATACGAGTTGTCGAATTGTTTGTAAA
GTCTAATACTTCTAAATCCTCAAATGTATTATCTATTGAC
GGCTCTAATCTATTAGTTGTTAGTGCACCTAAAGATATTT
TAGATAACCTTCCTCAATTCCTTTCTACTGTTGATTTGCC
AACTGACCAGATATTGATTGAGGGTTTGATATTTGAGGTT
CAGCAAGGTGATGCTTTAGATTTTTCATTTGCTGCTGGCT
CTCAGCGTGGCACTGTTGCAGGCGGTGTTAATACTGACCG
CCTCACCTCTGTTTTATCTTCTGCTGGTGGTTCGTTCGGT
ATTTTTAATGGCGATGTTTTAGGGCTATCAGTTCGCGCAT
TAAAGACTAATAGCCATTCAAAAATATTGTCTGTGCCACG
TATTCTTACGCTTTCAGGTCAGAAGGGTTCTATCTCTGTT
GGCCAGAATGTCCCTTTTATTACTGGTCGTGTGACTGGTG
AATCTGCCAATGTAAATAATCCATTTCAGACGATTGAGCG
TCAAAATGTAGGTATTTCCATGAGCGTTTTTCCTGTTGCA
ATGGCTGGCGGTAATATTGTTCTGGATATTACCAGCAAGG
CCGATAGTTTGAGTTCTTCTACTCAGGCAAGTGATGTTAT
TACTAATCAAAGAAGTATTGCTACAACGGTTAATTTGCGT
GATGGACAGACTCTTTTACTCGGTGGCCTCACTGATTATA
AAAACACTTCTCAAGATTCTGGCGTACCGTTCCTGTCTAA
AATCCCTTTAATCGGCCTCCTGTTTAGCTCCCGCTCTGAT
TCCAACGAGGAAAGCACGTTATACGTGCTCGTCAAAGCAA
CCATAGTACGCGCCCTGTAGCGGCGCATTAAGCGCGGCGG
GTGTGGTGGTTACGCGCAGCGTGACCGCTACACTTGCCAG
CGCCCTAGCGCCCGCTCCTTTCGCTTTCTTCCCTTCCTTT
CTCGCCACGTTCGCCGGCTTTCCCCGTCAAGCTCTAAATC

-continued

GGGGGCTCCCTTTAGGGTTCCGATTTAGTGCTTTACGGCA
CCTCGACCCCAAAAAACTTGATTTGGGTGATGGTTCACGT
AGTGGGCCATCGCCCTGATAGACGGTTTTTCGCCCTTTGA
CGTTGGAGTCCACGTTCTTTAATAGTGGACTCTTGTTCCA
AACTGGAACAACACTCAACCCTATCTCGGGACGGATCGCT
TCATGTGGCAGGAGAAAAAGGCTGCACCGGTGCGTCAGC
AGAATATGTGATACAGGATATATTCCGCTTCCTCGCTCAC
TGACTCGCTACGCTCGGTCGTTCGACTGCGGCGAGCGGAA
ATGGCTTACGAACGGGGCGGAGATTTCCTGGAAGATGCCA
GGAAGATACTTAACAGGGAAGTGAGAGGGCCGCGGCAAAG
CCGTTTTTCCATAGGCTCCGCCCCCCTGACAAGCATCACG
AAATCTGACGCTCAAATCAGTGGTGGCGAAACCCGACAGG
ACTATAAAGATACCAGGCGTTTCCCCCTGGCGGCTCCCTC
GTGCGCTCTCCTGTTCCTGCCTTTCGGTTTACCGGTGTCA
TTCCGCTGTTATGGCCGCGTTTGTCTCATTCCACGCCTGA
CACTCAGTTCCGGGTAGGCAGTTCGCTCCAAGCTGGACTG
TATGCACGAACCCCCCGTTCAGTCCGACCGCTGCGCCTTA
TCCGGTAACTATCGTCTTGAGTCCAACCCGGAAAGACATG
CAAAAGCACCACTGGCAGCAGCCACTGGTAATTGATTTAG
AGGAGTTAGTCTTGAAGTCATGCGCCGGTTAAGGCTAAAC
TGAAAGGACAAGTTTTGGTGACTGCGCTCCTCCAAGCCAG
TTACCTCGGTTCAAAGAGTTGGTAGCTCAGAGAACCTTCG
AAAAACCGCCCTGCAAGGCGGTTTTTTCGTTTTCAGAGCA
AGAGATTACGCGCAGACCAAAACGATCTCAAGAAGATCAT
CTTATTAAGGGGTCTGACGCTCAGTGGAACGAAAACTCAC
GTTAAGGGATTTTGGTCATGAGATTATCAAAAAGGATCTT
CACCTAGATCCTTTTAAATTAAAAATGAAGTTTTAAATCA
ATCTAAAGTATATATGAGTAAACTTGGTCTGACAGTTACC
AATGCTTAATCAGTGAGGCACCTATCTCAGCGATCTGTCT
ATTTCGTTCATCCATAGTTGCCTGACTCCCCGTCGTGTAG
ATAACTACGATACGGGAGGGCTTACCATCTGGCCCCAGTG
CTGCAATGATACCGCGAGACCCACGCTCACCGGCTCCAGA
TTTATCAGCAATAAACCAGCCAGCCGATTCGAGCTCGCCC
CGGGGATCGACCAGTTGGTGATTTTGAACTTTTGCTTTGC
CACGGAACGGTCTGCGTTGTCGGGAAGATGCGTGATCTGA
TCCTTCAACTCAGCAAAAGTTCGATTTATTCAACAAAGCC
GCCGTCCCGTCAAGTCAGCGTAATGCTCTGCCAGTGTTAC
AACCAATTAACCAATTCTGATTAGAAAAACTCATCGAGCA
TCAAATGAAACTGCAATTTATTCATATCAGGATTATCAAT
ACCATATTTTTGAAAAAGCCGTTTCTGTAATGAAGGAGAA
AACTCACCGAGGCAGTTCCATAGGATGGCAAGATCCTGGT

-continued

```
ATCGGTCTGCGATTCCGACTCGTCCAACATCAATACAACC

TATTAATTTCCCCTCGTCAAAAATAAGGTTATCAAGTGAG

AAATCACCATGAGTGACGACTGAATCCGGTGAGAATGGCA

AAAGCTTATGCATTTCTTTCCAGACTTGTTCAACAGGCCA

GCCATTACGCTCGTCATCAAAATCACTCGCATCAACCAAA

CCGTTATTCATTCGTGATTGCGCCTGAGCGAGACGAAATA

CGCGATCGCTGTTAAAAGGACAATTACAAACAGGAATCGA

ATGCAACCGGCGCAGGAACACTGCCAGCGCATCAACAATA

TTTTCACCTGAATCAGGATATTCTTCTAATACCTGGAATG

CTGTTTTCCCGGGGATCGCAGTGGTGAGTAACCATGCATC

ATCAGGAGTACGGATAAAATGCTTGATGGTCGGAAGAGGC

ATAAATTCCGTCAGCCAGTTTAGTCTGACCATCTCATCTG

TAACATCATTGGCAACGCTACCTTTGCCATGTTTCAGAAA

CAACTCTGGCGCATCGGGCTTCCCATACAATCGATAGATT

GTCGCACCTGATTGCCCGACATTATCGCGAGCCCATTTAT

ACCCATATAAATCAGCATCCATGTTGGAATTTAATCGCGG

CCTCGAGCAAGACGTTTCCCGTTGAATATGGCTCATAACA

CCCCTTGTATTACTGTTTATGTAAGCAGACAGTTTTATTG

TTCATGATGATATATTTTTATCTTGTGCAATGTAACATCA

GAGATTTTGAGACACAACGTGGCTTTCCCCCCCCCCCCCT

GCAGGTCTCGGGCTATTCTTTTGATTTATAAGGGATTTTG

CCGATTTCGGCCTATTGGTTAAAAAATGAGCTGATTTAAC

AAAAATTTAACGCGAATTTTAACAAAATATTAACGTTTAC

AATTTAAATATTTGCTTATACAATCTTCCTGTTTTTGGGG

CTTTTCTGATTATCAACCGGGGTACATATGATTGACATGC

TAGTTTTACGATTACCGTTCATCGATTCTCTTGTTTGCTC

CAGACTCTCAGGCAATGACCTGATAGCCTTTGTAGACCTC

TCAAAAATAGCTACCCTCTCCGGCATGAATTTATCAGCTA

GAACGGTTGAATATCATATTGATGGTGATTTGACTGTCTC

CGGCCTTTCTCACCCTTTTGAATCTTTACCTACACATTAC

TCAGGCATTGCATTTAAAATATATGAGGGTTCTAAAAATT

TTTATCCTTGCGTTGAAATAAAGGCTTCTCCCGCAAAAGT

ATTACAGGGTCATAATGTTTTTGGTACAACCGATTTAGCT

TTATGCTCTGAGGCTTTATTGCTTAATTTTGCTAATTCTT

TGCCTTGCCTGTATGATTTATTGGATGTT
```

As described in Example 1, the inventors have devised two alternative approaches (see FIGS. 9 and 10) for producing the recombinant phagemid particle of the invention in a prokaryotic host.

Hence, in a third aspect, there is provided a method for producing a recombinant phagemid particle from a prokaryotic host, the method comprising:—
(i) introducing, into a prokaryotic host cell, a first vector configured to persist inside the prokaryotic host, and comprising at least one transgene expression cassette, and a packaging signal for enabling replication of the vector into single-stranded DNA;
(ii) introducing, into the host, a helper phage comprising nucleic acid encoding bacteriophage structural proteins; and
(iii) culturing the host under conditions which result in the single-stranded DNA being packaged by the structural proteins to form and extrude a recombinant phagemid particle from the prokaryotic host.

Advantageously, this embodiment (as shown in FIG. 9) results in very high yields of particles. The first vector (i.e. the phagemid particle's genome) may be introduced into the host cell, for example by infection. The host cell may then be transformed with the helper phage, which results in the production of the recombinant phagemid particle. Preferably, the method comprises a purification step following the culturing step.

Purification may comprise centrifugation and/or filtration.

In a fourth aspect, there is provided a method for producing a recombinant phagemid particle from a prokaryotic host, the method comprising:—
(i) introducing into a prokaryotic host cell: (a) a first vector configured to persist inside the prokaryotic host, and comprising at least one transgene expression cassette, and a packaging signal for enabling replication of the vector into single-stranded DNA, and (b) a second vector comprising nucleic acid encoding structural proteins required for packaging the single-stranded DNA; and
(ii) culturing the host under conditions which result in the single-stranded DNA being packaged by the structural proteins to form and extrude a recombinant phagemid particle from the prokaryotic host.

Advantageously, this embodiment (as shown in FIG. 10) results in improved safety. The second vector (i.e. the helper phage) may be introduced into the host cell, for example by infection. The host cell may then be transformed with the first vector (i.e. the phagemid particle's genome), which results in the production of the recombinant phagemid particle. Preferably, the method comprises a purification step following the culturing step. Purification may comprise centrifugation and/or filtration.

In a fifth aspect, there is provided use of a helper phage comprising nucleic acid encoding viral vector structural proteins to produce the recombinant phagemid particle according to the first aspect from a prokaryotic host.

In a sixth aspect, there is provided a host cell comprising the first and/or second vector as defined in the second aspect.

The host cell is preferably prokaryotic, more preferably a bacterial cell. Examples of suitable host cells include: (i) TG1 (Genotype: K-12 supE thi-1Δ(lac-proAB) Δ(mcrB-hsdSM)5, ($r_K^-$-$m_K^-$), Plasmids: F' [traD36 proAB$^+$lacI$^q$ lacZΔM15]), (ii) DH5αF'IQ™ (Genotype: F-φ80lacZΔM15 Δ(lacZYA-argF) U169 recA1 endA1 hsdR17 (rk−, mk+) phoA supE44λ-thi-1 gyrA96 relA1, Plasmids: F' proAB+ lacIqZΔM15 zzf::Tn5 [KmR]; and (iii) XL1-Blue MRF' (Genotype: Δ(mcrA)183 Δ(mcrCB-hsdSMR-mrr)173 endA1 supE44 thi-1 recA1 gyrA96 relA1 lac, Plasmids: F' proAB lacIqZΔM15 Tn10 (Tetr).

In another aspect, there is provided the recombinant phagemid particle according to the first aspect, or the system according to the second aspect, for use as an experimental research tool.

For example, the particle or system can be used ex vivo or in vitro.

Preferably, however, the particle is used therapeutically or in diagnostic methods, preferably in vivo.

Thus, in a seventh aspect, there is provided the recombinant phagemid particle according to the first aspect, or the system according to the second aspect, for use in therapy or diagnosis.

The invention may be used for the treatment of a wide variety of diseases due to the target-specific nature and the improved transduction efficiency of the recombinant phagemid particle of the invention. Consequently, the therapeutic opportunities of recombinant bacteriophages used in gene therapy may be significantly increased by the invention due to its ability to carry one or more transgene expression cassettes. The invention may be used prophylactically to prevent disease, or after the development of a disease, to ameliorate and/or treat it.

Hence, in an eighth aspect, there is provided recombinant phagemid particle according to the first aspect, or the system according to the second aspect, for use in a gene therapy technique.

In a ninth aspect, there is provided a method of treating, preventing or ameliorating a disease in a subject using a gene therapy technique, the method comprising administering, to a subject in need of such treatment, a therapeutically effective amount of the recombinant phagemid particle according to the first aspect or the system according to the second aspect.

It will be appreciated that the invention may be used to create a variety of different recombinant phagemid particles that can be used for the treatment and/or diagnosis of a variety of diseases depending on the nature of the particles and the displayed foreign proteins. For example, in an embodiment where the recombinant phagemid particle comprises a tumor-targeting ligand and/or which comprises a transgene expressing an anti-tumor gene (e.g. the HSVtk gene), then it may be used to treat cancer. The target cell in the gene therapy technique is preferably eukaryotic, and preferably mammalian.

The gene therapy technique therefore is preferably used to treat, prevent or ameliorate cancer. Tumours may be in the brain, e.g. medulloblastoma, or diffuse intrinsic pontine glioma (DIPG). The recombinant phagemid particle may be used in combination with conventional treatments, such as chemotherapeutic drugs (i.e. doxorubicin, temozolomide, lomustine), radiation therapy, or other drugs/xenobiotic compound, including but not limited to inhibitors of histone deacetylases (HDAC inhibitors), proteasome inhibiting drugs and anticancer products from natural and dietary sources (i.e. genistein).

The inventors believe that the recombinant phagemid particle of the invention will have a significant commercial value in the delivery of peptide and/or DNA and/or adjuvant vaccines.

Thus, in a tenth aspect, there is provided a vaccine comprising the recombinant phagemid viral particle according to the first aspect or the system according to the second aspect.

In an eleventh aspect, there is provided the recombinant phagemid viral particle according to the first aspect, or the system according to the second aspect, for use in vaccine delivery to a subject.

Preferably, the vaccine is a peptide vaccine. The vaccine is preferably a DNA vaccine. The vaccine preferably comprises a suitable adjuvant. In an embodiment, the recombinant phagemid particle may be used to carry a transgene or DNA cassette encoding an antigen to stimulate the body's immune system. The recombinant phagemid particle may also be used to directly display and express the antigen of interest on the major pVIII coat proteins, thus providing an efficient platform for the simultaneous delivery, by a single phage particle, of numerous antigens as vaccine DNA vaccines, or proteins, or adjuvants readily expressed on the phage surface. The subject may be mammalian, and is preferably human.

In a twelfth aspect, therefore, there is provided the recombinant phagemid particle according to the first aspect, or the system according to the second aspect, for use in delivering and targeting a foreign antigen to a tumour in a vaccinated subject. Animals will first be vaccinated against foreign antigens, or already vaccinated against the antigen used, then the tumour-targeted phagemid will be administered to the vaccinated animals to deliver the foreign antigens to tumours, in order to induce an immune attack against these tumours.

The inventors also believe that the recombinant phagemid particle of the invention can also be used in a variety of different genetic-molecular imaging techniques, such as positron emission tomography (PET), Ultrasound (US), SPECT imaging, functional magnetic resonance imaging, or bioluminescence imaging.

Hence, in a thirteenth aspect, there is provided use of the recombinant phagemid particle according to the first aspect, or the system according to the second aspect, in a genetic-molecular imaging technique.

The transgene harboured by the phagemid particle may encode HSVtk and/or the sodium/iodide symporter (NIS), and the particle is preferably used in combination with a radiolabelled substrate. For example, the human sodium/iodide symporter (NIS) imaging gene is preferably used in combination with $I^{124}$ for clinically applicable positron emission tomography (PET) imaging, or with $I^{125/99m}Tc$-pertechnetate for clinically applicable SPECT imaging.

Alternatively, the HSVtk gene is preferably used in combination with radiolabeled nucleoside analogues such as the 20-[18F]-fluoro-20-deoxy-1-b-D-arabino-furanosyl-5-ethyluracil ([18F]FEAU).

It will be appreciated that the recombinant phagemid particles and systems according to the invention (i.e. referred to hereinafter as "agents") may be used in a medicament which may be used in a monotherapy, or as an adjunct to, or in combination with, known therapies for treating, ameliorating, or preventing disease, such as cancer. For example, a combined therapeutic approach using the phagemid particles and systems of the invention with existing chemotherapeutics, such as Temozolamide, Doxorubicin or Genistein, is preferred.

In another preferred embodiment, therapy may comprise the combination of the recombinant phagemid particle and system of the invention with an extracellular matrix degrading agent, such as enzyme or losartan. The inventors believe that extracellular matrix degrading agents should enhance phagemid diffusion in the subject being treated, and especially within a solid tumour.

The agents according to the invention (i.e. the recombinant phagemid particle of the first aspect, or the system according to the second aspect) may be combined in compositions having a number of different forms depending, in particular, on the manner in which the composition is to be used. Thus, for example, the composition may be in the form of a powder, tablet, capsule, liquid etc. or any other suitable form that may be administered to a person or animal in need of treatment. It will be appreciated that the vehicle of medicaments according to the invention should be one which is well-tolerated by the subject to whom it is given.

Medicaments comprising the agents according to the invention may be used in a number of ways. For instance, oral administration may be required, in which case the agents may be contained within a composition that may, for example, be ingested orally in the form of a tablet, capsule or liquid. Compositions comprising agents of the invention may be administered by inhalation (e.g. intranasally). Compositions may also be formulated for topical use. For instance, creams or ointments may be applied to the skin.

Agents according to the invention may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with agents used according to the invention is required and which would normally require frequent administration (e.g. at least daily injection).

In a preferred embodiment, agents and compositions according to the invention may be administered to a subject by injection into the blood stream or directly into a site requiring treatment. Injections may be intravenous (bolus or infusion), subcutaneous (bolus or infusion), intradermal (bolus or infusion) or enhanced by convention (convection enhanced delivery—relevant to local injections at disease site).

It will be appreciated that the amount of the agent that is required is determined by its biological activity and bio-availability, which in turn depends on the mode of administration, the physiochemical properties of the agent (i.e. recombinant phagemid viral particle or the system), and whether it is being used as a monotherapy, or in a combined therapy. The frequency of administration will also be influenced by the half-life of the agent within the subject being treated. Optimal dosages to be administered may be determined by those skilled in the art, and will vary with the particular agent in use, the strength of the pharmaceutical composition, the mode of administration, and the advancement of the disease. Additional factors depending on the particular subject being treated will result in a need to adjust dosages, including subject age, weight, gender, diet, and time of administration.

Generally, a daily dose of between 0.01 µg/kg of body weight and 500 mg/kg of body weight of the agent according to the invention may be used. More preferably, the daily dose is between 0.01 mg/kg of body weight and 400 mg/kg of body weight, and more preferably between 0.1 mg/kg and 200 mg/kg body weight.

As discussed in the Examples, the agent may be administered before, during the or after the onset of disease. For example, the agent may be administered immediately after a subject has developed a disease. Daily doses may be given systemically as a single administration (e.g. a single daily injection). Alternatively, the agent may require administration twice or more times during a day. As an example, the agent may be administered as two (or more depending upon the severity of the disease being treated) daily doses of between 25 mg and 7000 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of agents according to the invention to a patient without the need to administer repeated doses.

Known procedures, such as those conventionally employed by the pharmaceutical industry (e.g. in vivo experimentation, clinical trials, etc.), may be used to form specific formulations comprising the particles or systems according to the invention and precise therapeutic regimes (such as daily doses of the agent and the frequency of administration).

Hence, in a fourteenth aspect of the invention, there is provided a pharmaceutical composition comprising the recombinant phagemid viral particle according to the first aspect, or the system according to the second aspect, and a pharmaceutically acceptable vehicle.

The composition can be used in the therapeutic amelioration, prevention or treatment of any disease in a subject that is treatable with gene therapy, such as cancer.

The invention also provides, in a fifteenth aspect, a process for making the pharmaceutical composition according to the twelfth aspect, the process comprising contacting a therapeutically effective amount of the recombinant phagemid particle according to the first aspect, or the system according to the second aspect, and a pharmaceutically acceptable vehicle.

A "subject" may be a vertebrate, mammal, or domestic animal. Hence, agents, compositions and medicaments according to the invention may be used to treat any mammal, for example livestock (e.g. a horse), pets, or may be used in other veterinary applications. Most preferably, however, the subject is a human being.

A "therapeutically effective amount" of agent (i.e. recombinant phagemid viral particle) is any amount which, when administered to a subject, is the amount of drug that is needed to treat the target disease, or produce the desired effect, e.g. result in effective delivery of the transgene to a target cell or tissue, such as result in tumor killing.

For example, the therapeutically effective amount of agent used may be from about 0.01 mg to about 800 mg, and preferably from about 0.01 mg to about 500 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent (e.g. the particle or system of the invention) may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The particles or system according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The particles or system (i.e. hybrid vector) may be prepared as a sterile solid composition that may be dissolved or suspended at the time of administration using sterile water, saline, or other appropriate sterile injectable medium.

The recombinant phagemid particle, system and pharmaceutical compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The particles and system according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

It will be appreciated that adeno-associated virus (AAV) is often the vector of choice for gene therapy. As a gene delivery vector, lentiviral vectors also have key several advantages over other systems. Firstly, they have a large packaging capacity of at least 8 Kb of DNA, which is an important feature when packaging sizeable expression cassettes of tissue-specific promoters and transgenes. Secondly, they differ from simpler retroviruses not only in the genome organisation, but also in that they are able to transduce non-dividing cells, which is a very useful quality when considering application as a gene therapy vector to non-proliferating tissues such as muscle, neurons and haematopoietic stem cells. In addition, lentivectors have reduced immunogenicity compared to adenoviral vectors, making it possible to consider systemic delivery routes. However, barrier of using AAV or lentivirus for laboratory and clinical research include their extremely high production cost and low yields.

The inventors have shown that in addition to exhibiting useful applications in gene therapy, imaging and vaccine delivery, the recombinant phagemid particle of the invention can also be used to produce recombinant viral vectors, such as AAV or lentivirus, in vitro or in vivo (including in situ). Phage-guided AAV production utilizes the ability of the phagemid particles to package large amounts of single-stranded ssDNA. A typical AAV production system consists of three major elements: rAAV, rep-cap and adenohelper genes, which function together to produce rAAV particles.

Thus, in a sixteenth aspect, there is provided use of the phagemid particle according to the first aspect or the system according to the second aspect, to produce a recombinant viral vector comprising or derived from the viral genome within the genome of the phagemid particle.

In a seventeenth aspect, there is provided a method for producing recombinant viral vector, the method comprising introducing into, a eukaryotic host cell, the recombinant phagemid particle according to the first aspect, or the system according to the second aspect, and allowing the host cell to produce recombinant viral vector.

Preferably, the recombinant virus product is a recombinant mammalian virus, such as AAV or lentivirus. Preferably, the viral vector product is rAAV. Preferably, the phagemid viral particle according to the first aspect, or the system according to the second aspect is used in cis and/or trans together with the delivery and/or presence of other genetic elements required for the production of mammalian viruses, as determined by the phagemid particle's genome, inside the eukaryotic host cell. The method used to assist or enhance gene transfer to the host cell by the phagemid particle includes those described in WO 2014/184528 (i.e. multifunctional) and WO 2014/184529 (i.e. combination with a cationic polymer to form a complex having a net positive charge).

The eukaryotic host cell may be mammalian. The host cell may comprise or be derived from Human Embryonic Kidney Cells (HEK293), *Spodoptera frugiperda* pupal ovarian tissue (Sf9), or Chinese Hamster Ovary (CHO). Insect cells are also envisaged.

In one embodiment, the host cell may be transformed with one or more phagemid particle genome carrying genes selected from the group consisting of: rAAV, lentivirus, capsid, replication, helper protein encoding genes, and any other genes required for the expression and packaging of mammalian viruses.

For example, in hybrid phagemid particle-guided rAAV production, the rAAV gene may be carried by the recombinant phagemid viral particle according to the first aspect, as shown in FIG. 3, and the adenohelper and rep-cap genes may be carried on separate vectors, or be integrated into the eukaryotic host genome. For example, FIG. 12 shows the adenohelper genes on one vector, and FIG. 13 shows the rep-cap on a separate vector. Any combinations of the rAAV, rep-cap and adenohelper genes may be carried on one or more vectors, i.e. in cis or trans configurations. Alternatively, rep-cap or adenohelper proteins, in the context of rAAV production, could also be integrated or introduced into the eukaryotic host as a stably expressed accessory DNA (e.g. a plasmid), whereby the hybrid phagemid particle supplies the recombinant viral genome for packaging into a recombinant virus, as determined by the transgene cassette inside the phagemid particle's genome.

In one preferred embodiment, rAAV, rep-cap and adenohelper genes are carried on a single vector, as shown in FIGS. 14 and 15. The inventors believe that this is the first time that all three sets of genes have been harboured on the same vector.

Hence, in an eighteenth aspect, there is provided a recombinant vector comprising comprising rAAV, rep-cap and adenohelper genes.

In a nineteenth aspect, there is provided a recombinant phagemid particle comprising the vector of the eighteenth aspect.

In a twentieth aspect, there is provided use of the vector according to the eighteenth aspect or the particle of the nineteenth aspect, to produce a recombinant AAV viral vector comprising or derived from the viral genome of the phagemid particle.

In a twenty first aspect, there is provided a method for producing recombinant AAV viral vector, the method comprising introducing into, a eukaryotic host cell, the vector according to the eighteenth aspect or the particle of the nineteenth aspect, and allowing the host cell to produce recombinant viral vector.

When introduced into the same eukaryotic host cell (see FIGS. 11 and 14), the rep-cap and adenohelper genes on the vector behave as trans-acting or cis-acting or a combination of both elements that facilitate packaging of the rAAV genome in the AAV virus capsid, in the context of rAAV production. This production process is comparable to transient co-transfection of multiple plasmids, and usually involving three plasmids. However, in this embodiment, the plasmids are replaced with the recombinant phagemid particles of the invention, which are targeted to eukaryotic cells (preferably mammalian cells), which also carry the same elements.

The method may be carried out in vivo, in vitro, ex vivo, or in situ. For in situ production, the recombinant phagemid particles preferably comprise a targeting moiety for the target eukaryotic cell that is the designated eukaryotic host. Preferably, in the context of in situ, ex vivo and in vivo virus production, the designated eukaryotic host cell type is a diseased cell. Preferably, the diseased cell is a malignant or benign tumour. In the context of in vitro virus production, preferably the eukaryotic host is a derivative of any of the eukaryotic hosts listed above. The application of the recombinant phagemid particles and genetic elements required for the production of recombinant virus (as determined by the transgene cassette in the hybrid phagemid particle), could be in any fashion as indicated earlier, either in cis-acting or trans-acting combinations, inside the eukaryotic host cell.

It will be appreciated that the invention extends to any nucleic acid or peptide or variant, derivative or analogue thereof, which comprises substantially the amino acid or nucleic acid sequences of any of the sequences referred to herein, including functional variants or functional fragments thereof. The terms "substantially the amino acid/polynucleotide/polypeptide sequence", "functional variant" and "functional fragment", can be a sequence that has at least 40% sequence identity with the amino acid/polynucleotide/polypeptide sequences of any one of the sequences referred to herein, for example 40% identity with the nucleic acids identified herein.

Amino acid/polynucleotide/polypeptide sequences with a sequence identity which is greater than 65%, more preferably greater than 70%, even more preferably greater than 75%, and still more preferably greater than 80% sequence identity to any of the sequences referred to is also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences is then calculated from such an alignment as (N/T)*100, where N is the number of positions at which the sequences share an identical residue, and T is the total number of positions compared including gaps but excluding overhangs. Hence, a most preferred method for calculating relative percentage identity between two sequences comprises (i) preparing a sequence alignment using the ClustalW program using a suitable set of parameters, for example, as set out above; and (ii) inserting the values of N and T into the following formula:—Sequence Identity=(N/T)*100.

Alternative methods for identifying similar sequences will be known to those skilled in the art. For example, a substantially similar nucleotide sequence will be encoded by a sequence which hybridizes to a nucleic acid sequence described herein, or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown herein.

Due to the degeneracy of the genetic code, it is clear that any nucleic acid sequence could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

FIG. 1 is a table showing features of the phagemid-AAV (PAAV) virus particle according to the invention compared to prior art AAVP virus particles;

FIG. 2 shows schematic illustrations of embodiments of a Helper Phage and a Phagemid genome (PAAV) according to the invention, and a phagemid-AAV (PAAV) particle that is created by the Helper and phagemid. Structural genes are integral to packaging of DNA in to virus particles, and are supplied by the replication-defective Helper phage. The phagemid genome is extremely parasitic to the Helper phage. Ultimately, the PAAV particles are produced at yields that far surpass prior art systems;

Figure 3:
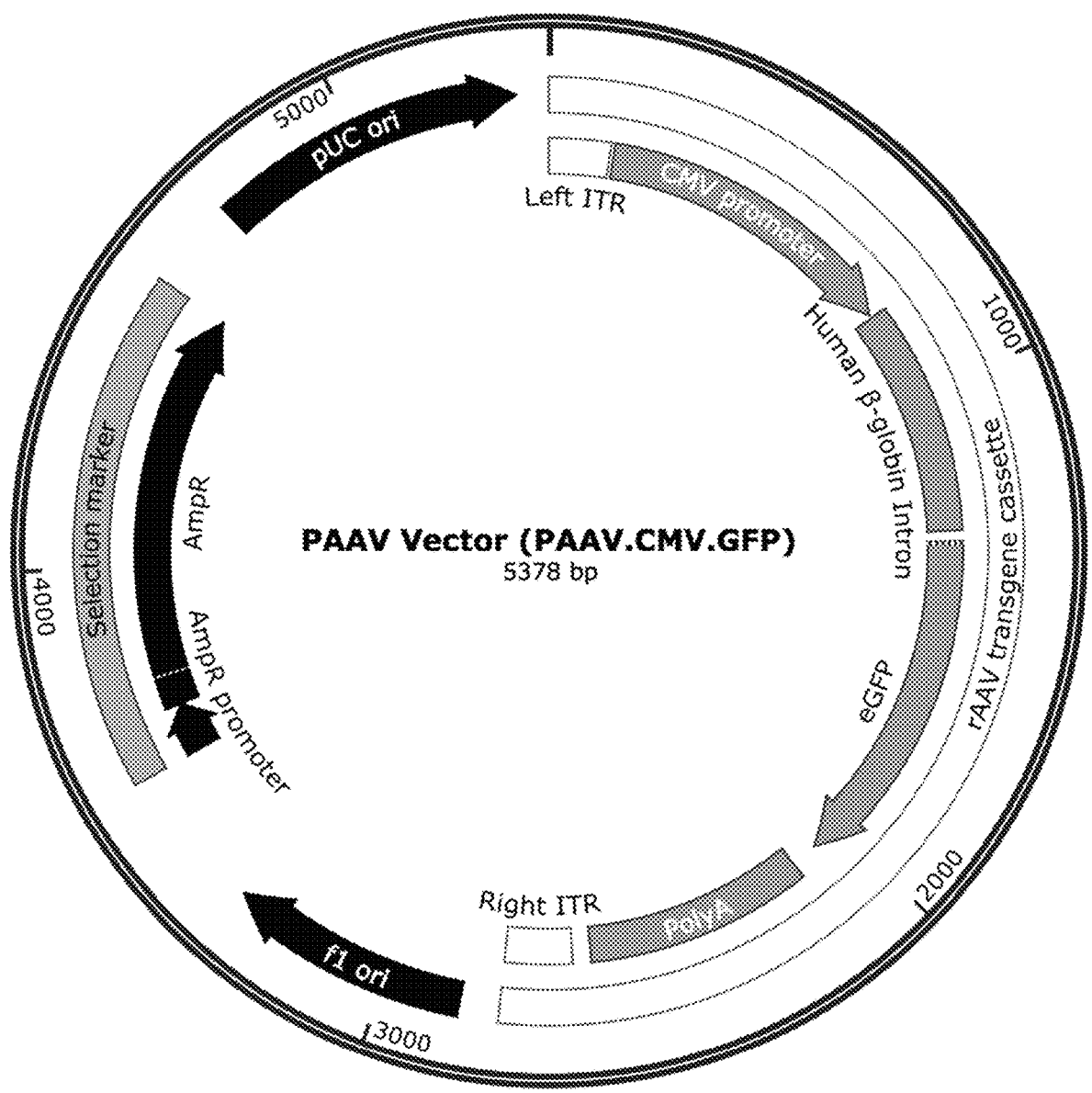
FIG. 3 is a schematic representation of one embodiment of a phagemid genome (PAAV)
Figure 5:
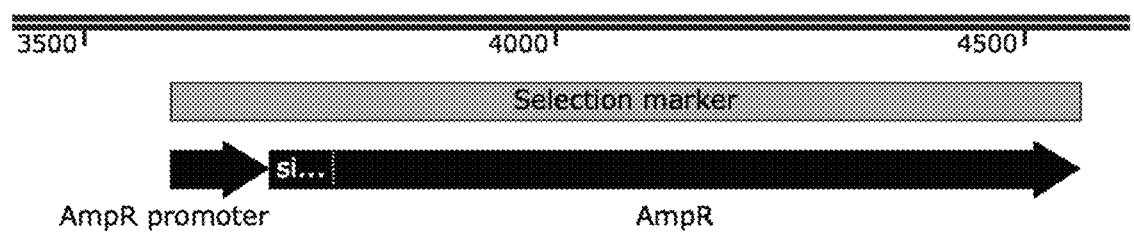
FIG. 5 shows the location of a selection marker gene (AmpR) on a recombinant adeno-associated virus (rAAV) transgene cassette on the phagemid genome shown in FIG. 3.
Figure 6:
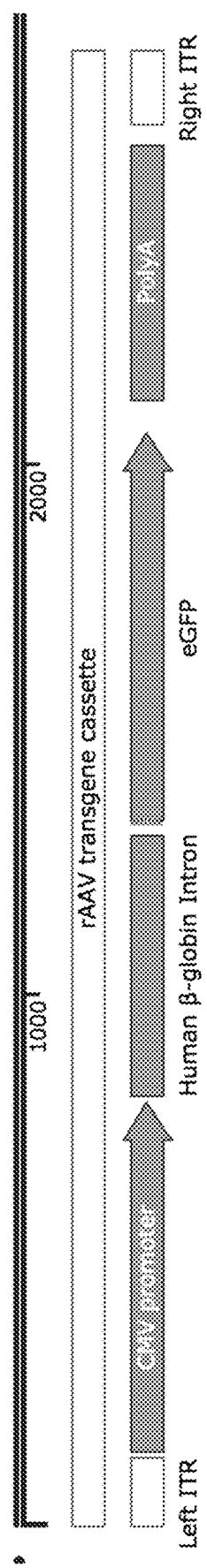
Figure 7:
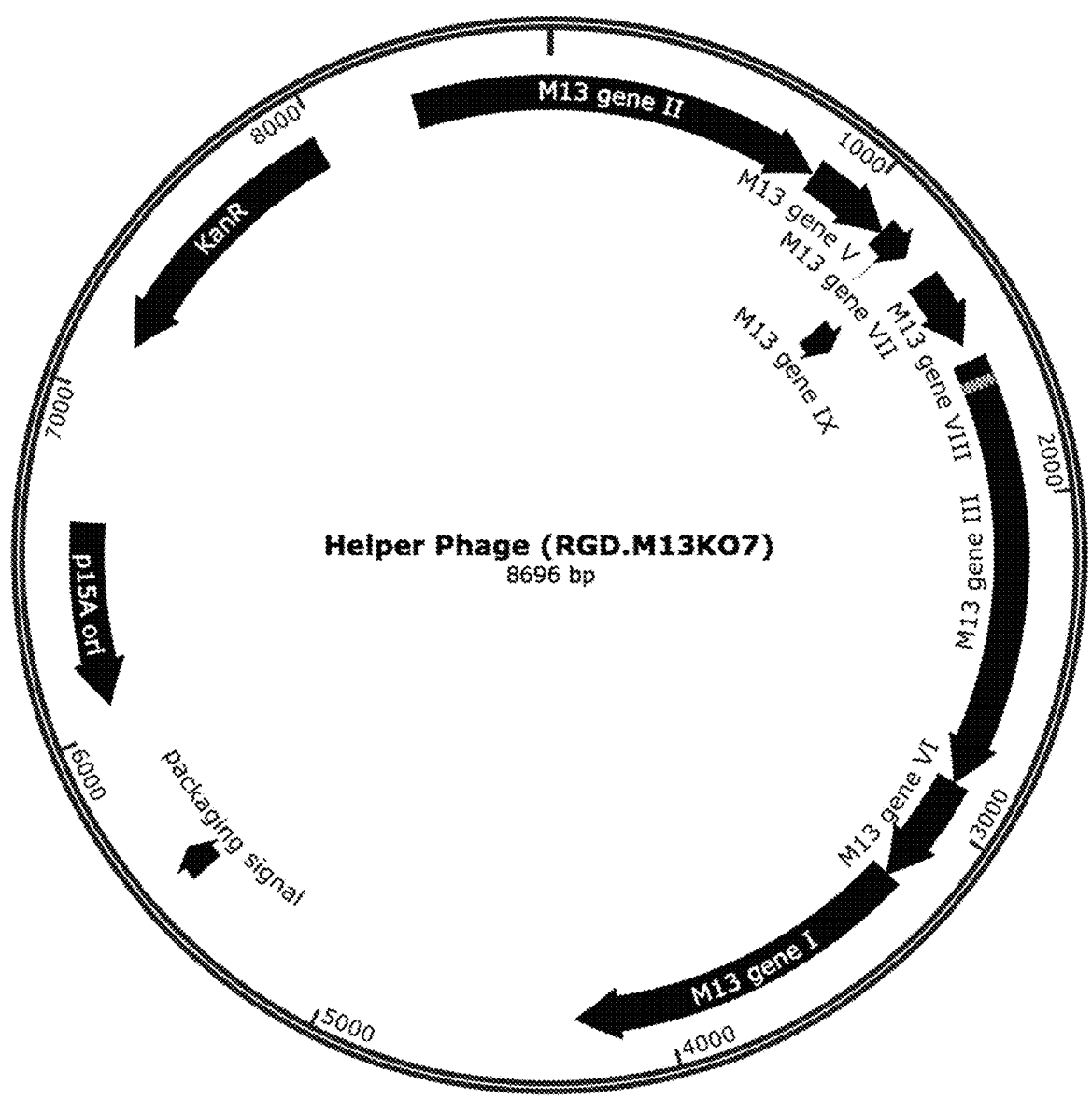
Figure 8:
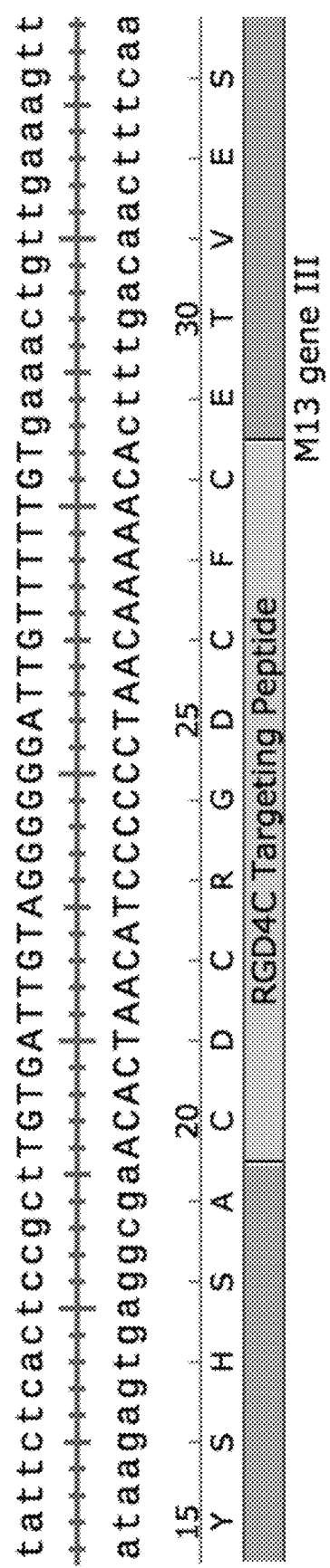
Figure 9:
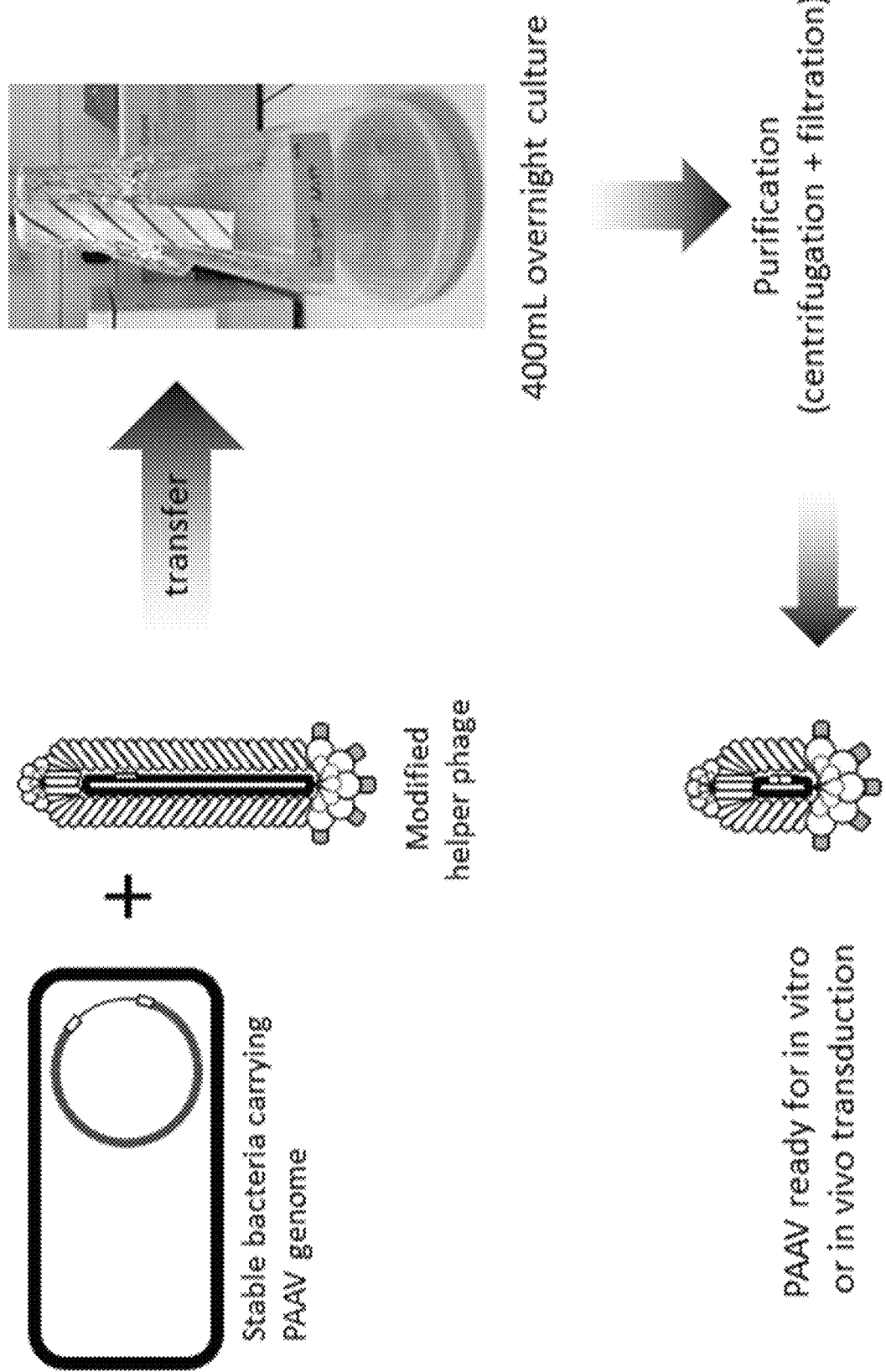
Figure 10:
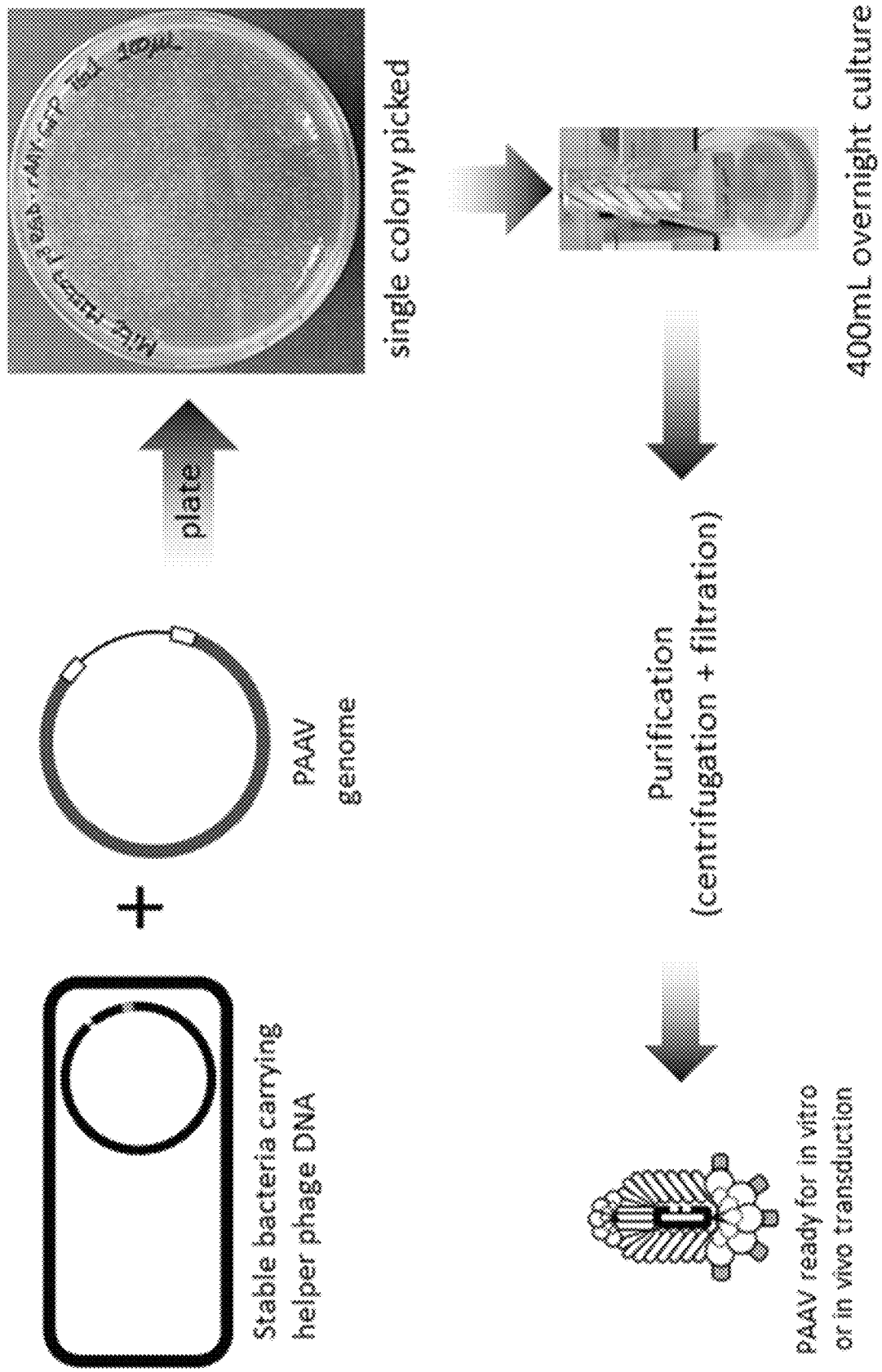
Figure 11:
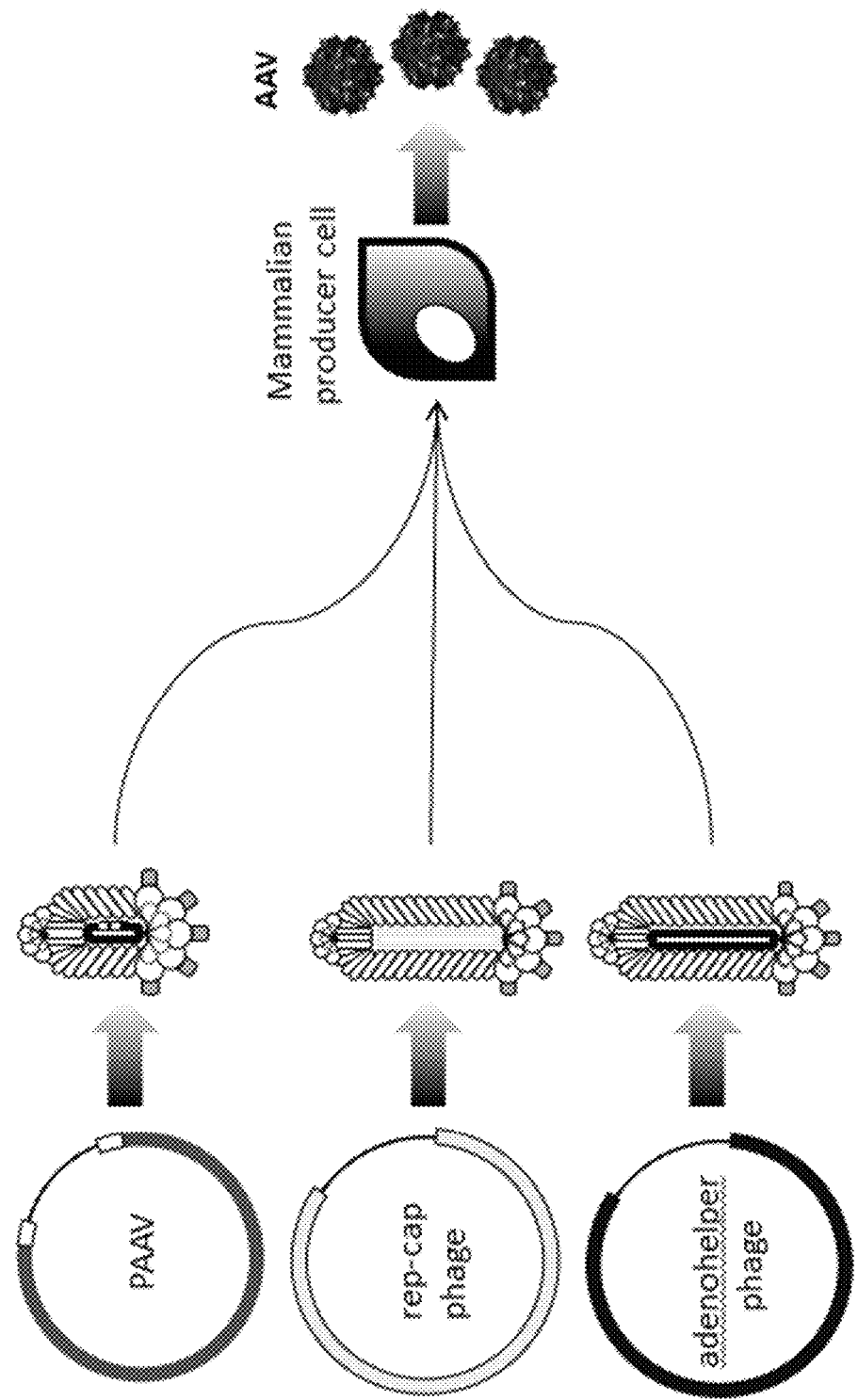
Figure 12:
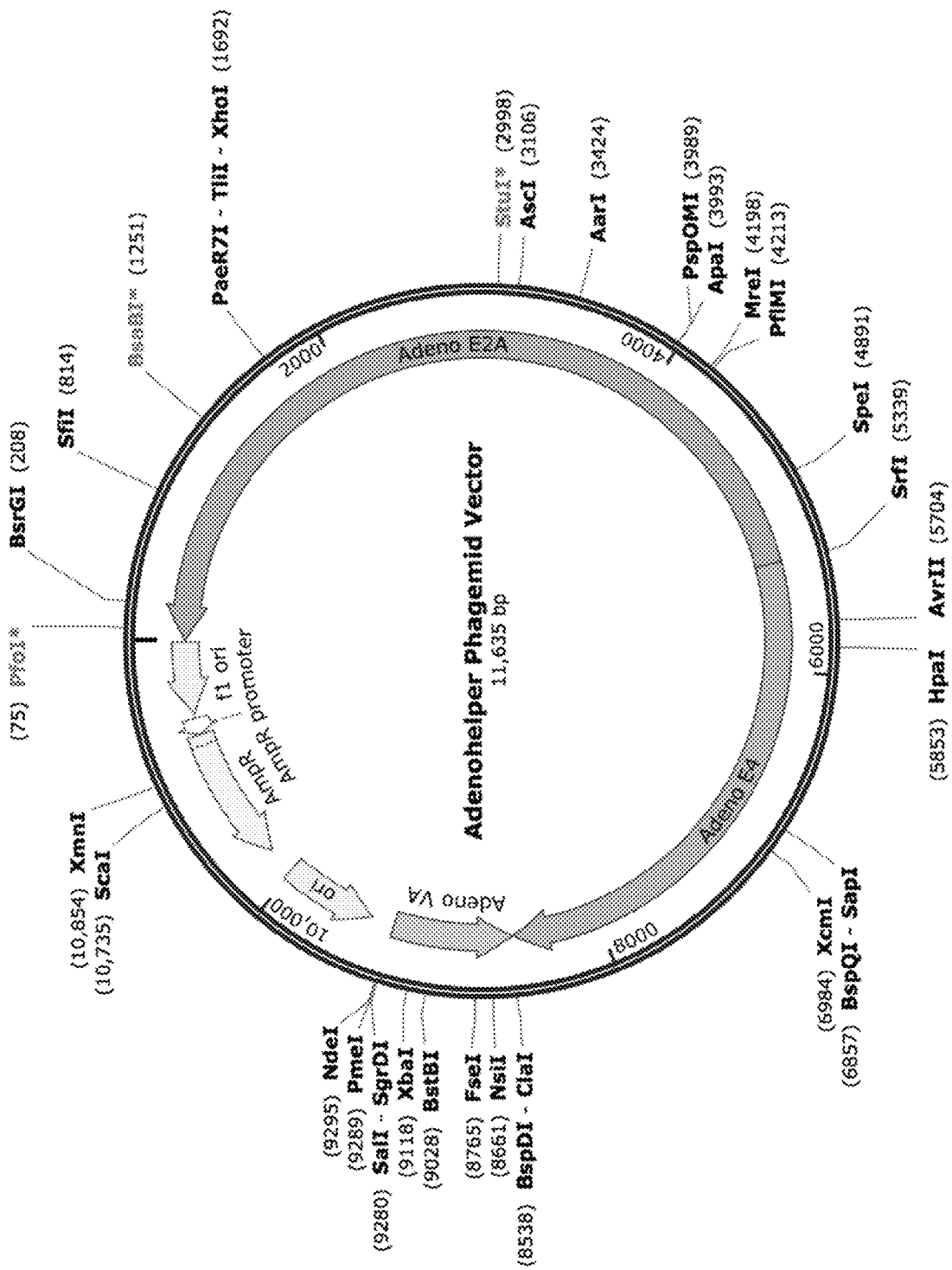
Figure 13:
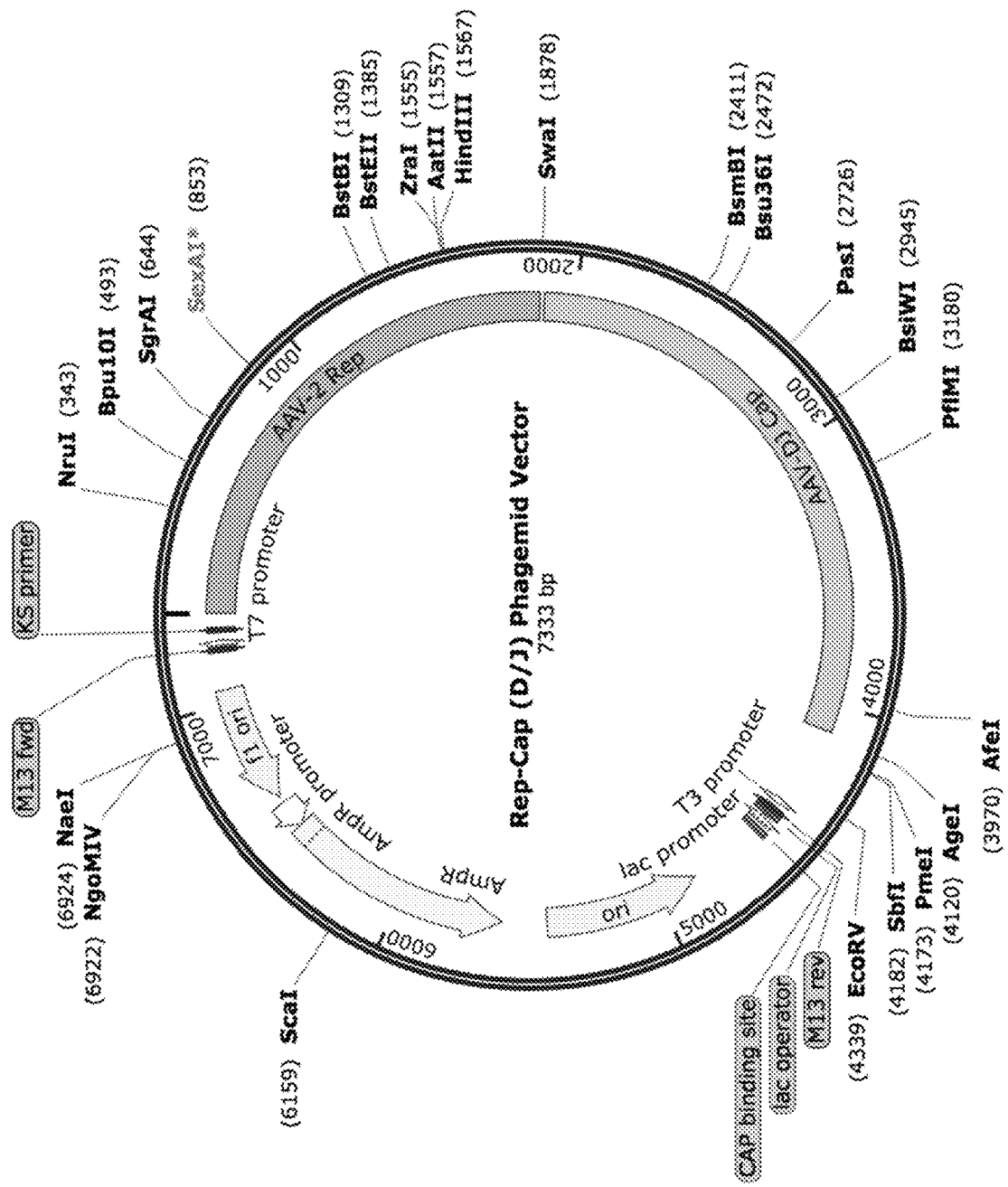
Figure 14:
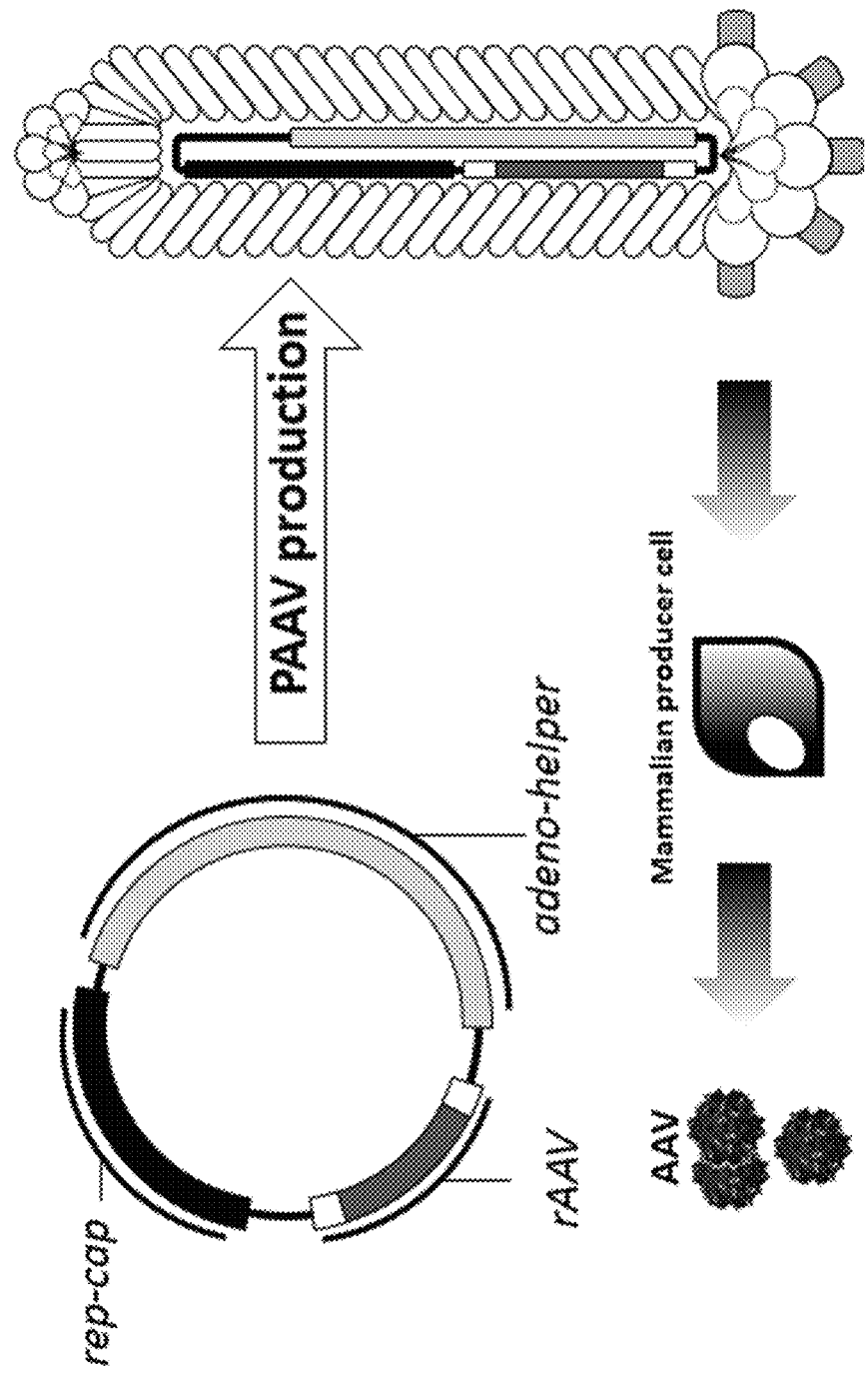
Figure 15:
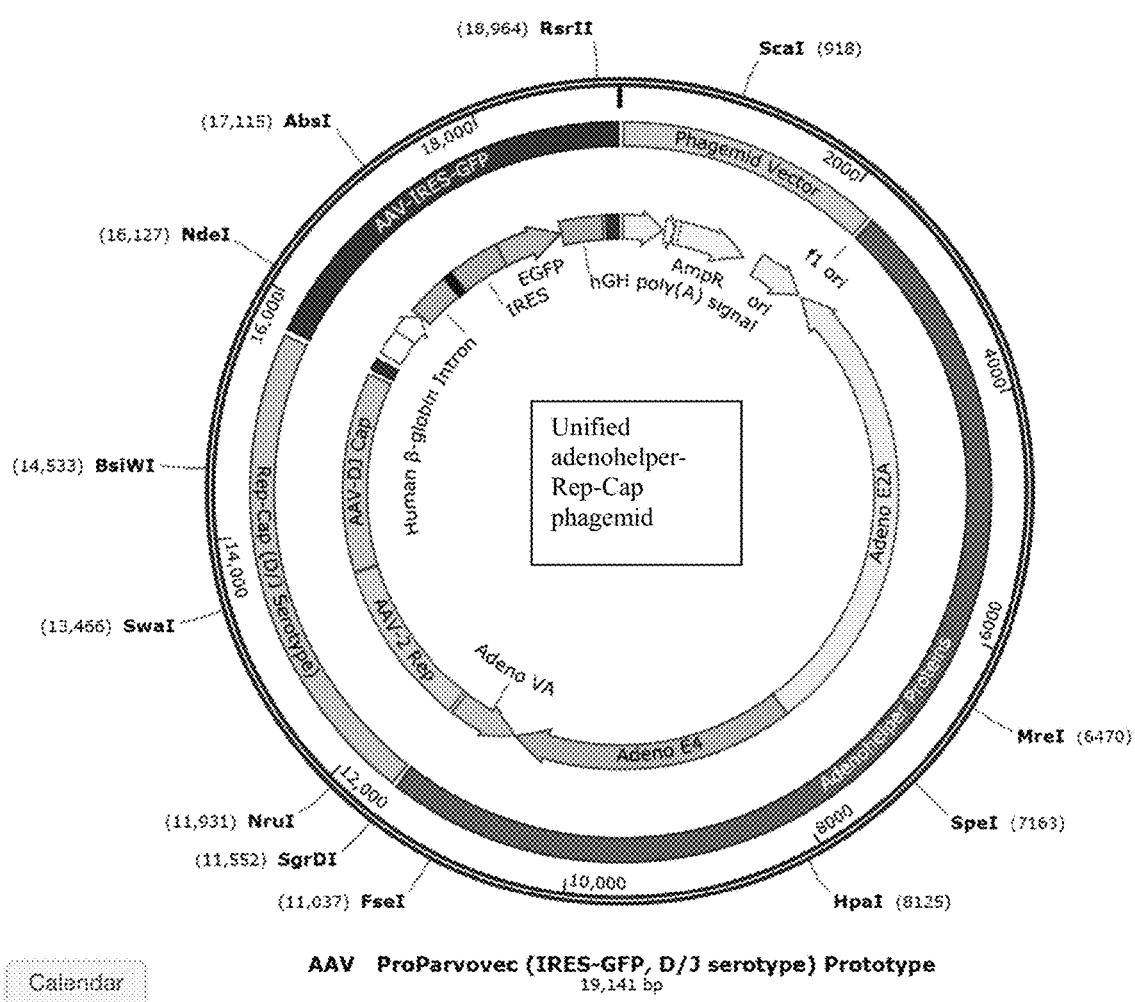
Figure 16:
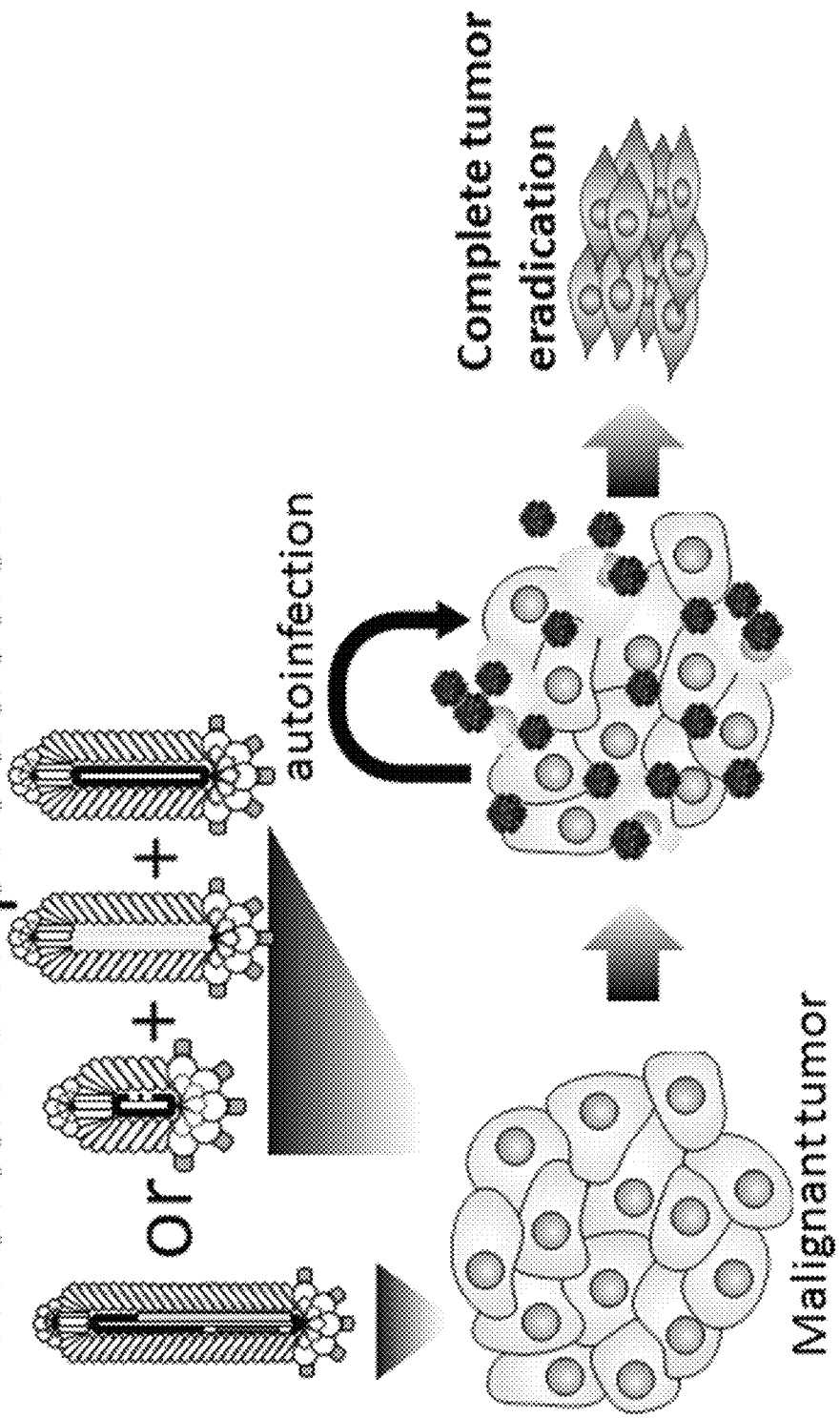
Figure 17:
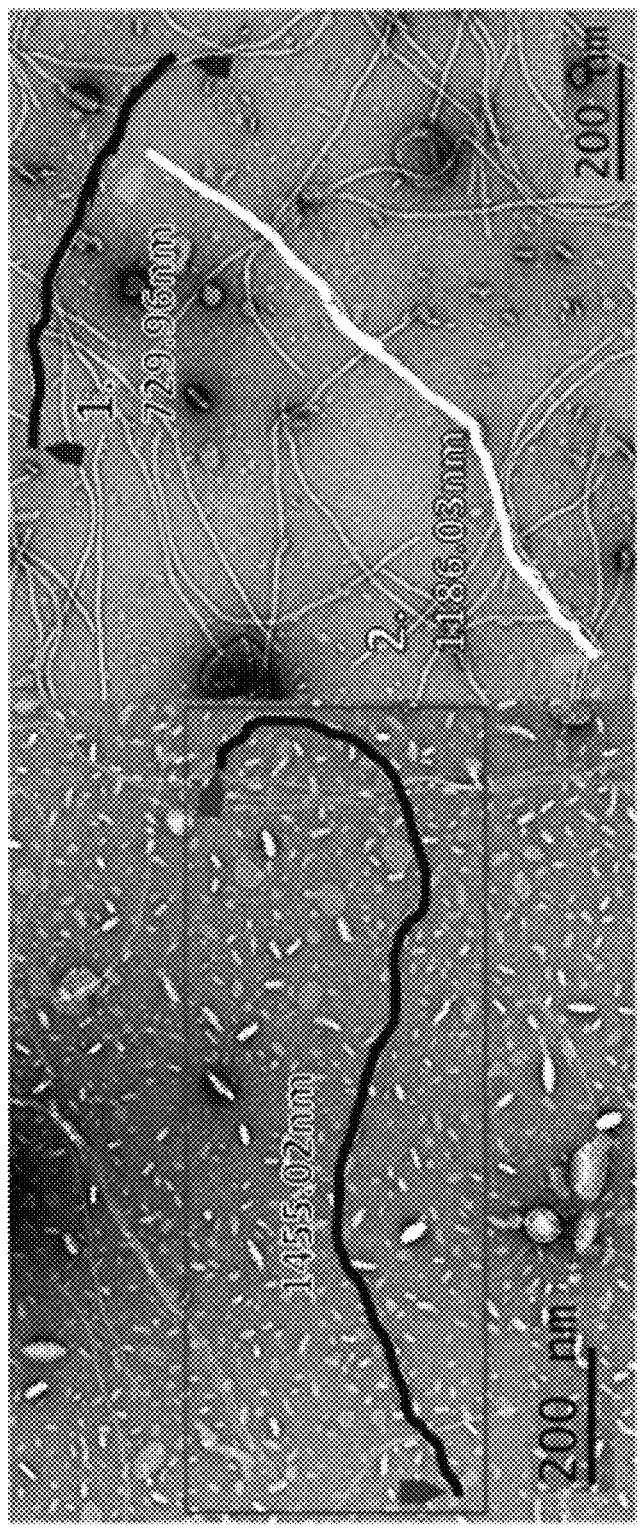
Figure 18:
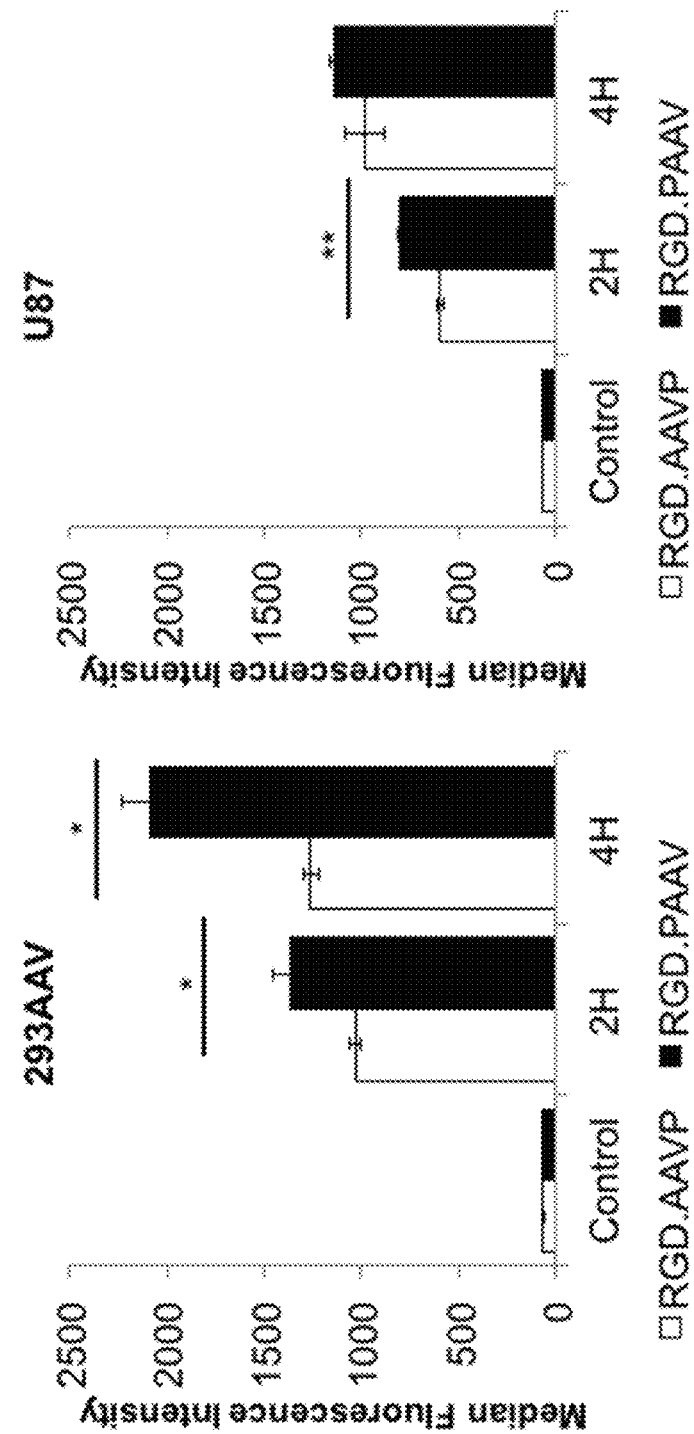
Figure 19:
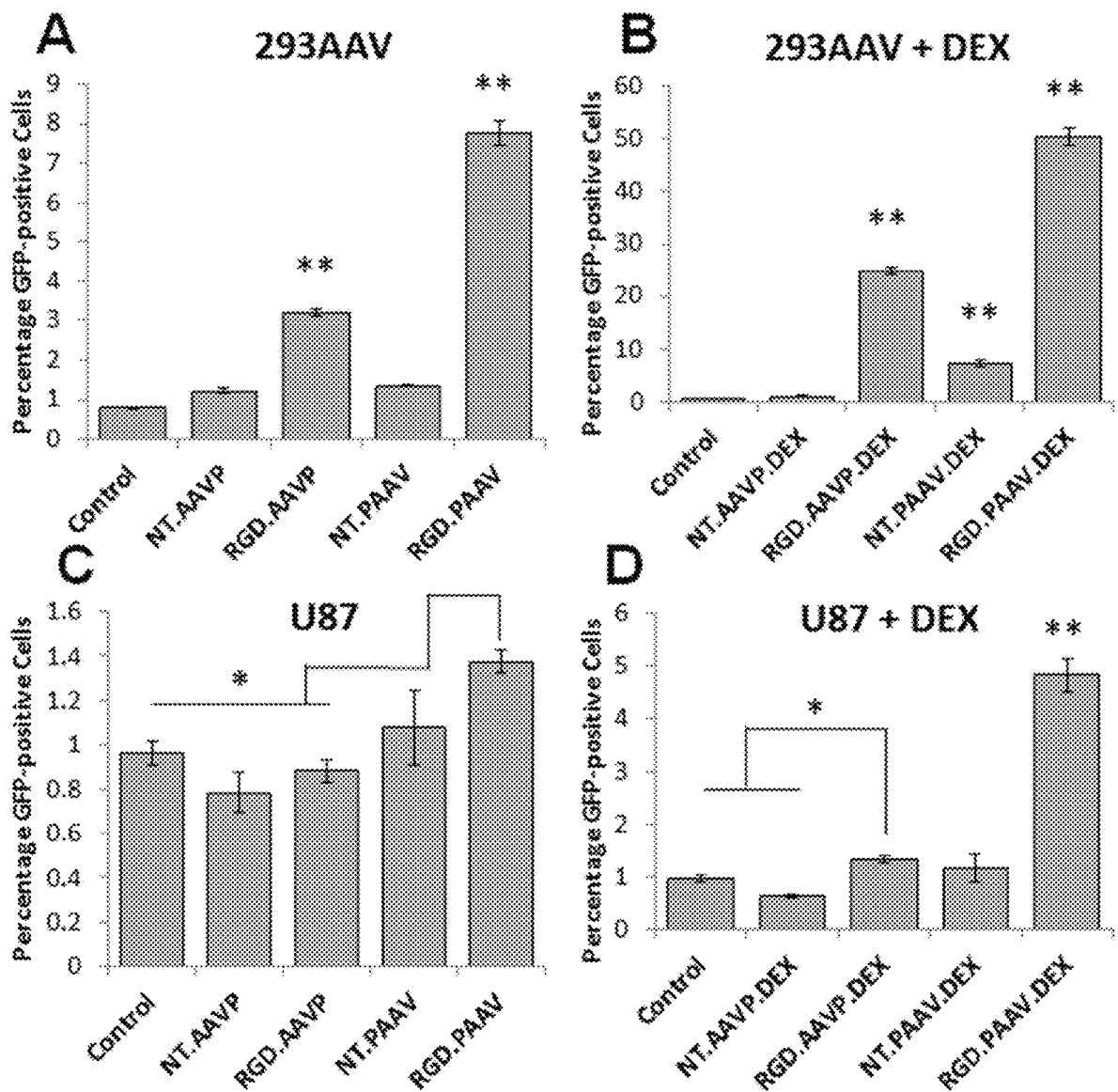
Figure 20:
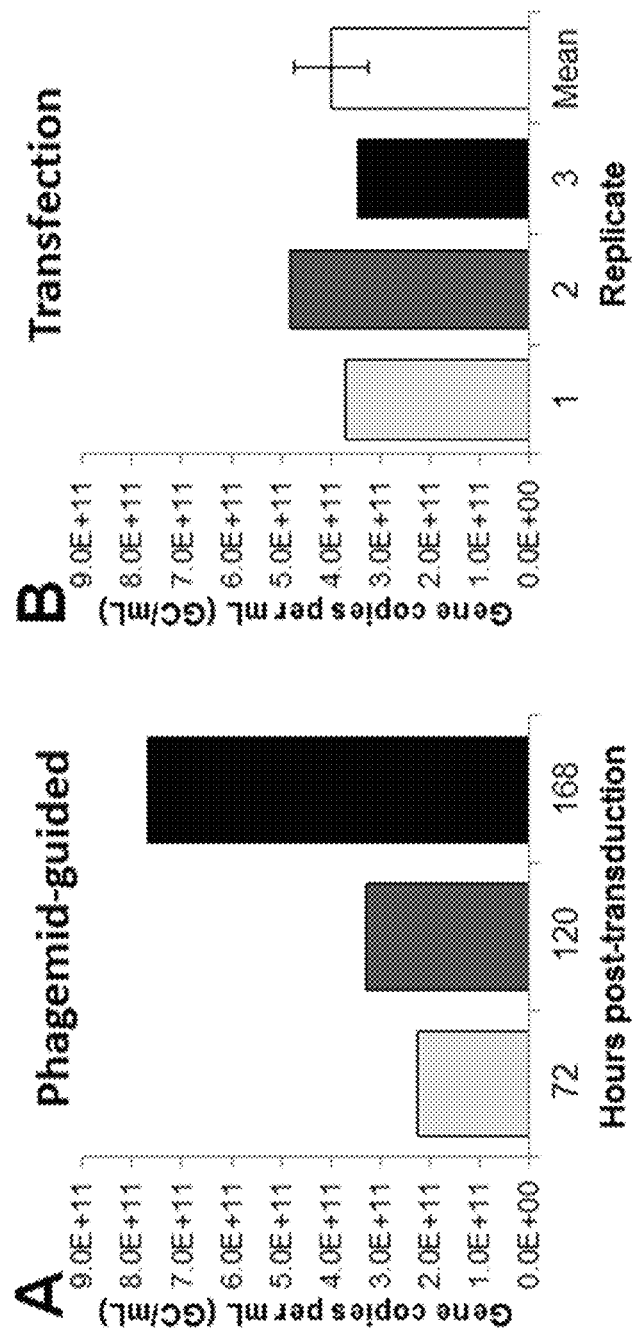
Figure 21:
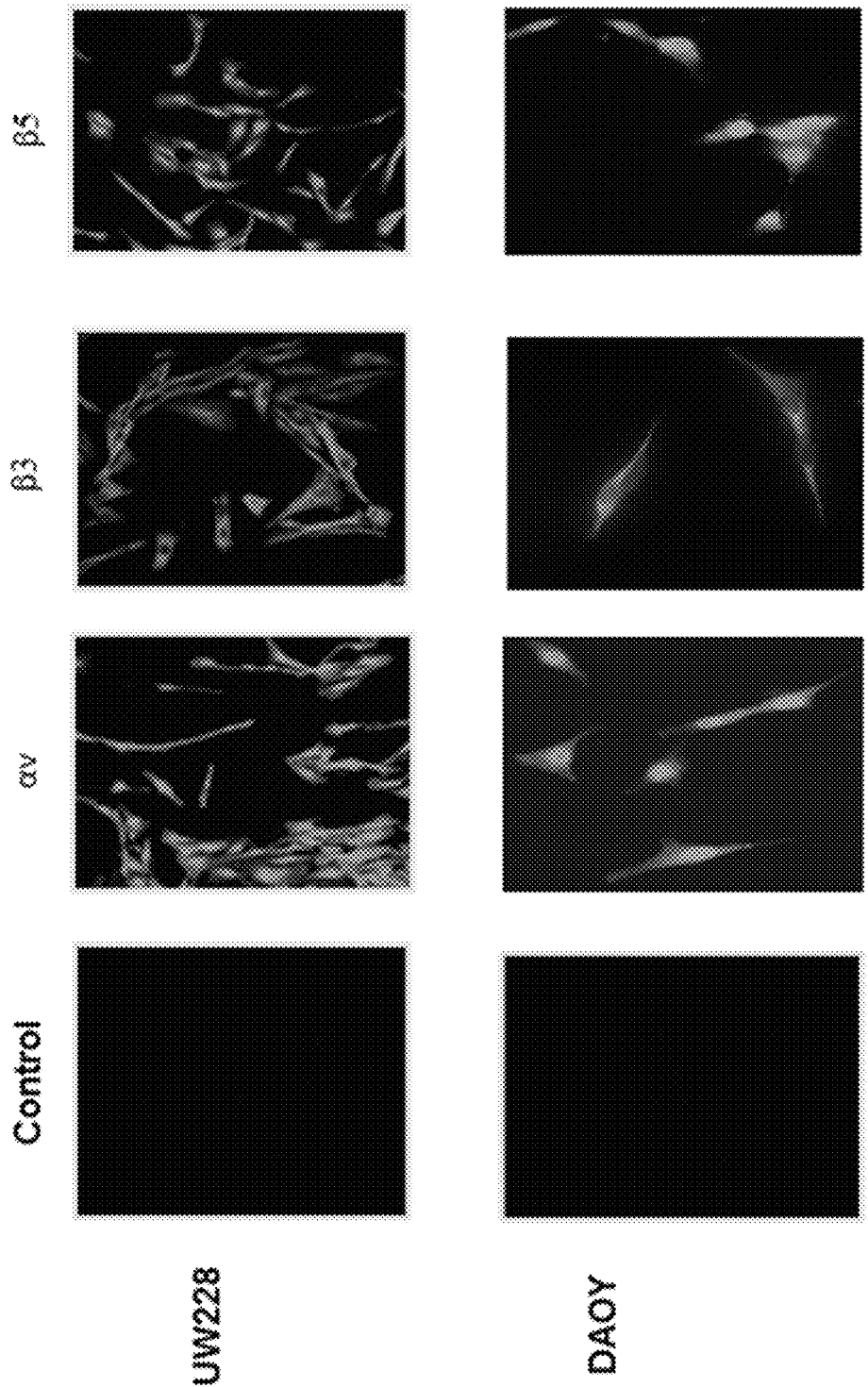
Figure 22:
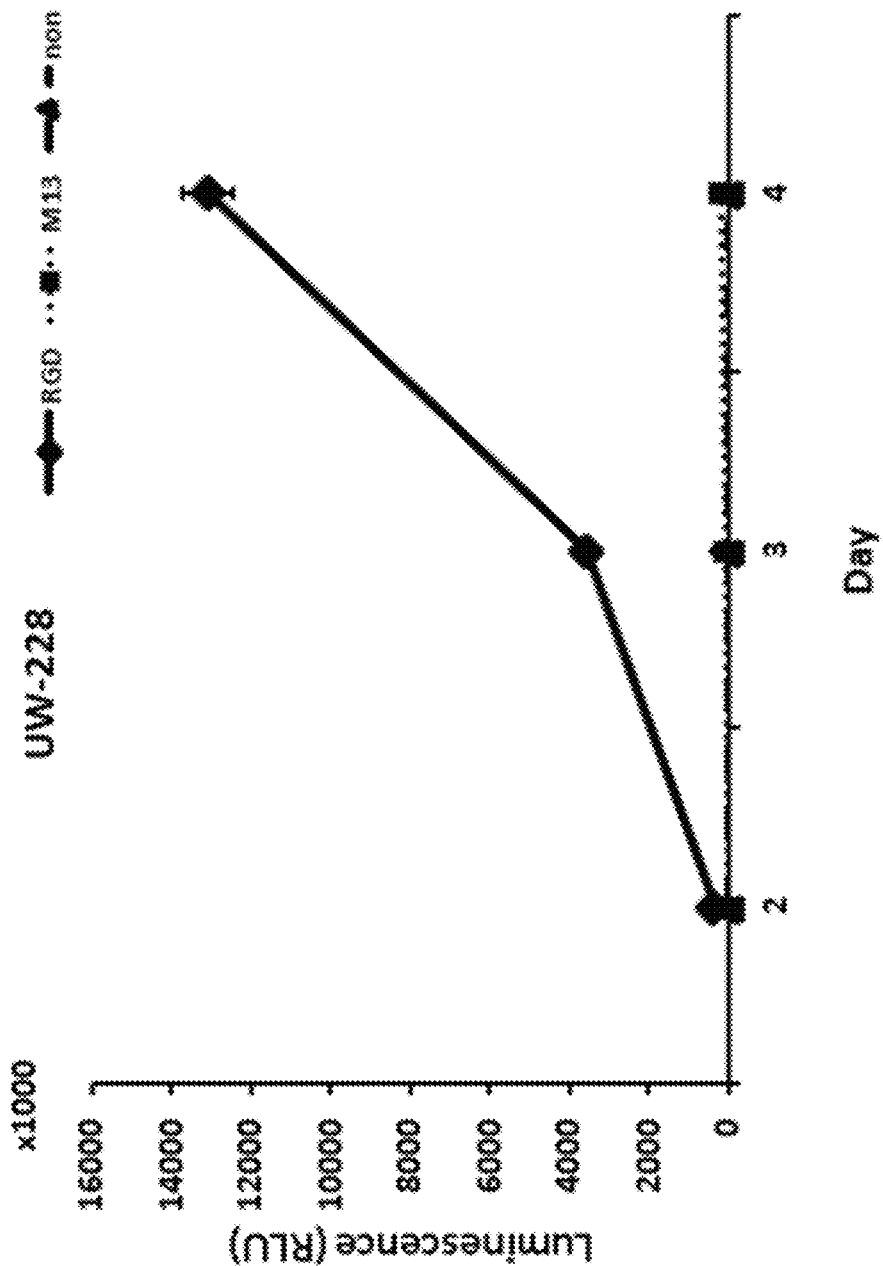
Figure 23:
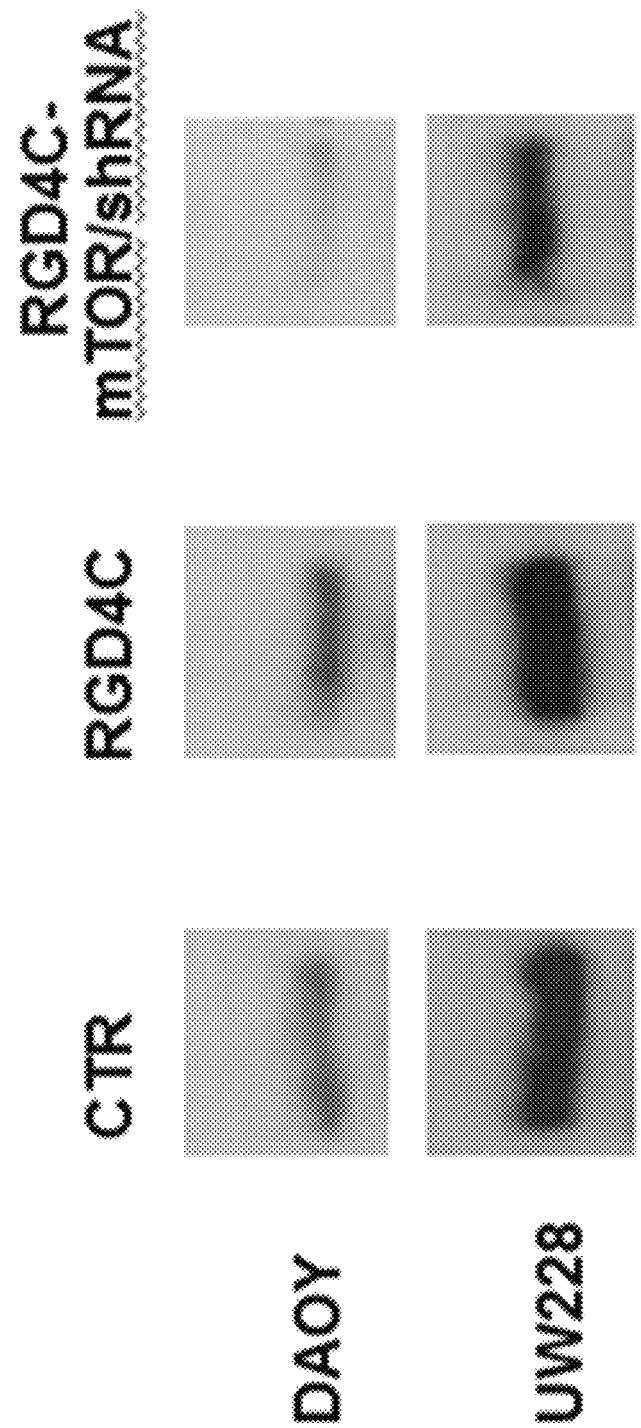
Figure 24:
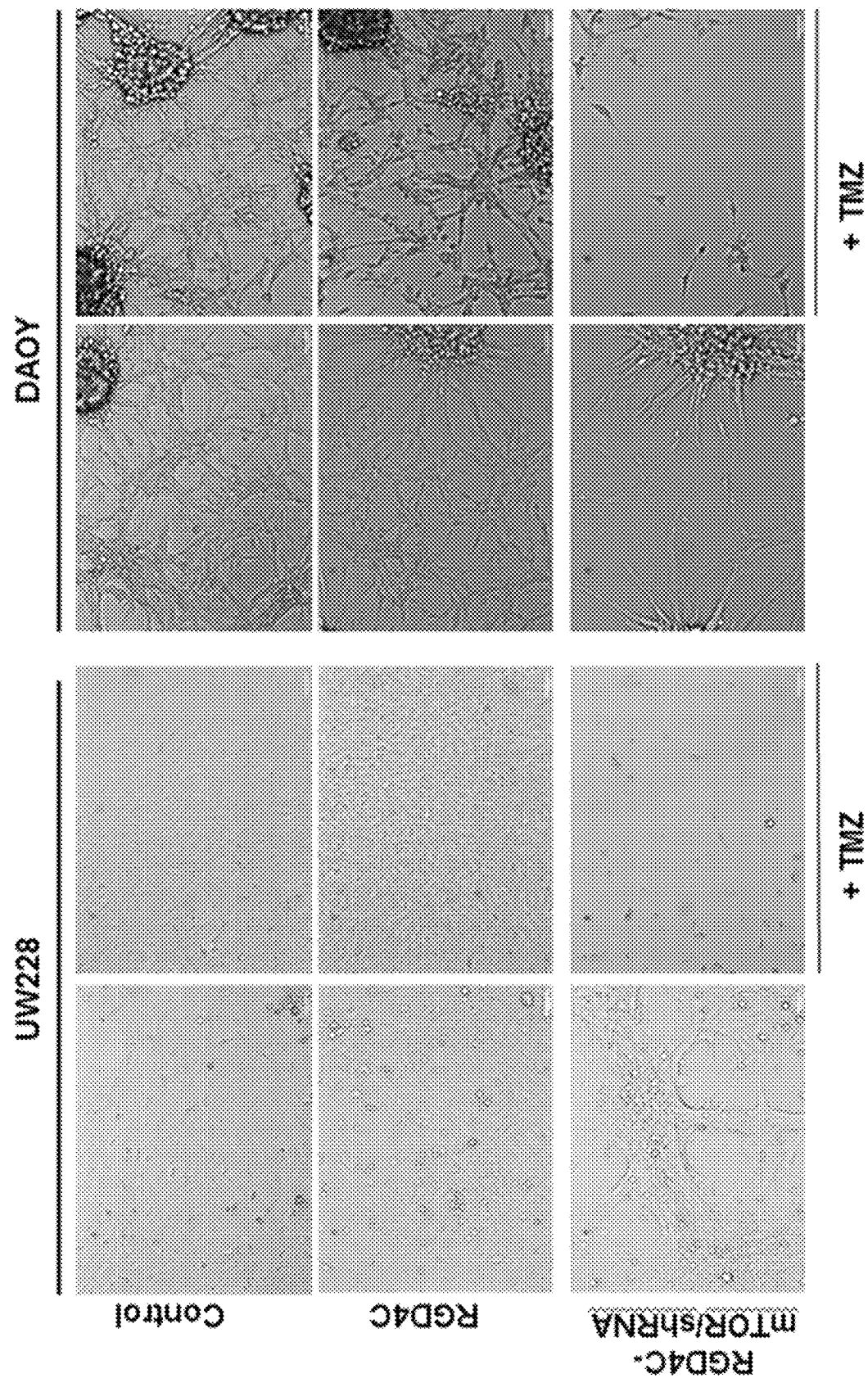
Figure 25:
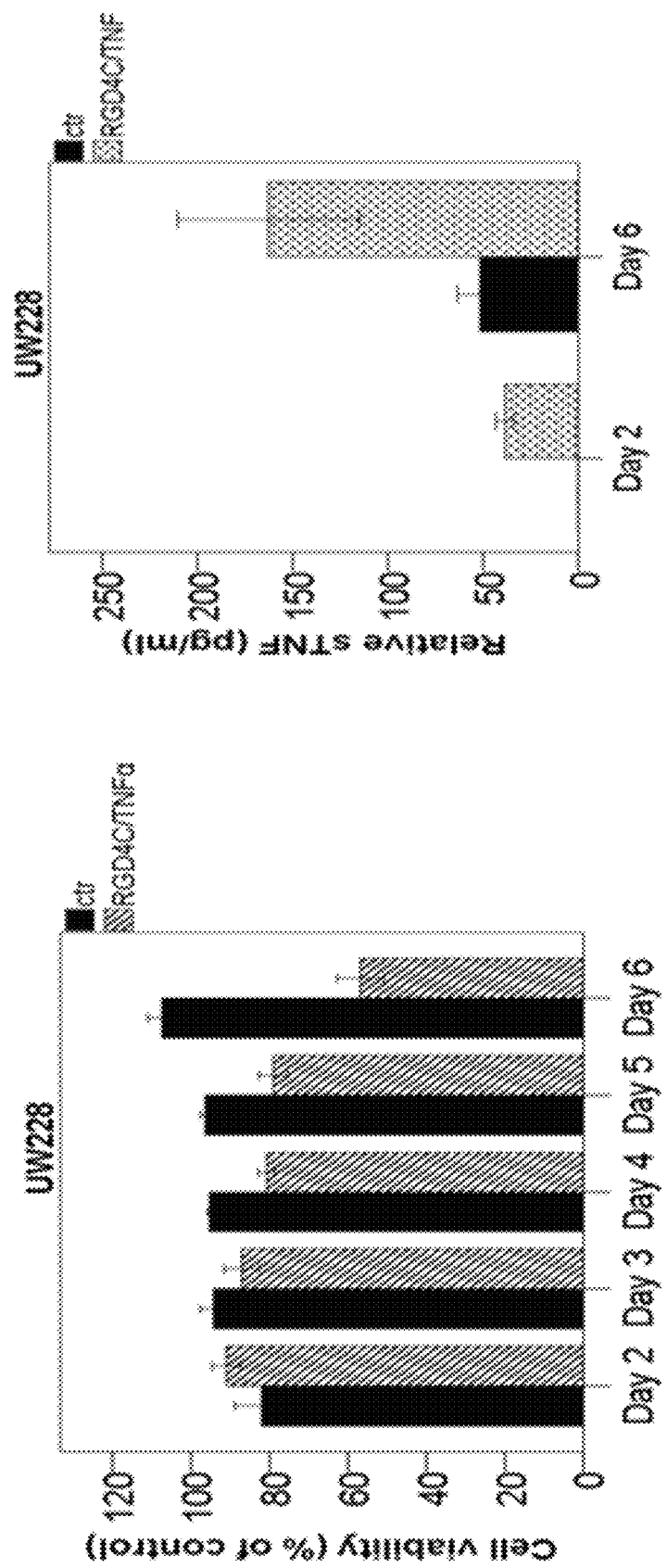
Figure 26:
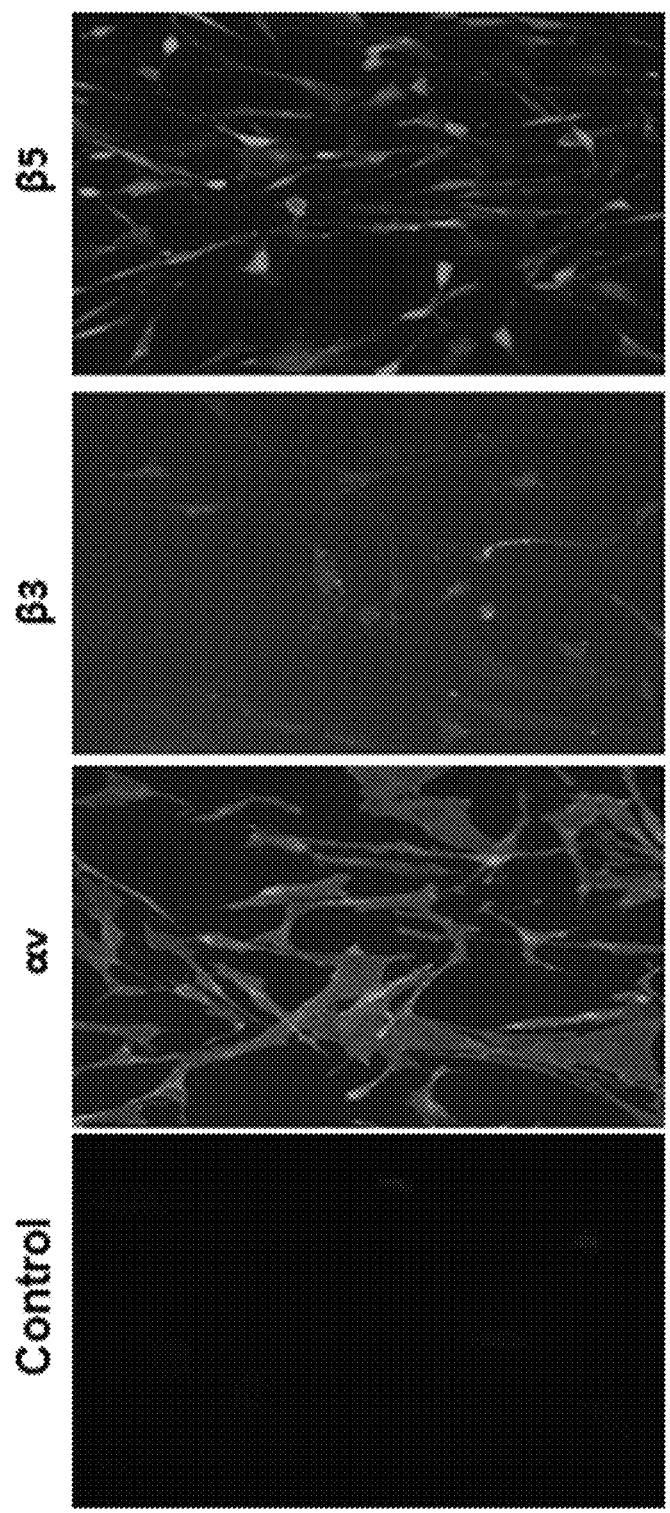
Figure 27:
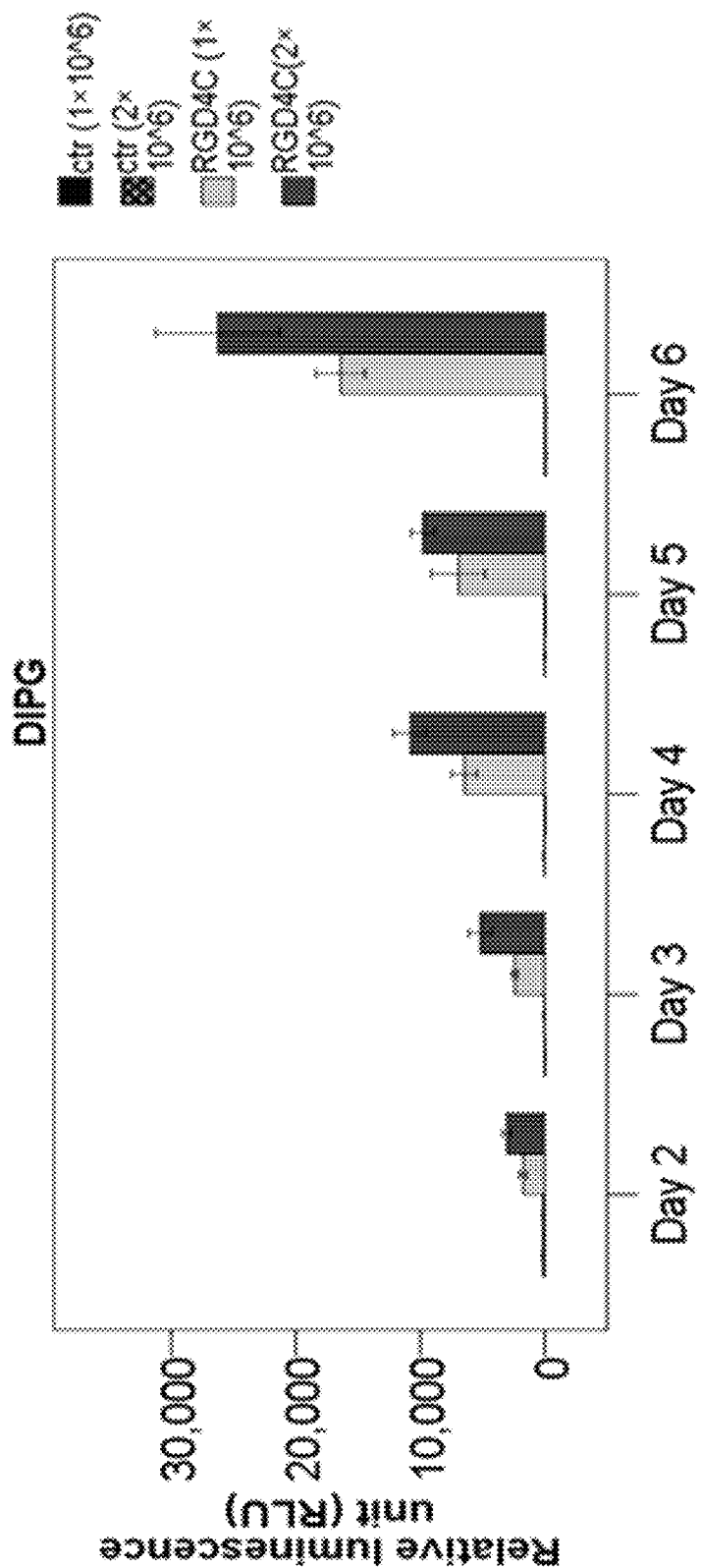
Figure 28:
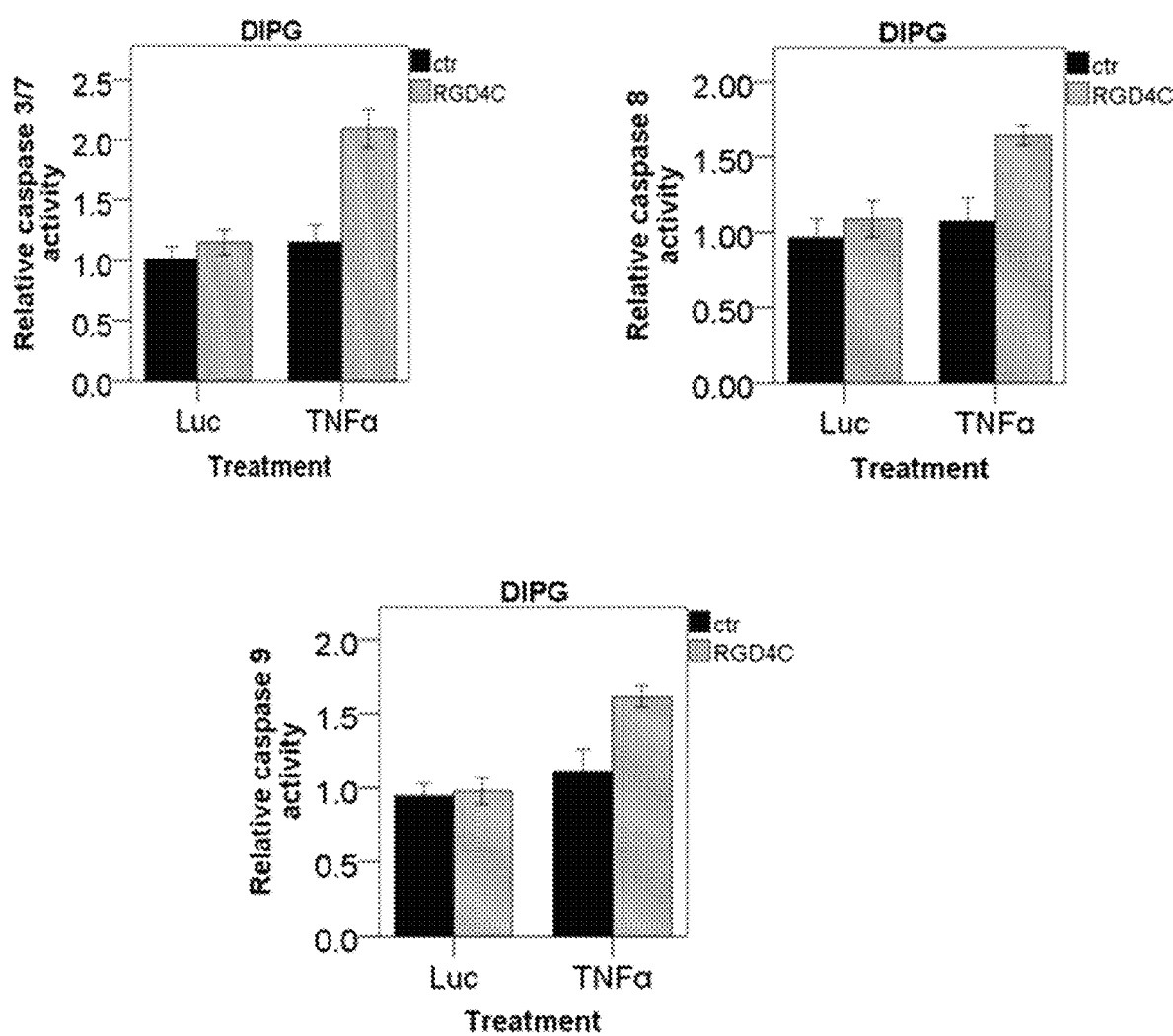
Figure 29:
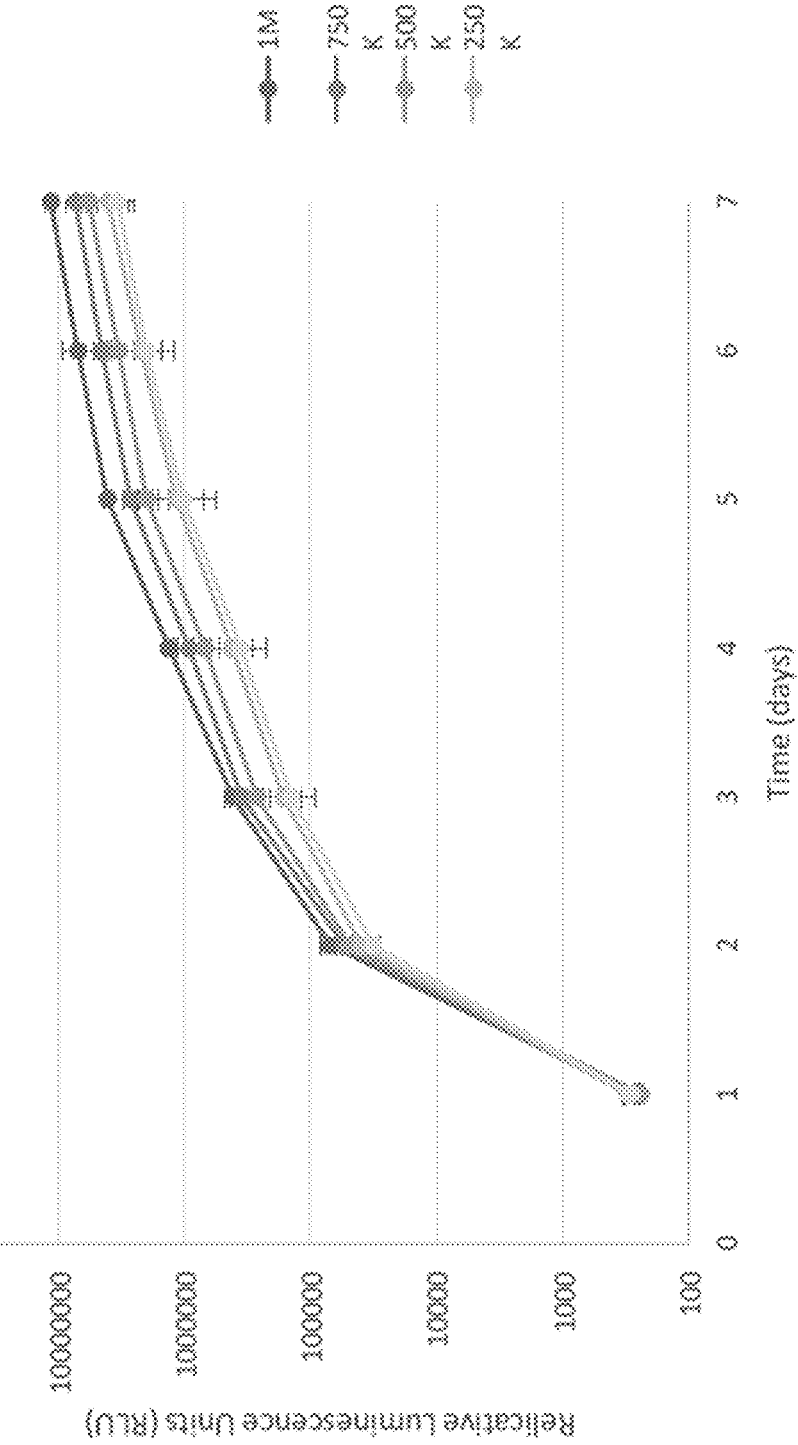
Figure 30:
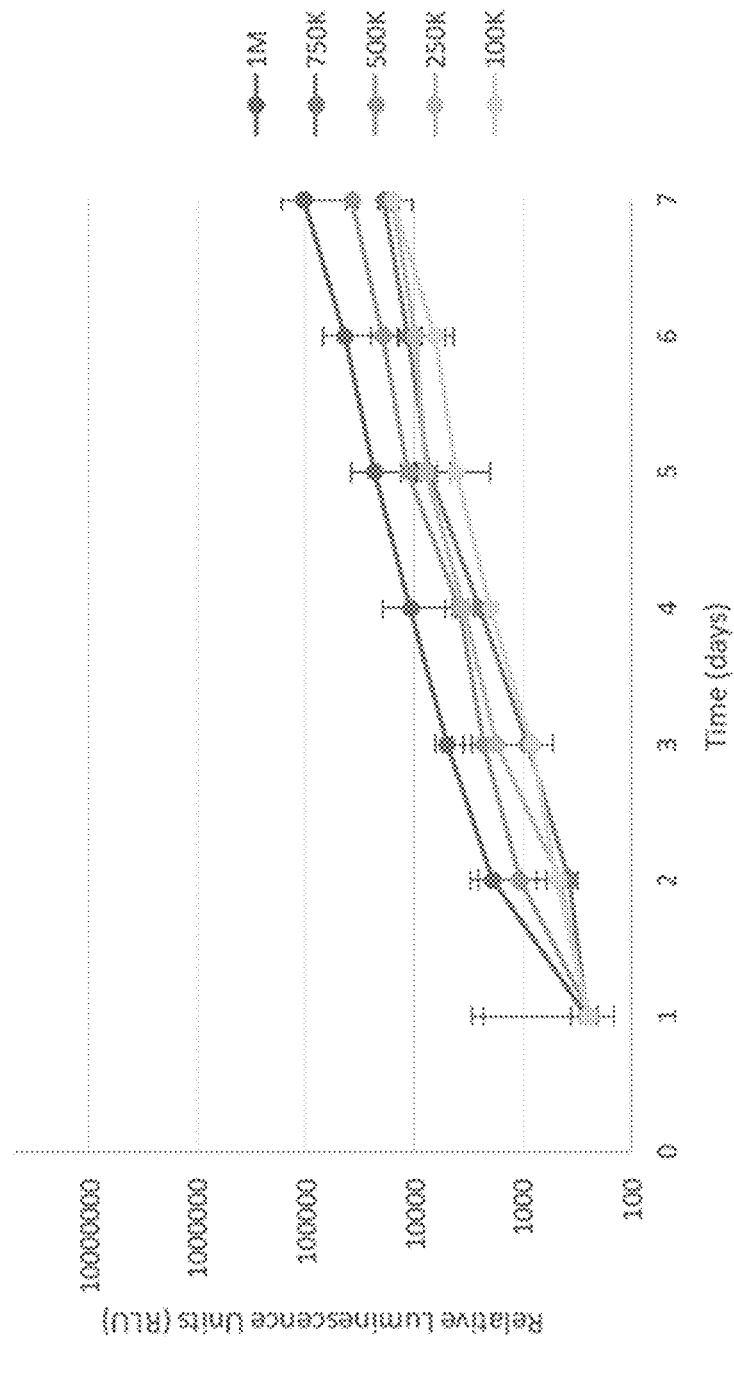
Figure 31:
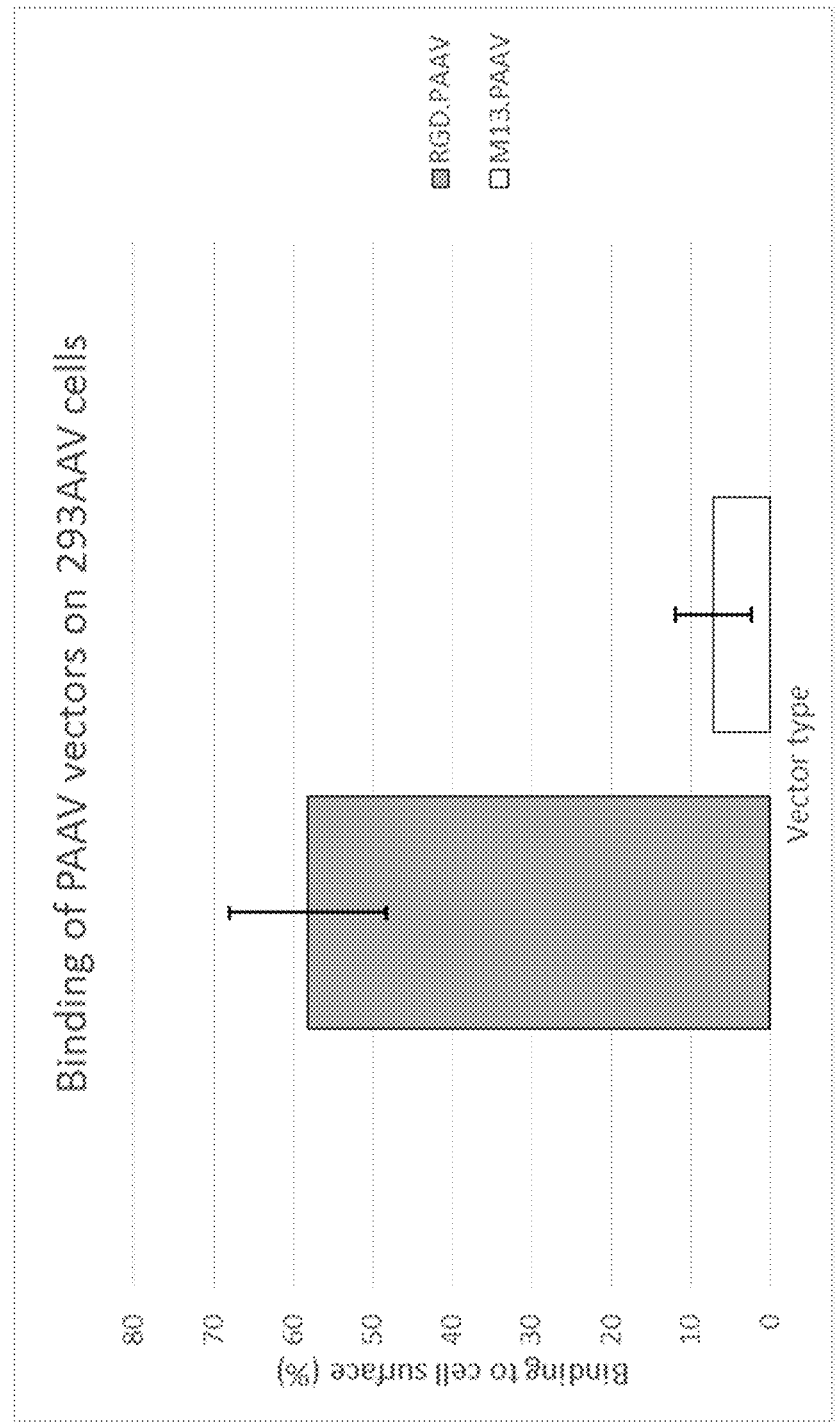

FIG. 6 shows the rAAV transgene cassette on the phagemid genome shown in FIG. 3, which contains a gene of interest (e.g. GFP), the expression of which is driven by a CMV promoter and/or enhancer sequences, and tailed with a polyA signal. The entire transgene cassette is flanked by Inverted Terminal Repeat sequences (ITRs) from AAV;

FIG. 7 shows an embodiment of the Helper phage which is a bacteriophage engineered for rescuing phagemid particles from prokaryotic hosts carrying a phagemid genome, such as that shown in FIG. 3;

FIG. 8 shows a section of the genome of the helper phage shown in FIG. 5 comprising the RGD4C targeting peptide in the pIII minor coat protein;

FIG. 9 shows a first embodiment of a method for producing phagemid-AAV (PAAV) particles;

FIG. 10 shows a second embodiment of a method for producing phagemid-AAV (PAAV) particles;

FIG. 11 shows one embodiment of a phage-based approach for in vitro AAV production showing the three vectors, (i) phagemid-AAV (PAAV), (ii) Rep-Cap phagemid, and (iii) adenohelper phagemid;

FIG. 12 shows the genome map of an embodiment of the adenohelper phagemid vector shown in FIG. 11;

FIG. 13 shows the genome map of an embodiment of a Rep-Cap phagemid vector shown in FIG. 11;

FIG. 14 shows an embodiment of a unified adenohelper-Rep-cap phagemid-AAV (PAAV) vector;

FIG. 15 shows the genome map of an embodiment of the unified adenohelper-Rep-Cap phagemid vector shown in FIG. 11;

FIG. 16 shows an embodiment of in situ AAV production using either the three phagemid vectors shown in FIGS. 11-13, or the unified adenohelper-Rep-Cap-AAV phagemid vector shown in FIGS. 14 and 15;

FIG. 17 shows Transmission Electron Microscopy (TEM) of known AAVP vectors and PAAV vectors according to the invention. (A) RGD.AAVP.GFP filament (pink) is typically 1455.02 nm in length. (B) RGD. PAAV.GFP filament (blue) is typically 729.96 nm in length; helper phage present in virus sample (green) is typically 1186.03 nm in length;

FIG. 18 shows internalisation of known AAVP vectors and PAAV vectors according to the invention in: (A) 293AAV and (B) U87 cells after 2 and 4 hours. Flow cytometric analysis was used with gating threshold set at 20000 events of total cell population. (n=3) *=p<0.05, **=p<0.01;

FIG. 19 shows quantification of GFP-positive cells 9 days post-transduction in (A) 293AAV, (B) 293AAV with the addition of DEAE.DEXTRAN, (C) U87 and (D) U87 with the addition of DEAE.DEXTRAN. Flow cytometric analysis was used with gating threshold set at 20000 events of total cell population. (n=3) *=p<0.05, **=p<0.01;

FIG. 20 shows quantification of genome copy numbers of rAAV-GFP from cell lysates following phagemid-guided gene transfer (A) or transfection (B) of rAAV expression elements. (Experiment A: n=1; Experiment B: n=3);

FIG. 21 shows immunofluorescence staining of UW228 and DAOY human medulloblastoma cells to demonstrate expression of $\alpha_V$, $\beta_3$ and $\beta_5$ integrin subunits, receptor for RGD4C-phagemid. Tumour cells were stained using primary rabbit anti-$\alpha_V$, $\beta_3$ or $\beta_5$ antibodies (diluted 1:50 in PBS-1% BSA), then with goat anti-rabbit AlexaFluor-488 secondary antibody (showed in green) and counterstained with 0.05 µg/ml DAPI (in blue). Images were taken using a confocal microscope;

FIG. 22 shows targeted gene delivery to paediatric medulloblastoma cells by RGD4C-phagemid. Medulloblastoma cells (UW228) were grown on 96 well-plates, then transduced with RGD4C-phagemid vector carrying the Luciferase gene (RGD). Untreated cells or cells treated with the non-targeted vector (M13) were used as negative controls. Luciferase expression was monitored over a time course from day 2 to 4 after transduction;

FIG. 23 shows Western blot analyses showing down regulation of mTOR expression in paediatric UW228 and DAOY medulloblastoma cells following treatment with RGD4C-phagemid carrying the mTOR/shRNA (RGD4C-mTOR/shRNA)). Cell lysates were collected at day 4 post vector treatment, and total proteins were measured by BCA assay. Western blot was probed with a monoclonal antibody to human mTOR (Cell Signalling). Untreated cells (CTR) and cells treated with RGD4C-phagemid, lacking mTOR/shRNA, (RGD4C) were used as negative controls;

FIG. 24 shows combination treatment of temozolomide (TMZ) and RGD4C-phagemid carrying shRNA for mTOR in medulloblastoma. Medulloblastoma cells (UW228 and DAOY) were transduced with RGD4C-phagemid (RGD4C) or RGD4C-phagemid carrying mTOR/shRNA (RGD4C-mTOR/shRNA). Untreated cells were also used as controls. At day 7 post vector treatment, temozolmide (TMZ, 100 uM) was added in a few treated wells to assess effect of combination of vectors with chemotherapy. Images were taken at day 8 after vector treatment;

FIG. 25 shows treatment of medulloblastoma cells with TNFα vectors. UW228 cells were treated with RGD4C-phagemid-TNFα (RGD4C/TNFa) and non-targeted (ctr). A) Expression of TNFα in the medium of vector-treated cells, measured using human TNFα ELISA Max. B) Cell viability, using MIT assay, following expression of TNFα. Error bars: mean±SEM;

FIG. 26 shows immunofluorescence staining of DIPG cells to demonstrate expression of $\alpha_v$, $\beta_3$ and $\beta_5$ integrin subunits, receptor for RGD4C-phagemid. Cells were stained using primary rabbit antibodies then with goat anti-rabbit AlexaFluor-488 secondary antibody. Control cells received secondary antibody alone. Images were taken using a confocal microscope;

FIG. 27 shows selective and dose dependent delivery of gene expression to DIPG cells by RGD4C-phagemid/AAV. Increasing vector dose $1\times10^6$ or $2\times10^6$ TU/cell of RGD4C-phagemid-Luc (RGD4C) carrying the reporter Luc (luciferase) gene was used to treat DIPG cells. Luc expression was measured daily. Non-targeted vector lacking RGD4C (ctr) was used as negative control for targeting. Error bars: mean±SEM;

FIG. 28 shows Treatment with RGD4C-phagemid-TNFa. DIPG cells were transduced with $2\times10^6$ TU/cell RGD4C-phagemid-TNFa (RGD4C) and non-targeted vector as negative control (ctr). Apoptotic activity was measured at day 9 post-vector treatment using caspase-Glo assay (caspase 3/7, caspase 8, and caspase9). Error bars: mean±SEM. *$P\le0.05$, $P\le0.01$, *$P\le0.001$;

FIG. 29 shows luciferase expression after transduction with RGD.PAAV at various concentrations of transducing units;

FIG. 30 shows luciferase expression after transduction with NT.PAAV at various concentrations of transducing units; and FIG. 31 shows the percentage of PAAV vectors bound to the cell surface of 293 AAV cells. RGD.PAAV vectors had 58.2% binding efficiency, whereas M13.PAAV vectors had 7.1% binding efficiency relative to their respective controls.

BACKGROUND

The development of gene delivery technology is instrumental to successful translation of basic research to the society. In the past decade, a number of viral and non-viral vectors have emerged as potential delivery vectors for industrial and therapeutic applications. An important property of vectors, in addition to being efficient at delivering genes, is that it must also be easily produced and commercially viable. In 2006, Hajitou et al. attempted to fulfil the need for such vectors by creating a hybrid between recombinant adeno-associated virus (rAAV) and filamentous bacteriophage (phage), called the Adeno-associated Virus/Phage (AAVP) (*Nature protocols* 2, 523-531 (2007); *Cell* 125, 385-398 (2006)). The resulting AAVP vector possesses favourable characteristics of mammalian and prokaryotic viruses, but does not suffer from the disadvantages that those individual vectors normally carry. However, there are certain aspects of the AAVP vector that still leaves room for significant improvement. Above all, this includes the genetic design of the vector, which carries ramifications in its production and therapeutic properties. Ultimately, this leads to AAVP's relatively low gene transduction efficacy when compared to mammalian viruses.

The research described herein relates to the design of the most advanced version of phage gene delivery vectors and their superiority to the known and existing phage vector, AAVP, by using a so-called "phagemid system", with the new phagemid vector being referred to as Phagemid/Adeno-associated Virion Phagemid (i.e. PAAV). Unlike the AAVP genome, which consists of a rAAV cassette inserted in to the filamentous phage genome, the PAAV genome does not contain any structural phage genes—a prokaryotic helper virus is required to facilitate vector assembly (*Mol Ther* 3, 476-484; *Pharmaceutical research* 27, 400-420 (2010)). Separating the reproductive and therapeutic elements of the virus in to a therapeutic vector carrying the transgene and a separate helper virus carrying the structural genes substantially decreases the genome/vector size and thereby significantly increases transgene capacity, a useful advantage for gene therapy applications of the new system. Consequently, this results in the encapsidation of a eukaryotic virus genome into the capsid of a prokaryotic virus, resulting in a vector as hybrid between eukaryotic genome and prokaryotic capsid with enhanced production yield, gene transduction efficiency and flexibility of the vector system for other applications.

As described in the Examples below, the inventors have:—
1. Designed and constructed a hybrid Phagemid—AAV Vector (PAAV) particle expression system;
2. Characterised and determined whether the phagemid/AAV vector (PAAV) is more efficient at gene transduction than the known AAVP system at various stages, including but not limited to:
   a. Binding to the cell surface,
   b. Internalisation of the vector from the cell surface,
   c. Translocation of the vector genome to the host nuclei, and
   d. Recombinant transgene expression.
3. Determined whether the hybrid phagemid PAAV vector system is capable of producing rAAV from a mammalian producer cell-line.

Figure 1:
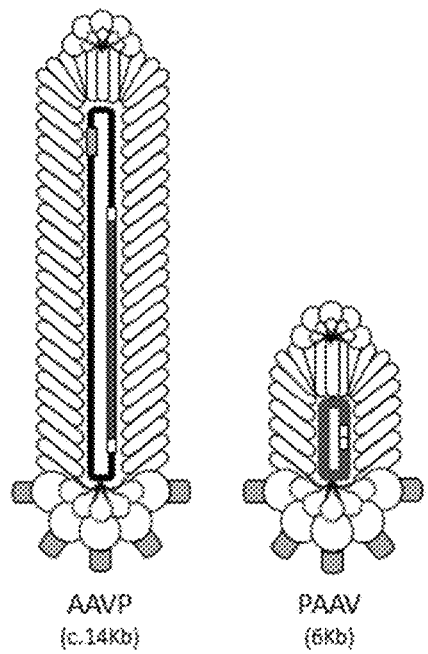

Referring first to FIG. 1, there is shown a table comparing features of the phagemid-AAV (PAAV) particles according to the invention (i.e. virions) with the prior art AAVP viral particles. As can be seen, the PAAV particles (6 kb) of the invention are much smaller than the known AAVP particles (14 kb), i.e. 42% less DNA, and 50% shorter viral particles, and the PAAV particles are produced at yields that far surpass prior art systems (100×) the yield of AAVP). As a result, PAAV particles of the invention can carry larger payloads, which is very useful for delivering multiple transgenes in gene therapy approaches. The inventors have therefore demonstrated that the modified bacteriophage expression system (PAAV) can be used as a highly viral vector for gene therapy, or for large-scale production of viral vectors.

Example 1—Phagemid—AAV Vector (PAAV)
Construction

Referring to FIG. 2, there is shown an embodiment of a Helper Phage genome and a Phagemid genome (PAAV DNA) according to the invention, which are used together upon expression in a prokaryote to produce the phagemid-AAV (PAAV) particle, also shown in FIG. 1. Structural genes are integral to packaging of DNA in to virus particles, and are supplied by the replication-defective Helper phage, which is discussed in detail below. The phagemid genome is extremely parasitic to the Helper phage, meaning it outcompetes the replication-defective helper phage in both replication and packaging.

A) Phagemid/AAV Vector

Referring now to FIG. 3, there is shown one embodiment of the phagemid genome which is a plasmid containing two origins of replication and two other genetic elements. Phagemid genomes require two origins of replication to facilitate both its replication inside the prokaryotic (e.g. bacterial) host and packaging into phagemid particles when rescued by a helper virus.

Figure 4:
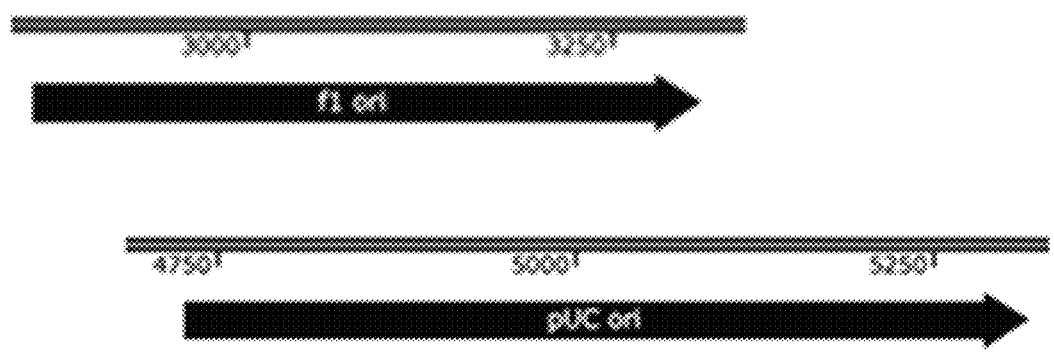
FIG. 4 shows the respective locations of f1 ori and pUC ori on the phagemid genome shown in FIG. 3.

Referring to FIG. 4, the first origin of replication (ori) is a high-copy number origin of replication (pUC ori) that enables replication of the double-stranded phagemid (dsDNA) inside the prokaryotic host at large quantities. The second origin of replication is a phage origin of replication (f1 ori) that enables replication of the plasmid into single-stranded DNA, which can subsequently be packaged into a phagemid vector particle (PAAV).

Referring to FIG. 5, the phagemid genome includes a selection marker gene. In order for the phagemid genome to replicate efficiently inside the prokaryotic host, a selection marker (e.g. ampicillin resistance) is used to ensure expression and provides selective pressure to prevent loss of the phagemid genome in the form of an antibiotic resistance gene (with its own promoter). This ensures expression (and replication) of the phagemid genome when the prokaryotic host is cultured in the presence of the antibiotic that the selection marker confers resistance to.

Referring to FIG. 6, the phagemid genome further includes a recombinant (adeno-associated virus, AAV) transgene cassette which contains a transgene of interest. This can include, but is not limited to, polypeptides/proteins, short hairpin/small interfering/short guiding RNAs, or a combination of both. By way of example only, the transgene shown in FIG. 6 encodes GFP and human Beta-globin. Expression of the transgene is driven by a viral promoter (e.g. CMV) and/or enhancer sequences, and tailed with a polyA signal to prevent degradation. The promoter can also be a mammalian and tumour specific promoter in cancer gene therapy applications (i.e. promoter of the Glucose Regulated Protein [grp78]). The entire transgene cassette is flanked by Inverted Terminal Repeat sequences (ITRs) from AAV, which form a protective hairpin structure allowing the transgene cassette to be stably maintained as concatameric episomal (extra-chromosomal) DNA in the mammalian cell nucleus transduced by the phagemid particle. The ITRs enable AAV transgene cassettes to be stably expressed over a long period of time.

The phagemid, despite having a small genome, is unable to package itself into particles as it lacks structural phage genes. As a result, it requires "rescuing" by a helper virus, as shown in FIG. 7, which provides structural (i.e. capsid) proteins required for formation and extrusion of particles from the prokaryotic host. Conventionally speaking, genetic elements in the vector are generic and used widely in genetic engineering.

B) Helper Phage

Referring to FIG. 7, the helper phage (referred to herein as M13KO7) is a bacteriophage engineered specifically for rescuing phagemid particles (i.e. PAAV) from prokaryotic hosts carrying and/or containing the phagemid genome shown in FIG. 3. The helper phage contains a disrupted origin of replication (p15a, medium copy number) and packaging signal, which significantly deters its ability to package itself into phage particles. Consequently, the phagemid genome will outcompete the helper phage in both replication and packaging.

In order to give the phagemid targeting properties (or multifunctional properties as described in WO 2014/184528), the genome of the helper phage must be engineered to do so, as it provides the structural capsid proteins for phagemid particle assembly. For example, the helper genome may encode a pIII capsid minor coat protein that is configured to display a cell-targeting ligand for enabling delivery of the resultant PAAVP particle to a desired target cell (e.g. tumour). It can also encode at least one pVIII capsid major coat protein that is configured to display a foreign peptide on the resultant PAAV particle. In one embodiment, therefore, it is desired to induce a 9-amino acid mutation in the pIII minor coat protein to confer specificity to angiogenic tumour cells and tumour endothelial cells that express $\alpha_v\beta_3$ and $\alpha_v\beta_5$ integrins. Thus, referring to FIG. 8, the genome of the helper phage comprises the RGD4C targeting peptide (CDCRGDCFC—SEQ ID No: 7).

Once the PAAVP phagemid genome and the Helper phage have been constructed, they are used together to produce, in a prokaryotic host, the Phagemid—AAV Vector (PAAV) particle, as discussed below.

Example 2—Phagemid—AAV Vector (PAAV) Production

The inventors have devised two different methods (Methods 1 and 2) for producing the Phagemid—AAV Vector (PAAV) particle, and these are illustrated in FIGS. 9 and 10.

Notes:
- TG1: a strain of *E. coli* that carries the fertility factor (F′ pilus).
- 2×YT: liquid broth used to culture TG1 *E. coli*.
- Kanamycin: antibiotic resistance selection marker present on the helper phage.
- Ampicillin: antibiotic resistance selection marker present on the phagemid vector.
- TYE top agar: solid media used to culture TG1 *E. coli*, adapted from 2×TY by the addition of 1.25% bacteriological agar.

Phagemid/AAV Vector (PAAV) Production Method 1: Infective Rescue

With reference to FIG. 9:
1. Add 4-5 ml of TG1 *E. coli* carrying PAAV genome pre-culture (overnight) to 60 ml 2×YT (100 µg/mL Ampicillin) supplemented with 1% glucose.
2. Incubate culture at 37° in shaker (250 RPM).
3. Once $OD_{600}$ is in the range of 0.5 to 0.8 (log phase), add at least $1\times10^{10}$ transducing units of helper phage (M13KO7) to culture.
4. Invert to mix. Incubate at 37° for 30 minutes.
5. Pour the infected starter culture from step 3 in to a 2 L flask with 2×YT (100 µg/mL Ampicillin+25 µg/mL Kanamycin) supplemented with 1% glucose to a final volume of 400-450 mL.
6. Incubate overnight in an orbital shaker at 37°, 250 rpm for 16-20 hours.
7. Purify phagemid (PAAV) particles from culture supernatant.

The benefits of Method 1 are its very high yields.

Phagemid/AAV Vector (PAAV) Production Method 2: Stable Producer Cell-Line

With reference to FIG. 10:

Part 1: Competent producer cell-line production
1. Transform and plate TG1 competent *E. coli* (Zymo Research, USA) with ssDNA genome from helper hage M13KO7 in TYE top agar (50 µg/mL Kanamycin)
1. Pick individual colonies and inoculate 5 mL 2×YT media (50 µg/mL Kanamycin) supplemented with 1% glucose.
2. Incubate overnight in an orbital shaker at 37°, 250 rpm for 16-20 hours
3. Check for true positive transformants by extracting DNA from the 5 mL overnight cultures using a commercial extraction kit (QIAGEN, Netherlands) and run on 1% agarose gel (100 volts, 2.5 mA) against a DNA ladder.
4. Prepare chemically competent cells from the correct transformant identified in step 4 using a published protocol (adapted from that published by Krantz et al., UC Berkeley)

Part 2: PAAV Phagemid Particle Production
1. Transform competent cell-line created in Part 1 with a Phagemid/AAV genome and plate on TYE top agar (100 µg/mL Ampicillin+50 µg/mL Kanamycin)
2. Pick a colony and inoculate 5 mL 2×YT (100 µg/mL Ampicillin+50 µg/mL Kanamycin) supplemented with 1% glucose.
3. Incubate in an orbital shaker at 37°, 250 rpm for 4 hours
4. Pour the infected starter culture from step 3 in to a 2 L flask with 2×YT (100 µg/mL Ampicillin+25 µg/mL Kanamycin) supplemented with 1% glucose to a final volume of 400-450 mL
5. Incubate overnight in an orbital shaker at 37°, 250 rpm for 16-20 hours
6. Purify phagemid particles from culture supernatant PAAV Phagemid Particle Purification
1. Transfer the warm overnight culture to centrifuge bottles and pellet the bacteria by centrifugation at 3300G, 4° for 30 minutes.
2. Discard the pellet and transfer supernatant to a clean centrifuge bottle.
3. Add 30% volume of supernatant in each bottle with ice-cold 20% PEG-8000/2.5M NaCl and swirl to mix.
4. Incubate on ice for 4-24 hours
5. Precipitate phagemid particles by centrifugation at 10000G, 4° for 30 minutes. Discard the supernatant.
6. Dry the phagemid particle pellet by centrifugation at 10000G, 4° for 1 minute.
7. Remove remaining supernatant with PEG/NaCl
8. Resuspend the phagemid particle pellet in 0.5-2 mL PBS
9. Filter the resuspended phagemid particle preparation using a 0.45 micron filter.
10. Keep the preparation at 4°. The preparation is stable for up to 2 years 4°. A 25% glycerol stock can be stored indefinitely at −80°.

Example 3—Use of Phagemid—AAV Vector (PAAV) for Gene Therapy Techniques

Examples 1 and 2 describe the components of the invention (i.e. phagemid genome shown in FIG. 3 and helper phage shown in FIG. 7) required to produce the Phagemid—AAV Vector (PAAV) particle and two methods of production. Once produced and purified, the PAAV particles can have a range of uses, such as in gene therapy.

As an example, the PAAVP particles described herein carry the GFP transgene, as it is readily detectable in known assays to show successful delivery to a target cell. In therapy, any transgene may be selected and engineered into the phagemid genome shown in FIG. 3, to be carried in the resultant PAAV particles. For example, the transgene may be any gene encoding a protein, which may have therapeutic or industrial utility. For example, the transgene may encode dystrophin, a blood coagulation factor, insulin or a cytokine receptor sub-unit. The transgene may also encode a short hairpin/small interfering/short guiding RNA molecule using in RNAi therapy. The transgene may encode multiple polypeptides, nucleic acids, or a combination of both, fused together using an internal ribosomal entry site (IRES) or a viral fusion peptide (T2A peptides for in-frame fusion).

Example 4—Use of Phagemid—AAV Vector (PAAVP) for In Vitro AAV Production

In addition to gene therapy, the PAAVP particles described herein can be used in novel methods for producing adeno-associated virus (AAV). Phage-guided AAV production utilizes the ability of the phagemid particles to package large amounts of dsDNA. A typical AAV production system consists of three major elements: rAAV, rep-cap and adenohelper genes, which function together to production recombinant AAV particles. The inventors have devised two different strategies.

With reference to FIG. 11, the first strategy employed is to produce three different phagemid vectors that carry the rAAV-producing elements. These are the Phagemid-AAV Vector (PAAV) (see FIG. 3), the adenohelper phagemid particle (see FIG. 12), and the rep-cap phagemid particle (see FIG. 13). The basic structures of these particles are similar, as they contain two origins of replication and a selection marker, as described in the phagemid/AAV construction section. The key difference, however, is the transgene cassette. While the Phagemid—AAV (PAAV) genome contains an AAV transgene cassette, as shown in FIG. 3, the adenohelper and rep-cap particles contain the adenohelper transgene or rep-cap transgene, as shown in FIGS. 12 and 13, respectively.

In another embodiment, the inventors have genetically engineered a so-called "unified construct" that contains all of the required elements inside a single vector genome, as shown in FIGS. 14 and 15.

When introduced into the same mammalian producer cell (see FIGS. 11 and 14), either on separate vectors or on the same unified vector, the rep-cap and adenohelper genes behave as trans-acting elements that facilitate packaging of the rAAV genome in the phagemid/AAV vector. This production process is comparable to transient co-transfection of three plasmids. However, in this case, the plasmids are replaced with phagemid vectors carrying the very same elements.

Below is described a protocol for PAAV phagemid-guided production of adeno-associated virus (AAV).

Notes:
DMEM: Dulbecco's Modified Eagle Medium.
FBS: Foetal Bovine Serum, a growth supplement.
Complete media: DMEM+10% FBS.
EDTA: Ethyl-diamine tetra-acetic acid, an ion chelator used to dissociate cells by sequestering calcium ions required for tight junction formation.
GlutaMax: a growth supplement, analogue of L-Glutamine.

Protocol for Phagemid-Guided AAV Production:
1. Seed and grow HEK293 cells in complete media (DMEM supplemented with 10% FBS, 20 mM GlutaMax, Penicillin/Streptomycin and Non-Essential Amino Acids) in a 15 cm tissue culture plate for a minimum of 48 hours until 80% confluence is achieved.
2. Mix Phagemid/AAV, rep-cap phagemid and adeno-helper phagemid to achieve a 1:1:1 transducing unit ratio under 5 mL total volume OR Aliquot a unified vector (single vector containing all three elements in a single particle) to achieve 1 million transducing units per cell.
3. Add an equal volume of serum-free DMEM (supplemented with 20 mM GlutaMax) to the transduction mixture made in step 3.
4. Invert to mix. Incubate at room temperature for 15 minutes.
5. Wash the HEK293 cells plated in step 1 with PBS, repeat 3 times.
6. Add the transduction mixture and swirl gently to distribute the mixture evenly.
7. Incubate at 37°, 5% CO2 in a cell culture incubator for 72 hours
   a. After 6 hours of incubation with the transduction mixture, supplement with an equal volume of complete media (DMEM supplemented with 10% FBS, 20 mM GlutaMax, Penicillin/Streptomycin and Non-Essential Amino Acids).
   b. After 24 hours, replace media with complete media (DMEM supplemented with 10% FBS, 20 mM GlutaMax, Penicillin/Streptomycin and Non-Essential Amino Acids).

rAAV Purification:
1. Add 0.5M EDTA solution to the medium in the tissue culture plate to a final concentration of 0.010M, incubate for 5 minutes at room temperature.
2. Collect the cells and media by aspiration and trituration and transfer to a 50 mL centrifuge tube.
3. Pellet the cells by centrifugation at 1500 RPM, 5 minutes, Room temperature.
   a. Optional: collect the supernatant for further AAV purification.
4. Resuspend the cell pellet in 2-5 mL serum-free DMEM.
5. Lyse the cells in the suspension by subjecting to 4 freeze-thaw cycles in an ethanol-dry ice bath and a water bath set to 37°.
6. Centrifuge the cell lysate at 10000G, 10 minutes at Room temperature.
   a. Aliquot the supernatant for quantification/further purification/concentration.
   b. Discard the pellet (debris).

Example 5—Use of Phagemid—AAV Vector (PAAV) for In Situ AAV Production

Referring to FIG. 16, the inventors have devised a method for the in situ production of AAV particles using the PAAV.

Firstly, an optimal dose (or multiple doses) of the three phagemid vectors or the unified vector are introduced in vivo through intravenous/thecal/peritoneal or intramuscular/subcutaneous (or any of the aforementioned routes of administration). The diseased tissue is a tumour displaying the relevant integrins and so the targeting moiety on the phagemid PAAV particles is the RGD4C sequence. The tumour should start to produce rAAV containing the viral transgene encoded in the hybrid phagemid particle and not wild-type AAV. These AAV particles should autoinfect nearby sites, as they naturally have high affinity to mammalian tissue, and eradicate the tumour over a given time.

Example 6—Engineering Pseudovirions for Large-Scale Targeted Gene Transfer and Recombinant Adeno-Associated Virus Production Transmission Electron Microscopy In characterising the particles, the inventors imaged PAAV particles to show that vector size is substantially reduced when using the phagemid-based vector system. Using Transmission Electron Microscopy, the inventors imaged and measured the length of PAAV of the invention and known AAVP particles on mesh copper TEM grids after negative staining with uranyl acetate (see FIG. 17). It was found that the average AAVP particle was 1455.02 nm in length (FIG. 17A), while a typical PAAV particle according to the invention is only 729.96 nm in length (FIG. 17B)—which equates to approximately 50% reduction in particle size. Compared to the helper phage that is used to produce PAAV particles (typically 1186.03 nm, FIG. 17B), the relative vector size is approximately 38% shorter than the helper virus.

The difference in vector size forms the basis of the theory that PAAV may be more efficient as a gene delivery vector than the AAVP, not only in terms of production yield, but also in subsequent infection processes when entering and expressing genes in mammalian cells. As such, the inventors probed vector efficiency at various stages of infection, including binding, internalisation, and gene expression in 293AAV (a derivative of Human Embryonic Kidney 293) and U87 glioblastoma cell lines.

Vector Internalisation

Following binding, vectors undergo receptor-mediated endocytosis by the target cell. To investigate potential differences in vector internalisation, the inventors assayed the number of internalised vectors in target cells at two time-points (2 hours, 2 H; 4 hours, 4 H) using flow cytometry (see FIG. 18). It was found that PAAV vectors were internalised more efficiently at 2 hours (Median Fluorescence Intensity (MFI)=1031.7, 335 higher than AAVP, $p<0.05$) and to a greater overall extent at 4 hours when compared to AAVP in both cell lines. The MFI at 2 hours for PAAV was significantly higher than AAVP by 335 for 293AAV and 207 for U87 cells ($p<0.05$). At 4 hours post-transduction, this difference became substantially greater for 293AAV (829 MFI, $p<0.05$), but less so for U87 (157 MFI, non-significant). Overall, the MFI peaked at 2092 (293AAV, $p<0.05$, FIG. 18A) and 1137 (U87, FIG. 18B) for PAAV1-treated cells, which was significantly higher than AAVP, which respectively peaked at 1063 (293AAV) and 980 (U87). The data demonstrates that PAAV performed consistently better than AAVP in rate and extent of internalisation for both time-points in both cell-lines.

Green Fluorescent Protein Expression Following AAVP and PAAV-Mediated Gene Transfer To investigate whether the differences in vector internalisation translates to increased gene expression, the inventors performed a GFP-expression assay using RGD and NT PAAV.GFP and AAVP.GFP vectors (see FIG. 19). In this experiment, they also tested whether addition of the cationic polymer DEAE.DEXTRAN (Dex) could enhance gene transfer by increasing the bioavailability and endosome-escape of PAAV vectors, as described in WO2014/184529. Nine days post-transduction, cells were trypsinised, and counted and analysed using a flow cytometer. It was found that transgene expression was generally higher in 293AAV cells than U87, regardless of whether Dex was used to assist vector transduction. When vector alone is used, the targeted RGD.PAAV.GFP vector transduces target cells with higher efficacy (7.7%, p<0.01 and 1.4%, p<0.05 GFP +ve cells in 293AAV and U87 cells, respectively)—compared to AAVP, this translates to a 2.44 and 1.56 fold increase respectively in 293AAV and U87 cells (FIG. 19A, C).

When Dex is added however, gene expression increases dramatically for RGD.AAVP and RGD.PAAV vectors. In 293AAV cells, GFP expression in RGD.AAVP.GFP treated cells increased to 25% while RGD. PAAV.GFP treated cells experience a substantial increase to 50% (all p<0.01); addition of Dex resulted in an increase in gene expression of 7.9-fold for RGD.AAVP and 6.5-fold for RGD. PAAVP (FIG. 19B, D). In U87 cells, which is regarded as highly resilient to transduction, Dex was able to augment gene expression by over 3.6-fold in RGD.PAAV.GFP to 4.8% GFP+ve cells (p<0.01)—this was not the case for RGD-.PAAV.GFP, as Dex increased gene expression by only 1.5-fold to 1.3% GFP+ve cells (p<0.05). Interestingly, Dex enabled transduction by NT. PAAV (non-targeted) vectors in 293AAV cells (7.34%), but not with U87.

Phagemid-Guided Recombinant Adeno-Associated Virus Production

To assess whether PAAV and phagemid-derived vectors could be used to produce rAAV in a commercial producer cell-line, the inventors transduced 293AAV cells with three targeted vectors, which are normally plasmids that require transfection for gene transfer. They were able to harvest rAAV particles from the cell lysate and quantify the rAAV gene copy number (GC) per mL over three time-points after phagemid-guided transduction (FIG. 20A). When compared to conventional transfection with FuGene6 (transfection reagent, 3.99e11 GC/mL, FIG. 20B), phagemid-guided rAAV production provides over 1.9-fold increase at 168 hours (7.69e11 GC/mL, FIG. 21A) in rAAV yield. Because phagemid-guided gene transfer requires extensive intracellular processing (unlike transfection), it requires a longer time for viral genes to be expressed and packaged in to functional particles. When yields are compared at the same 72-hour time-point however, transfection produced 1.76e11 GC/mL higher than phage-guided rAAV production. The rAAV yield per mL culture supernatant from transfection or phagemid-guided production dishes at all time points were approx. 8-9e10 GC/mL with no observable trends (data not shown).

Example 7—Construction and Uses of RGD4C-Phagemid

The tripeptide, RGD, is found in proteins of the extracellular matrix, including fibronectin. The integrins act as receptors for fibronectin by binding to the RGD motif located in fibronectin in the site of cell attachment to $\alpha_v\beta_3$ integrin, and so the inventors induced a 9-amino acid mutation in the pIII minor coat protein of the recombinant phagemid particle in order to confer its specificity to tumour cells and angiogenic tumour-associated endothelial cells that express $\alpha_v\beta_3$ and $\alpha_v\beta_5$ integrins. Thus, the genome of the second vector comprises the RGD4C targeting peptide (CDCRGDCFC—SEQ ID No: 7).

Referring to FIG. 21, there is shown immunofluorescence staining of UW228 and DAOY human medulloblastoma cells, which demonstrates the expression of $\alpha_v$, $\beta_3$ and $\beta_5$ integrin subunits, receptor for RGD4C-phagemid. These data demonstrate that the phagemid vector containing the RGD4C targeting peptide can be used for targeted gene delivery and gene therapy in the paediatric brain tumor, medulloblastoma.

Referring to FIG. 22, there is shown targeted gene delivery to paediatric medulloblastoma cells by the RGD4C-phagemid, over a time course of 4 days. The data show that RGD4C-phagemid mediated efficient and selective gene delivery that increased overtime in medulloblastoma.

FIG. 23 shows Western blot analyses showing down-regulation of the mammalian target of rapamycin (mTOR) expression in paediatric UW228 and DAOY medulloblastoma cells following treatment with RGD4C-phagemid carrying the mTOR/shRNA (RGD4C-mTOR/shRNA)). These data demonstrate that the RGD4C-phagemid can be successfully used to deliver shRNA in tumor cells to knock down expression of the therapeutic target mTOR in a selective and efficient way.

FIG. 24 shows combination treatment of temozolomide (TMZ) and RGD4C-phagemid carrying shRNA for mTOR in medulloblastoma cells, known for their resistance to temozolomide. The data demonstrate that targeted the RGD4C-mTOR/shRNA can re-sensitize medulloblastoma cells to TMZ and achieve complete tumor cell eradication. Therefore, targeted knockdown of mTOR expression by the RGD4C-phagemid is an efficient strategy to use in combination with temozolomide against chemoresistant tumor cells, such as medulloblastoma.

FIG. 25 shows treatment of medulloblastoma cells with TNFα vectors. Therefore, RGD4C/TNFα has therapeutic potential for use in targeted tumor killing such as medulloblastoma. FIG. 26 shows immunofluorescence staining of DIPG cells to demonstrate expression of $\alpha_v$, $\beta_3$ and $\beta_5$ integrin subunits, receptor for RGD4C-phagemid. These data demonstrate that the phagemid vector containing the RGD4C targeting peptide can be used for targeted gene delivery and gene therapy in the paediatric brain tumors, DIPG.

FIG. 27 shows selective and dose dependent delivery of gene expression to DIPG cells by RGD4C-phagemid/AAV. These data prove that RGD4C-phagemid can successfully deliver gene expression to DIPG in a dose-dependent and selective way. FIG. 28 shows treatment with RGD4C-phagemid-TNFα. These data demonstrate that RGD4C-phagemid can successfully deliver TNFα to DIPG in a selective manner, resulting in apoptosis induction. Therefore, RGD4C-phagemid-TNFα has therapeutic potential for use in targeted therapy against DIPG.

Example 8—Luciferase Expression of RGD4C-Phagemid

Protocol:

HEK cells were plated in a 48-well plate in complete media (DMEM, 10% FCS, 1% glutamine, 1% penicillin/streptomycin) and incubated for at least 48 hours until 70-80% confluence was reached. Cells were then washed with PBS and transduced with hybrid phage/phagemid vectors suspended in serum-free media (DMEM) for 12 hours before the media was supplemented with complete media. Luciferase expression was measured by adding 10 uL of culture media to 50 uL of prepared Quanti-luc (InvivoGen, USA) reagent. The emission of photos was measured using a plate reader equipped with a luminometer (promega, USA).

FIG. 29 shows luciferase expression after transduction with RGD.PAAV at various concentrations of transducing units, and FIG. 30 shows luciferase expression after transduction with NT.PAAV at various concentrations of transducing units. The graphs demonstrate a dose-dependent exponential relationship between time and expression of luciferase after incubation with hybrid phage/phagemid vectors at various concentrations. The figures demonstrate that quantifiable gene expression can be achieved by phagemid vectors via an assay for secreted luciferase.

Example 9—Binding of RGD.PAAV Vector to 293 AAV Cells

Protocol:

293AAV cells were seeded on 24-well plates in complete media (DMEM+10% FCS, 1% Glutamine, 1% Penicillin/Streptomycin), and were left to reach 70-90% confluence for a minimum of 48 hours. The cells were washed twice with 500 uL PBS and placed on ice before being transduced with 200000 TU/cell (transducing units/cell) of PAAV vectors suspended in 200 uL of serum-free DMEM. After 1 hour of incubation on ice, the media was recovered from the wells and the amount of phagemid particles were titrated on TG1 E. coli and quantified by colony-counting.

Referring to FIG. 31, there is shown the percentage of PAAV vectors bound to the cell surface of 293 AAV cells. RGD.PAAV vectors had 58.2% binding efficiency, whereas M13. PAAV vectors had 7.1% binding efficiency relative to their respective controls.

Discussion

There is strong evidence to suggest that targeted PAAV vectors are more efficient than AAVP vectors at gene transduction in both commercial and disease cell lines. Both internalisation and gene expression data concordantly indicate that PAAV are more efficient than AAVP. Evidence is also provided to suggest a strong synergistic effect between Dex and PAAV vectors on gene transduction that surpasses that of AAVP. Although these data suggest that PAAV are superior to AAVP, it must also be considered that PAAV vector samples contain helper phage contamination. Despite efforts in optimising experimental conditions during vector production, helper phage contamination (in this case, approx. 1/10) is unavoidable and will competitively inhibit transduction as it too displays the RGD targeting sequence on its minor coat protein. Taking this into account, the internalisation and gene expression data may very well be underestimating the 'true' efficacy of RGD.PAAV. Additionally, because the internalisation assay utilises staining of intracellular phage capsid for signal detection, the smaller overall size (and available capsid protein per particle) of the PAAV means that the proportional number of particles internalised cannot be compared directly to that of AAVP, which we have shown using TEM is twice in length compared to PAAV particles. Accordingly, methods of the invention involve a purification step (e.g. FPLC) to remove the helper phage.

It is essential that in addition to providing mechanistic insight, future work must encompass replication of all experiments using pure PAAV samples. In particular, phagemid-guided rAAV production may benefit greatly from decreased competitive inhibition by helper phage contamination and yield multiple fold higher rAAV particles compared to conventional transfection protocols.

SUMMARY

Large-scale production of recombinant adeno-associated virus (rAAV) has been a major hurdle for research, development and commercialization of genetic therapy. Despite being well-researched, rAAV production has been restricted to laboratory scales due to scalability limitations. By far, transient transfection of 'producer' cells has been the most popular technique, yielding high-purity rAAV vectors with no infectious contaminants, despite being extremely costly. Thus, an alternative method for gene transfer in rAAV-production systems is greatly warranted.

Hybrid phagemid vectors that are highly efficient at gene transfer to mammalian cells are described. By combining a rAAV transgene cassette to the phage capsid, it is possible to create a vector system that is easily produced at commercial scales. These phagemid/AAV (PAAV) vectors have very large cloning capacities and are targeted to mammalian cells, meaning transfection reagents are not required. As it is possible to clone all genetic elements for AAV production in to single or multiple phagemid vectors, the inventors have developed this platform technology for large-scale rAAV production. A novel large-scale rAAV production system using PAAV and bacteriophage vectors has been developed, in both adherent cells and in cell-suspensions. This platform technology will enable commercial virus production for clinical translation at GMP standards and pave the way for commercial production of other biosynthetics.

The invention claimed is:

1. A recombinant phagemid particle comprising bacteriophage capsid proteins and a transgene expression cassette, wherein the phagemid particle lacks structural genes that encode the bacteriophage capsid proteins.

2. The recombinant phagemid particle of claim 1, wherein the transgene expression cassette is a viral transgene expression cassette, optionally wherein the transgene expression cassette is an adeno-associated virus (AAV) transgene expression cassette.

3. The recombinant phagemid particle of claim 2, wherein the transgene expression cassette is flanked by Inverted Terminal Repeat sequences (ITRs).

4. The recombinant phagemid particle of claim 1, further comprising a bacteriophage origin of replication.

5. The recombinant phagemid particle of claim 4, wherein the bacteriophage origin of replication is an F1 ori.

6. The recombinant phagemid particle of claim 1, further comprising a bacterial origin of replication.

7. The recombinant phagemid particle of claim 6, wherein the bacterial origin of replication is a pUC ori.

8. The recombinant phagemid particle of claim 1, wherein the recombinant phagemid particle is combined with a cationic polymer to form a complex having a net positive charge.

9. The recombinant phagemid particle of claim 8, wherein the cationic polymer is selected from a group consisting of: chitosan; poly-D-lysine (PDL); diethylaminoethyl (DEAE); diethylaminoethyl-dextran (DEAE.DEX); polyethyleneimine (PEI); polybrene; protamine sulphate; and a cationic lipid.

10. The recombinant phagemid particle of claim 1, wherein the recombinant phagemid particle comprises a DNA sequence that favors targeted integration into a host genome.

11. The recombinant phagemid particle of claim 1, wherein the transgene expression cassette encodes an agent which exerts a biological effect on a target cell.

12. The recombinant phagemid particle of claim 11, wherein the agent is a protein agent or an RNA agent.

13. The recombinant phagemid particle of claim 1, wherein the recombinant phagemid particle comprises a capsid coat protein that is configured to display a cell-targeting ligand for enabling delivery of the particle to the target cell.

14. The recombinant phagemid particle of claim 13, wherein the capsid coat protein is a pIII minor coat protein or a pVIII capsid major coat protein.

15. The recombinant phagemid particle of claim 1, wherein the recombinant phagemid particle comprises a capsid coat protein that is configured to display a foreign peptide thereon.

16. The recombinant phagemid particle of claim 15, wherein the capsid coat protein is a pIII minor coat protein or a pVIII capsid major coat protein.

17. The recombinant phagemid particle of claim 1, wherein the bacteriophage capsid proteins are M13 capsid proteins.

18. A pharmaceutical composition comprising the recombinant phagemid particle of claim 1.

19. A pharmaceutical composition comprising the recombinant phagemid particle of claim 11.

20. A method of performing gene therapy on a subject, the method comprising administering to the subject the pharmaceutical composition of claim 19.

* * * * *

SEQUENCE LISTING

```
Sequence total quantity: 13
SEQ ID NO: 1              moltype = DNA  length = 456
FEATURE                   Location/Qualifiers
source                    1..456
                          mol_type = unassigned DNA
                          note = DNA sequence of an F1 bacteriophage ori
                          organism = unidentified
SEQUENCE: 1
acgcgccctg tagcggcgca ttaagcgcgg cgggtgtggt ggttacgcgc agcgtgaccg    60
ctacacttgc cagcgcccta gcgcccgctc ctttcgcttt cttcccttcc tttctcgcca   120
cgttcgccgg ctttccccgt caagctctaa atcgggggct cccttaggg ttccgattta    180
gtgctttacg gcacctcgac cccaaaaaac ttgatttggg tgatggttca cgtagtgggc   240
catcgccctg atagacggtt tttcgcccctt tgacgttgga gtccacgttc tttaatagtg   300
gactcttgtt ccaaactgga acaacactca accctatctc gggctattct tttgatttat   360
aagggatttt gccgatttcg gcctattggt taaaaaatga gctgatttaa caaaaattta   420
acgcgaattt taacaaaata ttaacgttta caattt                              456

SEQ ID NO: 2              moltype = DNA  length = 589
FEATURE                   Location/Qualifiers
source                    1..589
                          mol_type = unassigned DNA
```

```
                        note = DNA sequence of a PUC ori of an origin of replication
                        organism = unidentified
SEQUENCE: 2
ttgagatcct ttttttctgc gcgtaatctg ctgcttgcaa acaaaaaaac caccgctacc  60
agcggtggtt tgtttgccgg atcaagagct accaactctt tttccgaagg taactggctt 120
cagcagagcg cagataccaa atactgtcct tctagtgtag ccgtagttag gccaccactt 180
caagaactct gtagcaccgc ctacatacct cgctctgcta atcctgttac cagtggctgc 240
tgccagtggc gataagtcgt gtcttaccgg gttggactca agacgatagt taccggataa 300
ggcgcagcgg tcgggctgaa cggggggttc gtgcacacag cccagcttgg agcgaacgac 360
ctacaccgaa ctgagatacc tacagcgtga gctatgagaa agcgccacgc ttcccgaagg 420
gagaaaggcg gacaggtatc cggtaagcgg cagggtcgga acaggagagc gcacgaggga 480
gcttccaggg ggaaacgcct ggtatcttta tagtcctgtc gggtttcgcc acctctgact 540
tgagcgtcga ttttgtgat gctcgtcagg ggggcgagc ctatgaaa               589

SEQ ID NO: 3           moltype = DNA   length = 663
FEATURE                Location/Qualifiers
source                 1..663
                       mol_type = unassigned DNA
                       note = A DNA sequence of a promoter of a Cytomegalovirus
                       organism = unidentified
SEQUENCE: 3
acgcgtggag ctagttatta atagtaatca attacggggt cattagttca tagcccatat  60
atggagttcc gcgttacata acttacggta aatggcccgc ctggctgacc gcccaacgac 120
ccccgcccat tgacgtcaat aatgacgtat gttcccatag taacgtcaat agggactttc 180
cattgacgtc aatgggtgga gtatttacgg taaactgccc acttggcagt acatcaagtg 240
tatcatatgc caagtacgcc ccctattgac gtcaatgacg gtaaatggcc cgcctggcat 300
tatgcccagt acatgacctt atgggacttt cctacttggc agtacatcta cgtattagtc 360
atcgctatta ccatggtgat gcggttttgg cagtacatca atgggcgtgg atagcggttt 420
gactcacggg gatttccaag tctccacccc attgacgtca atgggagttt gttttgcacc 480
aaaatcaacg ggactttcca aaatgtcgta acaactccgc cccattgacg caaatgggcg 540
gtaggcgtgt acggtgggag gtctatataa gcagagctcg tttagtgaac cgtcagatcg 600
cctggagacg ccatccacgc tgttttgacc tccatagaag acaccgggac cgatccagcc 660
tcc                                                              663

SEQ ID NO: 4           moltype = DNA   length = 479
FEATURE                Location/Qualifiers
source                 1..479
                       mol_type = unassigned DNA
                       note = The DNA sequence of one embodiment of a nucleic acid
                         for encoding a polyA tail
                       organism = unidentified
SEQUENCE: 4
acgggtggca tccctgtgac ccctccccag tgcctctcct ggccctggaa gttgccactc  60
cagtgcccac cagccttgtc ctaataaaat taagttgcat cattttgtct gactaggtgt 120
ccttctataa tattatgggg tggaggggggg tggtatggag caaggggcaa gttgggaaga 180
caacctgtag ggcctgcggg gtctattggg aaccaagctg gagtgcagtg gcacaatctt 240
ggctcactgc aatctccgcc tcctgggttc aagcgattct cctgcctcag cctcccgagt 300
tgttgggatt ccaggcatgc atgaccaggc tcagctaatt tttgtttttt tggtagagac 360
ggggtttcac catattggcc aggctggtct ccaactccta atctcaggtg atctacccac 420
cttggcctcc caaattgctg ggattacagg cgtgaaccac tgctcccttc cctgtcctt  479

SEQ ID NO: 5           moltype = DNA   length = 130
FEATURE                Location/Qualifiers
source                 1..130
                       mol_type = unassigned DNA
                       note = The DNA sequence of one (left) embodiment of an
                         Inverted Terminal Repeat sequences (ITR)
                       organism = unidentified
SEQUENCE: 5
cctgcaggca gctgcgcgct cgctcgctca ctgaggccgc ccgggcgtcg ggcgacctt   60
ggtcgcccgg cctcagtgag cgagcgagcg cgcagagagg gagtggccaa ctccatcact 120
aggggttcct                                                       130

SEQ ID NO: 6           moltype = DNA   length = 141
FEATURE                Location/Qualifiers
source                 1..141
                       mol_type = unassigned DNA
                       note = The DNA sequence of one (right) embodiment of an
                         Inverted Terminal Repeat sequences (ITR)
                       organism = unidentified
SEQUENCE: 6
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc 120
gagcgcgcag ctgcctgcag g                                          141

SEQ ID NO: 7           moltype = AA   length = 9
FEATURE                Location/Qualifiers
source                 1..9
                       mol_type = protein
```

```
                        note = The amino acid sequence of a RGD4C targeting peptide
                        organism = unidentified
SEQUENCE: 7
CDCRGDCFC                                                                        9

SEQ ID NO: 8            moltype = DNA  length = 378
FEATURE                 Location/Qualifiers
source                  1..378
                        mol_type = unassigned DNA
                        note = The nucleic acid sequence of one embodiment of a
                        grp78 promoter
                        organism = unidentified
SEQUENCE: 8
cccggggcc  caacgtgagg  ggaggacctg  gacggttacc  ggcggaaacg  gtttccaggt   60
gagaggtcac  ccgagggaca  ggcagctgct  caaccaatag  gaccagctct  cagggcggat  120
gctgcctctc  attggcggcc  gttaagaatg  accagtagcc  aatgagtcgg  ctgggggcg   180
cgtaccagtg  acgtgagttg  cggaggaggc  cgcttcgaat  cggcagcggc  cagcttggtg  240
gcatgaacca  accagcggcc  tccaacgagt  agcgagttca  ccaatcggag  gcctccacga  300
cggggctgcg  gggaggatat  ataagccgag  tcggcgaccg  gcgcgtcga   tactggctgt  360
gactacactg  acttggac                                                    378

SEQ ID NO: 9            moltype = DNA  length = 2876
FEATURE                 Location/Qualifiers
source                  1..2876
                        mol_type = unassigned DNA
                        note = The nucleic acid sequence of one embodiment of a
                        first vector (i.e. a phagemid particle genome)
                        organism = unidentified
SEQUENCE: 9
cctgcaggca  gctgcgcgct  cgctcgctca  ctgaggccgc  ccgggcgtcg  ggcgaccttt    60
ggtcgcccgg  cctcagtgag  cgagcgagcg  cgcagagagg  gagtggccaa  ctccatcact  120
aggggttcct  gcggccgcag  gaaccccctag  tgatggagtt  ggccactccc  tctctgcgcg  180
ctcgctcgct  cactgaggcc  gggcgaccaa  aggtcgcccg  acgcccgggc  tttgcccggg  240
cggcctcagt  gagcgagcga  gcgcgcagct  gcctgcaggg  gcgcctgatg  cggtatttc   300
tccttacgca  tctgtgcggt  atttcacacc  gcatacgtca  aagcaaccat  agtacgcgcc  360
ctgtagcggc  gcattaagcg  cggcgggtgt  ggtggttacg  cgcagcgtga  ccgctacact  420
tgccagcgcc  ctagcgcccg  ctcctttcgc  tttcttccct  tcctttctcg  ccacgttcgc  480
cggctttccc  cgtcaagctc  taaatcgggg  gctcccttta  gggttccgat  ttagtgcttt  540
acggcacctc  gaccccaaaa  aacttgattt  gggtgatggt  tcacgtagtg  ggccatcgcc  600
ctgatagacg  gttttttcgcc  ctttgacgtt  ggagtccacg  ttctttaata  gtggactctt  660
gttccaaact  ggaacaacac  tcaacccctat  ctcgggctat  tcttttgatt  tataagggat  720
tttgccgatt  tcggcctatt  ggttaaaaaa  tgagctgatt  taacaaaaat  ttaacgcgaa  780
ttttaacaaa  atattaacgt  ttacaatttt  atggtgacaa  tctagctctga  tctgctctga  840
tgccgcatag  ttaagccagc  cccgacaccc  gccaacaccc  gctgacgcgc  cctgacgggc  900
ttgtctgctc  ccggcatccg  cttacagaca  agctgtgacc  gtctccggga  gctgcatgtg  960
tcagaggttt  tcaccgtcat  caccgaaacg  cgcgagacga  aagggcctcg  tgatacgcct 1020
atttttatag  gttaatgtca  tgataataat  ggtttcttag  acgtcaggtg  gcacttttcg 1080
gggaaatgtg  cgcggaaccc  ctatttgttt  atttttctaa  atacattcaa  atatgtatcc 1140
gctcatgaga  caataaccct  gataaatgct  tcaataatat  tgaaaaagga  agagtatgag 1200
tattcaacat  ttccgtgtcg  cccttattcc  cttttttgcg  gcattttgcc  ttcctgtttt 1260
tgctcaccca  gaaacgctgg  tgaaagtaaa  agatgctgaa  gatcagttgg  gtgcacgagt 1320
gggttacatc  gaactggatc  tcaacagcgg  taagatcctt  gagagttttc  gccccgaaga 1380
acgttttcca  atgatgagca  cttttaaagt  tctgctatgt  ggcgcggtat  tatcccgtat 1440
tgacgccggg  caagagcaac  tcggtcgccg  catacactat  tctcagaatg  acttggttga 1500
gtactcacca  gtcacagaaa  agcatcttac  ggatggcatg  acagtaagag  aattatgcag 1560
tgctgccata  accatgagtg  ataacactgc  ggccaactta  cttctgacaa  cgatcggagg 1620
accgaaggag  ctaaccgctt  ttttgcacaa  catgggggat  catgtaactc  gccttgatcg 1680
ttgggaaccg  gagctgaatg  aagccatacc  aaacgacgag  cgtgacacca  cgatgcctgt 1740
agcaatggca  acaacgttgc  gcaaactatt  aactggcgaa  ctacttactc  tagcttcccg 1800
gcaacaatta  atagactgga  tggaggcgga  taaagttgca  ggaccacttc  tgcgctcggc 1860
ccttccggct  ggctggttta  ttgctgataa  atctggagcc  ggtgagcgtg  ggtctcgcgg 1920
tatcattgca  gcactgggc   cagatggtaa  gccctcccgt  atcgtagtta  tctacacgac 1980
ggggagtcag  gcaactatgg  atgaacgaaa  tagacagatc  gctgagatag  gtgcctcact 2040
gattaagcat  tggtaactgt  cagaccaagt  ttactcatat  atactttaga  ttgatttaaa 2100
acttcatttt  taatttaaaa  ggatctaggt  gaagatcctt  tttgataatc  tcatgaccaa 2160
aatcccttaa  cgtgagtttt  cgttccactg  agcgtcagac  cccgtagaaa  agatcaaagg 2220
atcttcttga  gatccttttt  ttctgcgcgt  aatctgctgc  ttgcaaacaa  aaaaaccacc 2280
gctaccagcg  gtggtttgtt  tgccggatca  agagctacca  actctttttc  cgaaggtaac 2340
tggcttcagc  agagcgcaga  taccaaatac  tgtccttcta  gtgtagccgt  agttaggcca 2400
ccacttcaag  aactctgtag  caccgcctac  atacctcgct  ctgctaatcc  tgttaccagt 2460
ggctgctgcc  agtggcgata  agtcgtgtct  taccgggttg  gactcaagac  gatagttacc 2520
ggataaggcg  cagcggtcgg  gctgaacggg  gggttcgtgc  acacagccca  gcttggagcg 2580
aacgacctac  accgaactga  gatacctaca  gcgtgagcta  tgagaaagcg  ccacgcttcc 2640
cgaagggaga  aaggcggaca  ggtatccggt  aagcggcagg  gtcggaacag  gagagcgcac 2700
gagggagctt  ccaggggggaa  acgcctggta  tctttatagt  cctgtcgggt  ttcgccacct 2760
ctgacttgag  cgtcgatttt  tgtgatgctc  gtcaggggg   cggagcctat  ggaaaaacgc 2820
cagcaacgcg  gcctttttac  ggttcctggc  cttttgctgg  ccttttgctc  acatgt      2876

SEQ ID NO: 10           moltype = DNA  length = 8696
```

```
FEATURE              Location/Qualifiers
source               1..8696
                     mol_type = unassigned DNA
                     note = The nucleic acid sequence of one embodiment of a
                       second vector (i.e. a helper phage with a RGD sequence)
                     organism = unidentified
SEQUENCE: 10
aacgctacta ctattagtag aattgatgcc accttttcag ctcgcgcccc aaatgaaaat   60
atagctaaac aggttattga ccatttgcga aatgtatcta atggtcaaac taaatctact  120
cgttcgcaga attgggaatc aactgttaca tggaatgaaa cttccagaca ccgtacttta  180
gttgcatatt taaaacatgt tgagctacag caccagattc agcaattaag ctctaagcca  240
tccgcaaaaa tgacctctta tcaaaaggag caattaaagg tactctctaa tcctgacctg  300
ttggagtttg cttccggtct ggttcgcttt gaagctcgaa ttaaaacgcg atatttgaag  360
tcttcgggc ttcctcttaa tcttttgat gcaatccgct ttgcttctga ctataatagt  420
cagggtaaag acctgatttt tgatttatgt tcattctcgt tttctgaact gtttaaagca  480
tttgaggggg attcaatgaa tatttatgac gattccgcag tattgacgc tatccagtct  540
aaacatttta ctattacccc ctctggcaaa acttcttttg caaaagcctc tcgctatttt  600
ggttttatc gtcgtctggt aaacgagggt tatgatagtg ttgctcttac tatgcctcgt  660
aattccttt ggcgttatgt atctgcatta gttgaatgg gtattcctaa atctcaactg  720
atgaatctt ctacctgtaa taatgttgtt ccgttagttc gttttattaa cgtagatttt  780
tcttcccaac gtcctgactg gtataatgag ccagttctta aaatcgcata aggtaattca  840
caatgattaa agttgaaatt aaaccatctc aagcccatt tactactcgt tctggtgttt  900
ctcgtcaggg caagccttat tcactgaatg agcagctttg ttacgttgat ttgggtaatg  960
aatatccggt tcttgtcaag attactcttg atgaaggtca gccagcctat gcgcctggtc 1020
tgtacaccgt tcatctgtcc tctttcaaag ttggtcagtt cggttccctt atgattgacc 1080
gtctgcgcct cgttccggct aagtaacatg gagcaggtcg cggatttga cacaatttat 1140
caggcgatga tacaaatctc cgttgtactt tgtttcgcgc ttggtataat cgctgggggt 1200
caaagatgag tgttttagtg tattctttcg cctcttttcgt tttaggttgg tgccttcgta 1260
gtggcattac gtattttacc cgtttaatgg aaacttcctc atgaaaaagt ctttagtcct 1320
caaagcctct gtagccgttg ctaccctcgt tccgatgctg tctttcgctg ctgagggtga 1380
cgatcccgca aaagcggcct ttaactcccct gcaagcctca gcgaccgaat atatcggtta 1440
tgcgtgggcg atggttgttg tcattgtcgg cgcaactatc ggtatcaagc tgtttaagaa 1500
attcacctcg aaagcaagct gataaaccga tacaattaaa ggctcctttt ggagcctttt 1560
tttttggaga ttttcaacgt gaaaaaatta ttattcgcaa ttcctttagt tgttcctttc 1620
tattctcact ccgcttgtga ttgtagggg gattgtttt gtgaaactgt tgaagttgc 1680
ttagcaaaac cccatacaga aaattcattt actaacgtct ggaaagacga caaactttta 1740
gatcgttacg ctaactatga gggttgtctg tggaatgcta caggcgttgt agtttgtact 1800
ggtgacgaaa ctcagtgtta cggtacatgg gttcctattg ggcttgctat ccctgaaaat 1860
gagggtggtg gctctgaggg tggcggttct gagggtggcg gttctgaggg tggcggtact 1920
aaacctcctg agtacggtga tacacctatt ccgggctata cttatatcaa ccctctcgac 1980
ggcacttatc cgcctggtac tgagcaaaac cccgctaatc ctaatccttc tcttgaggag 2040
tctcagcctc ttaatacttt catgtttcag aataataggt tccgaaatag caggggggca 2100
ttaactgttt atacgggcac tgttactcaa ggcactgacc ccgttaaaac ttattaccag 2160
tacactcctg tatcatcaaa agccatgtat gacgcttact ggaacggtaa attcagagac 2220
tgcgctttcc attctggctt taatgaggat ccattcgttt gtgaatatca aggccaatcg 2280
tctgacctgc ctcaacctcc tgtcaatgct ggcggcggct ctggtggtgg ttctggtggc 2340
ggctctgagg gtggtggctc tgagggtggc ggttctgagg ggcggctc tgagggaggc 2400
ggttccggtg gtggctctgg ttccggtgat tttgattatg aaaagatggc aaacgctaat 2460
aagggggcta tgaccgaaaa tgccgatgaa acgcgctac agtctgacgc taaaggcaaa 2520
cttgattctg tcgctactga ttacggtgct gctatcgatg gtttcattgg tgacgtttcc 2580
ggccttgcta atggtaatgg tgctactggt gattttgctg gctctaattc ccaaatggct 2640
caagtcggtg acggtgataa ttcacccttta atgaataatt tccgtcaata ttaccttcc 2700
ctccctcaat cggttgaatg tcgcccttttt gtctttagcg ctggtaaacc atatgaatt 2760
tctattgatt gtgacaaaat aaacttattc cgtggtgtct ttgcgtttct tttatatgtt 2820
gccaccttta tgtatgtatt ttctacgttt gctaacatac tgcgtaataa ggagtcttaa 2880
tcatgccagt tcttttgggt attccgttat tattgcgttt cctcggtttc cttctggtaa 2940
ctttgttcgg ctatctgctt acttttctta aaaagggctt cggtaagata gctattgcta 3000
tttcattgtt tcttgctctt attattgggc ttaactcaat tcttgtgggt tatctctctg 3060
atattagcgc tcaattaccc tctgactttg ttcagggtgt tcagttaatt ctcccgtcta 3120
atgcgcttcc ctgttttat gttattctct ctgtaaaggc tgctattttc attttgacg 3180
ttaaacaaaa aatcgtttct tatttggatt gggataaata atatggctgt ttattttgta 3240
actggcaaat taggctctgg aaagacgctc gttagcgttg gtaagattca ggataaaatt 3300
gtagctgggt gcaaaatagc aactaatctt gatttaaggc ttcaaaacct cccgcaagtc 3360
gggaggttcg ctaaaacgcc tcgcgttctt agaataccgg ataagccttc tatatctgat 3420
ttgcttgcta ttgggcgcgg taatgattcc tacgatgaaa ataaaaacgg cttgcttgtt 3480
ctcgatgagt gcggtacttg gtttaatacc cgttcttgga atgataagga aagacagccg 3540
attattgatt ggtttctaca tgctcgtaaa ttaggatggg atattatttt tcttgttcag 3600
gacttatcta ttgttgataa acaggcgcgt tctgcattag ctgaacatgt tgtttattgt 3660
cgtcgtctgg acagaattac tttaccttttc gtcggtactt tatattctct tattactgc 3720
tcgaaaatgc ctctgcctaa attacatgtt ggcgttgtta aatatggcga ttctcaatta 3780
agccctactg ttgagcgttg gctttatact ggtaagaatt tgtataacgc atatgatact 3840
aaacaggctt tttctagtaa ttatgattcc ggtgtttatt cttatttaac gccttattta 3900
tcacacggtc ggtatttcaa accattaaat ttaggtcaga agatgaaatt aactaaaata 3960
tatttgaaaa agttttctcg cgttctttgt cttgcgattg gcatttcgc agcatttaca 4020
tatagttata aacccaacc taagccgag gttaaaaagg tagtctctca gacctatgat 4080
tttgataaat tcactattga ctcttctcag cgtcttaatc taagctatcg ctatgttttc 4140
aaggattcta agggaaaatt aattaatagc gacgatttac agaagcaagg ttattcactc 4200
acatatattg atttatgtac tgtttccatt aaaaaaggta attcaaatga aattgttaaa 4260
tgtaattaat tttgttttct tgatgtttgt ttcatcatct tcttttgctc aggtaattga 4320
```

```
aatgaataat tcgcctctgc gcgattttgt aacttggtat tcaaagcaat caggcgaatc  4380
cgttattgtt tctcccgatg taaaaggtac tgttactgta tattcatctg acgttaaacc  4440
tgaaaatcta cgcaatttct ttatttctgt tttacgtgct aataattttg atatggttgg  4500
ttcaattcct tccataattc agaagtataa tccaaacaat caggattata ttgatgaatt  4560
gccatcatct gataatcagg aatatgatga taattccgct ccttctggtg gtttctttgt  4620
tccgcaaaat gataatgtta ctcaaacttt taaaattaat aacgttcggg caaaggattt  4680
aatacgagtt gtcgaattgt ttgtaaagtc taatactcta aatcctcaa atgtattatc  4740
tattgacggc tctaatctat tagttgttag tgcacctaaa gatattttag ataaccttcc  4800
tcaattcctt tctactgttg atttgccaac tgaccagata ttgattgagg gtttgatatt  4860
tgaggttcag caaggtgatg ctttagattt ttcatttgct gctggctctc agcgtggcac  4920
tgttgcaggc ggtgttaata ctgaccgcct cacctctgtt ttatcttctg ctggtggttc  4980
gttcggtatt tttaatggcg atgtttagg gctatcagtt cgcgcattaa agactaatag  5040
ccattcaaaa atattgtctg tgccacgtat tcttacgctt tcaggtcaga agggttctat  5100
ctctgttggc cagaatgtcc cttttattac tggtcgtgtg actggtgaat ctgccaatgt  5160
aaataatcca tttcagacga ttgagcgtca aaatgtaggt atttccatga gcgtttttcc  5220
tgttgcaatg gctggcggta atattgttct ggatattacc agcaaggccg atagtttgag  5280
ttcttctact caggcaagtg atgttattac taatcaaaga agtattgcta caacggttaa  5340
tttgcgtgat ggacagactc ttttactcgg tggcctcact gattataaaa acacttctca  5400
agattctggc gtaccgttcc tgtctaaaat ccctttaatc ggcctcctgt ttagctccg  5460
ctctgattcc aacgaggaaa gcacgttata cgtgctcgtc aaagcaacca tagtacgcgc  5520
cctgtagcgg cgcattaagc gcggcgggtg tggtggttac gcgcagcgtg accgctacac  5580
ttgccagcgc cctagcgccc gctccttcg tttcttccc ttcctttctc gccacgttcg  5640
ccggctttcc ccgtcaagct ctaaatcggg ggctccctt agggttccga tttagtgctt  5700
tacggcacct cgaccccaaa aaacttgatt tgggtgatgg ttcacgtagt gggccatcgc  5760
cctgatagac ggttttttcg cctttgacgt tggagtccac gttctttaat agtggactct  5820
tgttccaaac tggaacaaca ctcaaccta tctcgggacg gcgcttca tgtggcagga  5880
gaaaaaggc tgcaccggtg cgtcagcaga atatgtgata caggatatat tccgcttcct  5940
cgctcactga ctcgctacgc tcggtcgttc gactgcggcg agcggaaatg gcttacgaac  6000
ggggcggaga tttcctggaa gatgccagga agatacttaa cagggaagtg agagggccgc  6060
ggcaaagccg ttttcata ggctccgccc cctgacaag catcacgaaa tctgacgctc  6120
aaatcagtgg tggcgaaacc cgacaggact ataaagatac caggcgtttc ccctggcg  6180
ctccctcgtg cgctctcctg ttcctgcctt tcggtttacc ggtgtcattc cgctgttatg  6240
gccgcgtttg tctcattcca cgcctgacac tcagttccgg gtaggcagtt cgctccaagc  6300
tggactgtat gcacgaaccc ccgttcagt ccgaccgctg cgccttatcc ggtaactatc  6360
gtcttgagtc caacccggaa agacatgcaa aagcaccact ggcagcagcc actggtaatt  6420
gatttagagg agttagtctt gaagtcatgc gccggttaag gctaaactga aaggacaagt  6480
tttggtgact gcgctcctcc aagccagtta cctcggttca aagagttggt agctcagaga  6540
accttcgaaa aaccgcctg caaggcggtt ttttcgtttt cagagcaaga gattacgcgc  6600
agaccaaaac gatctcaaga agatcatctt attaagggt ctgacgctca gtggaacgaa  6660
aactcacgtt aagggatttt ggtcatgaga ttatcaaaaa ggatcttcac ctagatcctt  6720
ttaaattaaa aatgaagttt taaatcaatc taaagtatat atgagtaaac ttggtctgac  6780
agttaccaat gcttaatcag tgaggcacct atctcagcga tctgtctatt tcgttcatcc  6840
atagttgcct gactcccgt cgtgtagata actacgatag gggagggctt accatctggc  6900
cccagtgctg caatgatacc gcgagaccca cgctcaccgg ctccagattt atcagcaata  6960
aaccagccag ccgattcgag ctcgccccgg ggatcgacca gttggtgatt ttgaactttt  7020
gctttgccca ggaacggtct gcgttgtcgg gaagatgcgt gatctgatcc ttcaactcag  7080
caaaagttcg atttattcaa caaagccgcc gtcccgtcaa gtcagcgtaa tgctctgcca  7140
gtgttacaac caattaacca attctgatta gaaaactca tcgagcatca aatgaaactg  7200
caatttattc atatcaggat tatcaatacc atatttttga aaaagccgtt tctgtaatga  7260
aggagaaaac tcaccgagc agttccatag gatggcaaga tcctggtatc ggtctgcgat  7320
tccgactcgt ccaacatcaa tacaacctat taatttcccc tcgtcaaaaa taaggttatc  7380
aagtgagaaa tcaccatgag tgacgactga atccggtgag aatggcaaaa gcttatgcat  7440
ttctttccag acttgttcaa caggccagcc attacgctcg tcatcaaaat cactcgcatc  7500
aaccaaaccg ttattcattc gtgattgcgc ctgagcgaga cgaaatacgc gatcgctgtt  7560
aaaaggacaa ttacaaacag gaatcgaatg caaccggcgc aggaacactg ccagcgcatc  7620
aacaatattt tcacctgaat caggatattc ttctaatacc tggaatgctg ttttcccggg  7680
gatcgcagtg gtgagtaacc atgcatcatc aggagtacgg ataaaatgct tgatggtcgg  7740
aagaggcata aattccgtca gccagtttag tctgaccatc tcatctgtaa catcattggc  7800
aacgctacct ttgccatgtt tcagaaacaa ctctggcgca tcgggcttcc catacaatcg  7860
atagattgtc gcacctgatt gcccgacatt atcgcgagcc catttatacc catataaatc  7920
agcatccatg ttggaattta atcgcggcct cgagcaagac gtttcccgtt gaatatggct  7980
cataacaccc cttgtattac tgtttatgta agcagacagt tttattgttc atgatgatat  8040
atttttatct tgtgcaatgt aacatcagag attttgagac acaacgtggc tttcccccc  8100
cccccctgca ggtctcgggc tattctttg atttataagg gattttgccg atttcggcct  8160
attggttaaa aaatgagctg atttaacaaa aatttaacgc gaatttaac aaaatattaa  8220
cgtttacaat ttaaatattt gcttatacaa tcttcctgtt tttggggctt ttctgattat  8280
caaccggggt acatatgatt gacatgctag ttttacgatt accgttcatc gattctcttg  8340
tttgctccag actctcaggc aatgacctga tagcctttgt agacctctca aaaatagcta  8400
ccctccccgg catgaattta tcagctagaa cggttgaata tcatattgat ggtgatttga  8460
ctgtctccgg cctttctcac ccttttgaat ctttacctac acattactca ggcattgcat  8520
ttaaaatata tgagggttct aaaaattttt atccttgcgt tgaaataaag gcttctcccg  8580
caaaagtatt acagggtcat aatgtttttg gtacaaccga tttagcttta tgctctgagg  8640
ctttattgct taatttgct aattcttgc cttgcctgta tgatttattg gatgtt        8696
```

SEQ ID NO: 11       moltype = DNA   length = 8669
FEATURE             Location/Qualifiers
source              1..8669
                    mol_type = unassigned DNA
                    note = The nucleic acid sequence of a preferred embodiment of a second vector (i.e.a helper phage without a RGD
sequence)
organism = unidentified

SEQUENCE: 11

```
aacgctacta ctattagtag aattgatgcc accttttcag ctcgcgcccc aaatgaaaat   60
atagctaaac aggttattga ccatttgcga aatgtatcta atggtcaaac taaatctact  120
cgttcgcaga attgggaatc aactgttaca tggaatgaaa cttccagaca ccgtacttta  180
gttgcatatt taaaacatgt tgagctacag caccagattc agcaattaag ctctaagcca  240
tccgcaaaaa tgacctctta tcaaaaggag caattaaagg tactctctaa tcctgaccta  300
ttggagtttg cttccggtct ggttcgcttt gaagctcgaa ttaaaacgcg atatttgaag  360
tctttcgggc ttcctcttaa tcttttgat gcaatccgct ttgcttctga ctataatagt   420
cagggtaaag acctgatttt tgatttatgg tcattctcgt tttctgaact gtttaaagca  480
tttgagggg attcaatgaa tatttatgac gattccgcag tattggacgc tatccagtct   540
aaacatttta ctattacccc ctctggcaaa acttcttttg caaaagcctc tcgctatttt  600
ggtttttatc gtcgtctggt aaacgagggt tatgatagtg ttgctcttac tatgcctcgt  660
aattcctttt ggcgttatgt atctgcatta gttgaatgtg gtattcctaa atctcaactg  720
atgaatcttt ctacctgtaa taatgttgtt ccgttagttc gttttattaa cgtagatttt  780
tcttcccaac gtcctgactg gtataatgag ccagttctta aaatcgcata aggtaattca  840
caatgattaa agttgaaatt aaaccatctc aagcccaatt tactactcgt tctggtgttt  900
ctcgtcaggg caagccttat tcactgaatg agcagctttg ttacgttgat ttgggtaatg  960
aatatccggt tcttgtcaag attacttctg atgaaggtca gccagcctat gcgcctggtc 1020
tgtacaccgt tcatctgtcc tctttcaaag ttggtcagtt cggttccctt atgattgacc 1080
gtctgcgcct cgttccggct aagtaacatg gagcaggtcg cggatttcga cacaatttat 1140
caggcgatga tacaaatctc cgttgtactt tgtttcgcgc ttggtataat cgctgggggt 1200
caaagatgag tgttttagtg tattctttcg cctctttcgt tttaggttgg tgccttcgta 1260
gtggcattac gtattttacc cgtttaatgg aaacttcctc atgaaaaagt ctttagtcct 1320
caaagcctct gtagccgttg ctaccctcgt tccgatgctg tctttcgctg ctgagggtga 1380
cgatcccgca aaagcggcct ttaactcct gcaagcctca gcgaccgaat atatcggtta  1440
tgcgtgggcg atggttgttg tcattgtcgg cgcaactatc ggtatcaagc tgtttaagaa 1500
attcacctcg aaagcaagct gataaaccga tacaattaaa agctccttt ggagccttt   1560
tttttggaga ttttcaacgt gaaaaaatta ttattcgcaa ttcctttagt tgttcctttc 1620
tattctcact ccgctgaaac tgttgaaagt tgtttagcaa aaccccatac agaaaattca 1680
tttactaacg tctggaaaga cgacaaaact ttagatcgtt acgctaacta tgagggttgt 1740
ctgtgaatcg ctacaggcgt tgtagtttgt actggtgacg aaactcagtg ttacggtaca 1800
tgggttccta ttgggcttgc tatccctgaa aatgagggtg gtggctctga gggtggcggt 1860
tctgagggtg gcggttctga gggtggcggt actaaacctc ctgagtacgg tgatacacct 1920
attccgggct atacttatat caaccctctc gacggcactt atccgcctgg tactgagcaa 1980
aaccccgcta atcctaatcc ttctcttgag gagtctcagc ctcttaatac tttcatgttt 2040
cagaataata ggttccgaaa taggcagggg gcattaacgt tttatacggg cactgttact 2100
caaggcactg acccgttaa aacttattac cagtacactc ctgtatcatc aaaagccatg 2160
tatgacgctt actggaacgg taaattcaga gactgcgctt tccattctgg ctttaatgag 2220
gatccattcg tttgtgaata tcaaggccaa tcgtctgacc tgcctcaacc tcctgtcaat 2280
gctggcgcg gctctggtgg tggttctggt ggcggctctg agggtggtgg ctctgagggt 2340
ggcggttctg agggtggcgg ctctgaggga ggcggttccg gtggtggctc tggttccggt 2400
gattttgatt atgaaaagat ggcaaacgct aataagggg ctatgaccga aaatgccgat   2460
gaaaacgcgc tacagtctga cgctaaaggc aaacttgatt ctgtcgctac tgattacggt 2520
gctgctatcg atggtttcat tggtgacgtt tccggccttg ctaatggtaa tggtgctact 2580
ggtgattttg ctggctctaa ttcccaaatg gctcaagtcg gtgacggtga taattcacct 2640
ttaatgaata atttccgtca atatttacct tccctccctc aatcggttga atgtcgccct 2700
tttgtcttta gcgctggtaa accatatgaa ttttctattg attgtgacaa aataaactta 2760
ttccgtggtg tcttttgcgtt tcttttatat gttgccacct ttatgtatgt attttctacg 2820
tttgctaaca tactgcgtaa taaggagtct taatcatgcc agttcttttg ggtattccgt 2880
tattattgcg tttcctcggt ttccttctgg taactttgtt cggctatctg cttacttttc 2940
ttaaaaaggg cttcggtaag atagctattg ctatttcatt gtttcttgct cttattattg 3000
ggcttaactc aattcttgtg ggttatctct ctgatattag cgctcaatta ccctctgact 3060
ttgttcaggg tgttcagtta attctcccgt ctaatgcgct tccctgtttt tatgttattc 3120
tctctgtaaa ggctgctatt ttcatttttg acgttaaaca aaaaatcgtt tcttatttgg 3180
attgggataa ataatatggc tgtttatttt gtaactggca aattaggctc tggaaagacg 3240
ctcgttagcg ttggtaagat tcaggataaa atttgtagctg ggtgcaaaat agcaactaat 3300
cttgatttaa ggcttcaaaa cctcccgcaa gtcggggaggt tcgctaaaac gcctcgcgtt 3360
cttagaatac cggataagcc ttctatatct gatttgcttg ctattgggcg cggtaatgat 3420
tcctacgatg aaaataaaaa cggcttgctt gttctcgatg agtgcggtac ttggtttaat 3480
acccgttctt ggaatgataa ggaaagacag ccgattattg attggtttct acatgctcgt 3540
aaattaggat gggattatt ttttcttgtt caggactat ctattgttga taacgggtcc   3600
cgttctgcat tagctgaaca tgttgtttat tgtcgtcgtc tggacagaat tactttacct 3660
tttgtcggta ctttatattc tcttattact ggctcgaaaa tgcctctgcc taaattacat 3720
gttggcgttg ttaaatatgg cgattctcaa ttaagcccta ctgttgagcg ttggctttat 3780
actggtaaga atttgtataa cgcatatgat actaaacagg cttttttctag taattatgat 3840
tccggtgttt attcttattt aacgccttat ttatcacacg gtcgggtattt caaaccattca 3900
aatttaggtc agaagatgaa attaactaaa atatatttga aaaagttttc tcgcgttctt 3960
tgtcttgcga ttggatttgc atcagcacttt acatatagtt atataaccca acctaagccg 4020
gaggttaaaa aggtagtctc tcagacctat gattttgata aattcactat tgactcttct 4080
cagcgtctta atctaagcta tcgctatgtt ttcaaggatt ctaagggaaa attaattaat 4140
agcgacgatt tacagaagca aggttattca ctcacatata ttgatttatg tactgtttcc 4200
attaaaaaag gtaattcaaa tgaaattgtt aaatgtaatt aattttgttt cttgatgttt 4260
tgtttcatca tcttcttttg ctcaggtaat tgaaatgaat aattcgcctc tgcgcgattt 4320
tgtaacttgg tattcaaagc aatcaggcga atccgttatt gtttctcccg atgtaaaagg 4380
tactgttact gtatattcat ctgacgttaa acctgaaaat ctacgcaatt tctttatttc 4440
tgttttacgt gctaataatt ttgatatggt tggttcaatt ccttccataa ttcagaagta 4500
```

```
taatccaaac aatcaggatt atattgatga attgccatca tctgataatc aggaatatga  4560
tgataattcc gctccttctg gtggtttctt tgttccgcaa aatgataatg ttactcaaac  4620
tttaaaaatt aataacgttc gggcaaagga tttaatacga gttgtcgaat tgtttgtaaa  4680
gtctaatact tctaaatcct caaatgtatt atctattgac ggctctaatc tattagttgt  4740
tagtgcacct aaagatattt tagataacct tcctcaattc cttctactg ttgatttgcc   4800
aactgaccag atattgattg agggtttgat atttgaggtt cagcaaggtg atgctttaga  4860
tttttcattt gctgctggct ctcagcgtgg cactgttgca ggcggtgtta atactgaccg  4920
cctcacctct gttttatctt ctgctggtgg ttcgttcggt atttttaatg gcgatgtttt  4980
agggctatca gttcgcgcat taaagactaa tagccattca aaaatattgt ctgtgccacg  5040
tattcttacg ctttcaggtc agaagggttc tatctctgtt ggccagaatg tccctttat   5100
tactggtcgt gtgactggtg aatctgccaa tgtaaataat ccatttcaga cgattgagcg  5160
tcaaaatgta ggtatttcca tgagcgtttt tcctgttgca atggctggcg gtaatattgt  5220
tctggatatt accagcaagg ccgatagttt gagttcttct actcaggcaa gtgatgttat  5280
tactaatcaa agaagtattg ctacaacggt taatttgcgt gatggacaga ctctttact   5340
cggtggcctc actgattata aaaacacttc tcaagattct ggcgtaccgt tcctgtctaa  5400
aatcccttta atcggcctcc tgtttagctc ccgctctgat tccaacgagg aaagcacgtt  5460
atacgtgctc gtcaaagcaa ccatagtacg cgccctgtag cggcgcatta agcgcggcg   5520
gtgtggtggt tacgcgcagc gtgaccgcta cacttgccag cgccctagcg cccgctcctt  5580
tcgctttctt cccttccttt ctcgccacgt tcgccggctt tccccgtcaa gctctaaatc  5640
ggggggctccc tttagggttc cgatttagtg ctttacggca cctcgacccc aaaaaacttg  5700
atttgggtga tggttcacgt agtgggccat cgccctgata cggttttt cgccctttga    5760
cgttggagtc cacgttcttt aatagtggac tcttgttcca aactggaaca acactcaacc  5820
ctatctcggg acggatcgct tcatgtggca ggagaaaaaa ggctgcaccg gtgcgtcagc  5880
agaatatgtg atacaggata tattccgctt cctcgctcac tgactcgcta cgctcggtcg  5940
ttcgactgcg gcgagcggaa atggcttacg aacggggcgg agatttcctg gaagatgcca  6000
ggaagatact taacagggaa gtgagagggc cgcggcaagga ccgttttcc ataggctccga  6060
cccccctgac aagcatcacg aaatctgacg ctcaaatcag tggtggcgaa acccgacagg  6120
actataaaga taccaggcgt ttccccctgg cggctccctc gtgcgctctc ctgttcctgc  6180
cttttcggttt accggtgtca ttccgctgtt atggccgcgt ttgtctcatt ccacgcctga  6240
cactcagttc cgggtaggca gttcgctcca agctggactg tatgcacgaa ccccccgttc  6300
agtccgaccg ctgcgcctta tccggtaact atcgtcttga gtccaacccg gaaagacatg  6360
caaaagcacc actggcagca gccactggta attgatttag aggagttagt cttgaagtca  6420
tgcgccggtt aaggctaaac tgaaaggaca agttttggtg actgcgctcc tccaagccag  6480
ttacctcggt tcaaagagtt ggtagctcag agaaccttcg aaaaaccgcc ctgcaaggcg  6540
ttttttcgt tttcagagca agagattacg cgcagaccaa aacgatctca agaagatcat   6600
cttattaagg ggtctgacgc tcagtggaac gaaaactcac gttaagggat tttggtcatg  6660
agattatcaa aaaggatctt cacctagatc cttttaaatt aaaaatgaag ttttaaatca  6720
atctaaagta tatatgagta aacttggtct gacagttacc aatgcttaat cagtgaggca  6780
cctatctcag cgatctgtct atttcgttca tccatagttg cctgactccc cgtcgtgtag  6840
ataactacga tacgggaggg cttaccatct ggccccagtg ctgcaatgat accgcgagac  6900
ccacgctcac cggctccaga tttatcagca ataaaccagc cagccgattc gagctcgccc  6960
cggggatcga ccagttggtg attttgaact tttgctttgc cacggaacgg tctgcgttgt  7020
cgggaagatg cgtgatctga tccttcaact cagcaaaagt tcgatttatt caacaaagcc  7080
gccgtcccgt caagtcagcg taatgctctg ccagtgttac aaccaattaa ccaattctga  7140
ttagaaaaac tcatcgagca tcaaatgaaa ctgcaattta tcatatcag gattatcaat   7200
accatatttt tgaaaaagcc gttctgtaa tgaaggagaa aactcaccga ggcagttcca   7260
taggatggca agatcctggt atcggtctgc gattccgact cgtccaacat caatacaacc  7320
tattaatttc ccctcgtcaa aaataaggtt atcaagtgag aaatcaccat gagtgacgac  7380
tgaatccggt gagaatggca aaagcttatg catttctttc cagacttgtt caacaggcca  7440
gccattacgc tcgtcatcaa aatcactcgc atcaaccaaa ccgttattca ttcgtgattg  7500
cgcctgagcg agacgaaata cgcgatcgct gttaaaagga caattacaaa caggaatcga  7560
atgcaaccgg cgcaggaaca ctgccagcgc atcaacaata ttttcacctg aatcaggata  7620
ttcttctaat acctggaatg ctgttttccc ggggatcgca gtggtgagta accatgcatc  7680
atcaggagta cggataaaat gcttgatggt cggaagaggc ataaattccg tcagccagtt  7740
tagtctgacc atctcatctg taacatcatt ggcaacgcta cctttgccat gtttcagaaa  7800
caactctggc gcatcgggct tcccatacaa tcgatagatt gtcgcacctg attgcccgac  7860
attatcgcga gcccatttat acccatataa atcagcatcc atgttggaat ttaatcgcgg  7920
cctcgagcaa gacgtttccc gttgaatatg gctcataaca cccctcgtat tactgtttat  7980
gtaagcagac agttttattg ttcatgatga tatatttttta tcttgtgcaa tgtaacatca  8040
gagattttga gacacaacgt ggctttcccc ccccccccct gcaggtctcg ggctattctt   8100
ttgatttata agggatttg ccgatttcgg cctattggtt aaaaaatgag ctgatttaac    8160
aaaaatttaa cgcgaatttt aacaaaatat taacgtttac aatttaaata tttgcttata  8220
caatcttcct gttttgggg cttttctgat tatcaaccgg ggtacatatg attgacatgc   8280
tagtttacg attaccgttc atcgattctc ttgtttgctc cagactctca ggcaatgacc   8340
tgatagcctt tgtagacctc tcaaaaatag ctaccctctc cggcatgaat ttatcagcta  8400
gaacggttga atatcatatt gatggtgatt tgactgtctc cggcctttct cacccttttg  8460
aatctttacc tacacattac tcaggcattg catttaaaat atatgagggt tctaaaaatt  8520
tttatccttg cgttgaaata aaggcttctc cgcaaaagt attacagggt cataatgttt    8580
ttggtacaac cgatttagct ttatgctctg aggctttatt gcttaatttt gctaattctt  8640
tgccttgcct gtatgattta ttggatgtt                                    8669

SEQ ID NO: 12         moltype = DNA  length = 58
FEATURE               Location/Qualifiers
source                1..58
                      mol_type = other DNA
                      note = A nucleic acid sequence comprising a section of a
                        genome of a helper phage comprising a RGD4C targeting
                        peptide in a pIII minor coat protein
                      organism = synthetic construct
```

```
SEQUENCE: 12
tattctcact ccgcttgtga ttgtaggggg gattgttttt gtgaaactgt tgaaagtt         58

SEQ ID NO: 13           moltype = AA  length = 19
FEATURE                 Location/Qualifiers
source                  1..19
                        mol_type = protein
                        note = An amino acid sequence comprising a section of a
                         genome of a helper phage comprising a RGD4C targeting
                         peptide in a pIII minor coat protein
                        organism = synthetic construct
SEQUENCE: 13
YSHSACDCRG DCFCETVES                                                    19
```